(12) United States Patent
Löfstedt et al.

(10) Patent No.: US 8,653,112 B2
(45) Date of Patent: Feb. 18, 2014

(54) SUBSTITUTED PYRAZOLES AS ESTROGEN RECEPTOR LIGANDS

(75) Inventors: Joakim Löfstedt, Uppsala (SE); Xiongyu Wu, Huddinge (SE); Lars Krüger, Huddinge (SE)

(73) Assignee: Karo Bio AB, Huddinge (SE)

( * ) Notice: Subject to any disclaimer, the term of this patent is extended or adjusted under 35 U.S.C. 154(b) by 0 days.

(21) Appl. No.: 13/500,341

(22) PCT Filed: Oct. 6, 2010

(86) PCT No.: PCT/EP2010/064941
§ 371 (c)(1),
(2), (4) Date: Apr. 5, 2012

(87) PCT Pub. No.: WO2011/042475
PCT Pub. Date: Apr. 14, 2011

(65) Prior Publication Data
US 2012/0202853 A1    Aug. 9, 2012

(30) Foreign Application Priority Data

Oct. 7, 2009  (GB) .................................. 0917576.1
Jul. 14, 2010  (GB) .................................. 1011859.4

(51) Int. Cl.
| | | |
|---|---|---|
| *A61K 31/4439* | (2006.01) | |
| *A61K 31/4155* | (2006.01) | |
| *A61K 31/415* | (2006.01) | |
| *C07D 231/38* | (2006.01) | |
| *C07D 413/04* | (2006.01) | |
| *C07D 403/04* | (2006.01) | |
| *C07D 405/04* | (2006.01) | |
| *A61K 31/422* | (2006.01) | |
| *C07D 401/04* | (2006.01) | |

(52) U.S. Cl.
USPC .......... 514/341; 514/378; 514/406; 514/407; 546/275.4; 548/247; 548/364.1; 548/365.7; 548/371.7

(58) Field of Classification Search
None
See application file for complete search history.

(56) References Cited

U.S. PATENT DOCUMENTS

| 7,247,734 B2 * | 7/2007 | Drysdale et al. ........... 548/364.1 |
| 7,612,201 B2 * | 11/2009 | Beswick et al. ........... 544/121 |
| 2007/0191336 A1 | 8/2007 | Flynn et al. | |

FOREIGN PATENT DOCUMENTS

| EP | 0839808 | 5/1998 |
| JP | 2006306755 | 11/2006 |
| WO | 00/07996 | 2/2000 |
| WO | 03/055860 | 7/2003 |
| WO | 2008/006626 | 1/2008 |
| WO | 2008/043567 | 4/2008 |
| WO | 2009/012954 | 1/2009 |
| WO | 2009/019278 | 2/2009 |
| WO | 2009/124968 | 10/2009 |
| WO | 2009/127686 | 10/2009 |
| WO | 2010/031852 | 3/2010 |

OTHER PUBLICATIONS

Ito et al., A medium-term rat liver bioassay for rapid in vivo detection of carcinogenic potential of chemicals, 2003, 94, 3-8.*
Ragno et al, Bioorg. & Med. Chem. 8(6) 2000, 1423-1432.
Shen et al, Org. Lett. 7(11) 2005, 2157-2160.
Yahyazadeh et al, Asian J. Chem., 1491, 2005, 609-611.
Naoum et al, Molecules, 12, 2007, 1259-1273.
Wiglenda et al, J. Med. Chem. 50 2007, 1475-1484.
Karthikeyan et al, Bioorg. Med. Chem. Lett 19 2009, 3370-3373.
CAS 2006:1174156.

* cited by examiner

*Primary Examiner* — Jason M Nolan
*Assistant Examiner* — Po-Chih Chen
(74) *Attorney, Agent, or Firm* — Cantor Colburn LLP

(57) ABSTRACT

The invention provides a compound of formula (I) wherein G is a pyrazole ring as defined in the specification and $R^4$, $R^5$, $R^6$ and $R^7$ are as defined in the specification; or a pharmaceutically acceptable ester, amide, solvate or salt thereof, including a salt of such an ester or amide, and a solvate of such an ester, amide or salt. The invention also provides the use of such compounds in the treatment or prophylaxis of a condition associated with a disease or disorder associated with estrogen receptor activity.

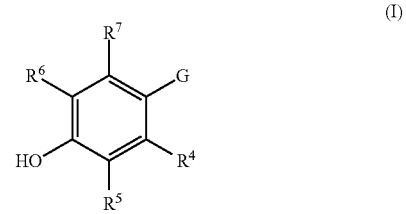

(I)

25 Claims, No Drawings

SUBSTITUTED PYRAZOLES AS ESTROGEN RECEPTOR LIGANDS

CROSS-REFERENCE TO RELATED APPLICATIONS

This application is a U.S. National Stage application of International Application PCT/EP2010/064941 filed 6 Oct. 2010, which claims benefits of GB 0917576.1 filed 7 Oct. 2009 and GB1011859.4 filed 14 Jul. 2010.

FIELD OF INVENTION

This invention relates to compounds which are estrogen receptor ligands and are preferably selective for the estrogen receptor β isoform, to methods of preparing such compounds and to methods for using such compounds in treatment of diseases related to the estrogen receptor such as depressive disorders, anxiety disorders, Alzheimer's disease, cognitive disorders, osteoporosis, elevated blood triglyceride levels, atherosclerosis, endometriosis, urinary incontinence, autoimmune disease, and various cancers including cancer of the lung, colon, breast, uterus and prostate.

BACKGROUND OF INVENTION

The estrogen receptor (ER) is a ligand activated mammalian transcription factor involved in the up and down regulation of gene expression. The natural hormone for the estrogen receptor is β-17-estradiol (E2) and closely related metabolites. Binding of estradiol to the estrogen receptor causes a dimerization of the receptor and the dimer in turn binds to estrogen response elements (ERE's) on DNA. The ER/DNA complex recruits other transcription factors responsible for the transcription of DNA downstream from the ERE into mRNA which is eventually translated into protein. Alternatively the interaction of ER with DNA may be indirect through the intermediacy of other transcription factors, most notably fos and jun. Since the expression of a large number of genes is regulated by the estrogen receptor and since the estrogen receptor is expressed in many cell types, modulation of the estrogen receptor through binding of either natural hormones or synthetic ER ligands can have profound effects on the physiology and pathophysiology of the organism.

Historically it has been believed there was only one estrogen receptor. However a second subtype (ER-β) has been discovered. While both the "classical" ER-α and the more recently discovered ER-β are widely distributed in different tissues, they nevertheless display markedly different cell type and tissue distributions. Therefore synthetic ligands which are either ER-α or ER-β selective may preserve the beneficial effects of estrogen while reducing the risk of undesirable side effects.

Estrogens are critical for sexual development in females. In addition, estrogens play an important role in maintaining bone density, regulation of blood lipid levels, and appear to have neuroprotective effects. Consequently decreased estrogen production in post-menopausal women is associated with a number of diseases such as osteoporosis, atherosclerosis, depression and cognitive disorders. Conversely certain types of proliferative diseases such as breast and uterine cancer and endometriosis are stimulated by estrogens and therefore anti-estrogens (i.e., estrogen antagonists) have utility in the prevention and treatment of these types of disorders.

The efficacy of the natural estrogen, 17β-estradiol, for the treatment of various forms of depressive illness has also been demonstrated and it has been suggested that the anti-depressant activity of estrogen may be mediated via regulation of tryptophan hydroxylase activity and subsequent serotonin synthesis (See, e.g., Lu N Z, Shlaes T A, Cundlah C, Dziennis S E, Lyle R E, Bethea C L, "Ovarian steroid action on tryptophan hydroxylase protein and serotonin compared to localization of ovarian steroid receptors in midbrain of guinea pigs." Endocrine 11:257-267, 1999). The pleiotropic nature of natural estrogen precludes its widespread, more chronic use due to the increased risk of proliferative effects on breast, uterine and ovarian tissues. The identification of the estrogen receptor, ERβ, has provided a means by which to identify more selective estrogen agents which have the desired anti-depressant activity in the absence of the proliferative effects which are mediated by ERα. Thus, it has been shown that therapeutic agents having ERβ-selectivity are potentially effective in the treatment of depression.

What is needed in the art are compounds that can produce the same positive responses as estrogen replacement therapy without the negative side effects. Also needed are estrogen-like compounds that exert selective effects on different tissues of the body.

Haroutounian et al, "Synthesis of novel nitro-substituted triaryl pyrazole derivatives as potential estrogen receptor ligands", Molecules 2007, 12, 1259-1273, discloses the synthesis of certain nitro-substituted triaryl pyrazole derivatives and their binding affinity towards the estrogen receptor (ER) subtypes ERα and ERβ. Wiglenda and Gust, "Structure-activity relationship to understand the estrogen receptor-dependent gene activation of aryl- and alkyl-substituted 1H-imidazoles", J. Med. Chem., 2007, 50, 1475-1484, discloses the synthesis of a series of C5-substituted 1,2,4-triaryl-1H-imidazoles, and the determination of their gene-activating properties on estrogen receptor alpha positive MCF-7 breast cancer cells, stably transfected with the plasmid $ERE_{etc}$luc (MCF-7-2a cells). WO2008/006626 discloses certain 5-membered heterocycles, preferably pyrroles, furans and thiophenes, substituted with three phenyl moieties, and further discloses that the compounds show antiproliferative effects and inhibitory effects on cyclooxygenases. Perumal et al, "Synthesis and antinociceptive activity of pyrazolyl isoxazolines and pyrazolyl isoxazoles", Bioorg. Med. Chem. Lett., 2009, 19, 3370-3373, discloses the synthesis and antinociceptive activity of certain diphenyl pyrazolyl isoxazolines and pyrazolyl isoxazoles. WO 00/07996 discloses compounds having biological activity as estrogen receptor modulators. WO 2003/055860, JP 2006306755 and Org. Lett. Vol. 7 no. 11, 2005, pages 2157-2160 disclose pyrazole compounds having biological activity as heat shock protein 90 inhibitors. US 2007/0191336 discloses compounds having biological activity as nicotinic acetylcholine receptor modulators.

The compounds of the present invention are ligands for estrogen receptors and as such may be useful for treatment or prevention of a variety of conditions related to estrogen functioning.

SUMMARY OF THE INVENTION

This invention provides a compound of formula (I) or a pharmaceutically acceptable ester, amide, solvate or salt thereof, including a salt of such an ester or amide, and a solvate of such an ester, amide or salt,

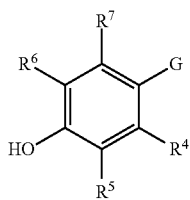

(I)

wherein G represents one of the groups:

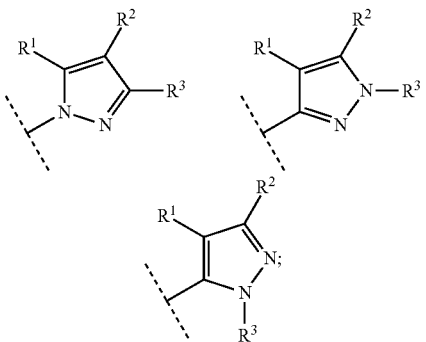

$R^1$ is selected from the group consisting of halogen, cyano, nitro, $OR^A$, $N(R^B)_2$, —$C(O)C_{1-4}$alkyl, —$SO_2C_{1-4}$alkyl, $C_{1-6}$alkyl, $C_{2-6}$alkenyl, $C_{2-6}$alkynyl, halo$C_{1-6}$alkyl, dihalo$C_{1-6}$alkyl, trihalo$C_{1-6}$alkyl, halo$C_{2-6}$alkenyl, dihalo$C_{2-6}$alkenyl, trihalo$C_{2-6}$alkenyl, cyano$C_{1-6}$alkyl, $C_{1-4}$alkoxy$C_{1-6}$ alkyl, $C_{3-8}$cycloalkyl, $C_{3-8}$cycloalkyl$C_{1-6}$alkyl, phenyl, benzyl, and 5-10 membered heterocyclyl, wherein said benzyl or heterocyclyl group is either unsubstituted or said phenyl, benzyl or heterocyclyl group is substituted with from 1 to 3 substituents, each substituent being independently selected from the group consisting of $OR^A$, $N(R^B)_2$, halogen, cyano, nitro, —$C(O)C_{1-4}$alkyl, $C_{1-6}$alkyl, $C_{2-6}$alkenyl, $C_{2-6}$alkynyl, halo$C_{1-6}$alkyl, dihalo$C_{1-6}$alkyl and trihalo$C_{1-6}$alkyl;

$R^2$ is selected from the group consisting of cyano, —CH=N—OH, —C(NH$_2$)=N—OH, —C(O)NH$_2$, $C_{1-6}$alkyl-NH$_2$ and $C_{1-6}$alkyl-OH;

$R^3$ is selected from the group consisting of hydrogen, halogen, $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl; halo$C_{1-6}$alkyl, dihalo$C_{1-6}$alkyl, trihalo$C_{1-6}$alkyl, phenyl, benzyl and 5-10 membered heterocyclyl wherein said benzyl or heterocyclyl group is either unsubstituted or said said phenyl, benzyl or heterocyclyl group is substituted with from 1 to 3 substituents each substituent being independently selected from the group consisting of $OR^A$, halogen, cyano, nitro, $C_{1-6}$alkyl, $C_{2-6}$alkenyl, $C_{2-6}$alkynyl, halo$C_{1-6}$alkyl, dihalo$C_{1-6}$alkyl and trihalo$C_{1-6}$alkyl;

and wherein only one of $R^1$ and $R^3$ may simultaneously be a substituted or unsubstituted phenyl;

each of $R^4$, $R^5$, $R^6$ and $R^7$ is independently selected from the group consisting of hydrogen, $OR^A$, halogen, cyano, nitro, $C_{1-6}$alkyl, $C_{2-6}$alkenyl, $C_{2-6}$alkynyl, halo$C_{1-6}$alkyl, dihalo$C_{1-6}$alkyl and trihalo$C_{1-6}$alkyl;

each $R^A$ is independently selected from the group consisting of hydrogen, $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, phenyl, benzyl and 5-10 membered heterocyclyl, each optionally substituted by from 1 to 3 halogen atoms; and each $R^B$ is independently selected from the group consisting of hydrogen, $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, phenyl, benzyl and 5-10 membered heterocyclyl, each optionally substituted by from 1 to 3 halogen atoms.

Compounds of the invention have surprisingly been found to be ligands of the estrogen receptor. The compounds accordingly have use in the treatment or prophylaxis of conditions associated with estrogen receptor activity.

DETAILED DESCRIPTION OF INVENTION

The compounds of the invention may contain chiral (asymmetric) centers or the molecule as a whole may be chiral. The individual stereoisomers (enantiomers and diastereoisomers) and mixtures of these are within the scope of the present invention.

Certain compounds of the invention contain an oxime group which may be present as the (E) or (Z) oxime isomer. The individual (E) and (Z) oxime isomers and mixtures of these are within the scope of the present invention. Throughout the specification, where the oxime structure is shown with a wavy line bond, this indicates either that a single isomer is present but the stereochemistry is unknown, or that a mixture of both isomers is present.

The present invention provides pyrazole compounds that are estrogen receptor ligands. The term "estrogen receptor ligand" as used herein is intended to cover any moiety which binds to an estrogen receptor. The ligand may act as an agonist, a partial agonist, an antagonist or a partial antagonist. The ligand may be ERβ selective or display mixed ERα and ERβ activity. For example, the ligand may act both as an agonist or a partial agonist of ERβ and as an antagonist or a partial antagonist of ERα. Compounds of the present invention are preferably estrogen receptor ligands that display ERβ selective agonism.

G is preferably a pyrazolyl group selected from the following:

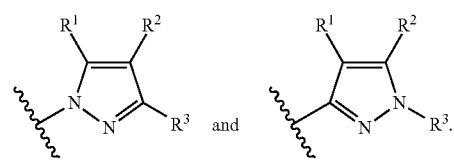

When $R^1$ represents a heterocyclyl group, this group may be saturated or unsaturated, and may contain one or more O, N and/or S atoms. In one preferred embodiment, it is 6-membered or, especially, 5-membered, and is preferably unsaturated, especially aromatic. Suitable heterocyclyl groups include furyl, thienyl, pyrrolyl, pyrrolinyl, pyrrolidinyl, oxazolyl, isoxazolyl, thiazolyl, isothiazolyl, imidazolyl, imidazolinyl, imidazolidine, pyrazolyl, pyrazolinyl, pyrazolidinyl, pyridyl, morpholinyl, and piperidyl, with furyl, pyrrolyl, isoxazolyl, imidazolyl and pyrazolyl being preferred heterocyclyl groups, and isoxazolyl being a particularly preferred heterocyclyl group. Preferred substituents for a heterocyclyl group include 1 to 3, for example 1 or 2, substituents, each substituent being selected from the group consisting of $OR^A$, halogen, cyano, —$C(O)C_{1-4}$alkyl, $C_{1-4}$alkyl, $C_{2-4}$alkenyl, $C_{2-4}$alkynyl, halo$C_{1-4}$alkyl, dihalo$C_{1-4}$alkyl and trihalo $C_{1-4}$alkyl. Especially preferred substituents are selected from halogen, cyano, $C_{1-4}$alkyl (especially methyl or ethyl), —$C(O)C_{1-4}$alkyl, and $OR^A$ in which $R^A$ preferably represents a hydrogen atom or a $C_{1-4}$alkyl group. More especially preferred substituents are selected from halogen, cyano and $C_{1-4}$alkyl (especially methyl or ethyl).

Preferred substituents for a phenyl group $R^1$ include those mentioned above for a heterocyclyl group $R^1$.

Unless otherwise stated, each $R^A$ is preferably independently selected from the group consisting of hydrogen, $C_{1-4}$alkyl, $C_{2-4}$alkenyl, $C_{2-4}$alkynyl, $C_{3-6}$cycloalkyl, phenyl and benzyl. Preferably each $R^A$ independently represents hydrogen or $C_{1-4}$alkyl, especially methyl.

Unless otherwise stated, each $R^B$ is preferably independently selected from the group consisting of hydrogen and $C_{1-4}$alkyl, especially methyl.

Preferably $R^1$ is selected from the group consisting of $C_{1-6}$alkyl, $C_{2-6}$alkenyl, $C_{2-6}$alkynyl, $N(R^B)_2$, phenyl benzyl, or a 5-10 membered heterocyclyl, wherein said wherein said benzyl or heterocyclyl group is either unsubstituted or said phenyl, benzyl or heterocyclyl group is substituted as above. More preferably, $R^1$ represents $N(R^B)_2$, phenyl or a 5-10 membered heterocyclyl, wherein said heterocyclyl group is either unsubstituted or said phenyl or heterocyclyl group is substituted with from 1 to 3 substituents, each substituent being independently selected from the group consisting of halogen and $C_{1-6}$alkyl; and $R^B$ represents $C_{1-6}$alkyl. Most preferably, $R^1$ represents $N(R^B)_2$, phenyl or a 5-6 membered heterocyclyl, wherein said heterocyclyl group is either unsubstituted or said phenyl or heterocyclyl group is substituted with from 1 to 3 substituents, each substituent being independently selected from the group consisting of halogen and $C_{1-6}$alkyl; and $R^B$ represents $C_{1-6}$alkyl. In a further preferred embodiment, $R^1$ represents $N(R^B)_2$, phenyl or a 5-membered heterocyclyl, wherein said heterocyclyl group is either unsubstituted or said phenyl or heterocyclyl group is substituted with 1 or 2 substituents, each substituent being independently selected from the group consisting of halogen and $C_{1-3}$alkyl; and $R^B$ represents $C_{1-3}$alkyl.

When $R^1$ represents an $N(R^B)_2$ group, each $R^B$ is preferably independently selected from the group consisting of $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, phenyl, benzyl and 5-10 membered heterocyclyl, each optionally substituted by from 1 to 3 halogen atoms, with preferred $R^B$ substituents being $C_{1-6}$alkyl groups, particularly $C_{1-3}$alkyl groups.

In one preferred embodiment, $R^1$ is selected from $C_{2-6}$alkenyl, $N(R^B)_2$, phenyl and 5-10 membered heterocyclyl, wherein said phenyl or heterocyclyl group is either unsubstituted or said phenyl or heterocyclyl group is substituted with from 1 to 3 substituents, each substituent being independently selected from the group consisting of halogen, cyano, nitro, $C_{1-6}$alkyl, especially $C_{1-3}$alkyl, and trihalo$C_{1-6}$alkyl, especially trihalo$C_{1-3}$alkyl; and each $R^B$ representing $C_{1-6}$alkyl, especially $C_{1-3}$alkyl;

Preferably $R^2$ represents —CH=N—OH, —C(NH$_2$)=N—OH, or —C(O)NH$_2$, especially —CH=N—OH or —C(NH$_2$)=N—OH.

In one embodiment, $R^3$ represents hydrogen, halogen, $C_{1-6}$alkyl, $C_{2-6}$alkenyl, phenyl, or a 5-10 membered heterocyclyl wherein said heterocyclyl group is either unsubstituted or said phenyl or heterocyclyl group is substituted as above. Preferred heterocycles are as mentioned above. More preferably, $R^3$ represents hydrogen, halogen, $C_{1-6}$alkyl, $C_{2-6}$alkenyl, phenyl, or a 5-10 membered heterocyclyl wherein said heterocyclyl group is either unsubstituted or said phenyl or heterocyclyl group is substituted with from 1 to 3 substituents each substituent being independently selected from the group consisting of halogen, cyano, $C_{1-6}$alkyl and trihalo$C_{1-6}$alkyl. In a further preferred embodiment, $R^3$ is selected from the group consisting of hydrogen, halogen, $C_{1-6}$alkyl, $C_{2-6}$alkenyl and $C_{2-6}$alkynyl and $C_{3-8}$cycloalkyl.

Most preferably, $R^3$ represents hydrogen, halogen or $C_{1-3}$alkyl, especially hydrogen, fluorine, methyl or ethyl.

Preferably each of $R^4$, $R^5$, $R^6$ and $R^7$ is independently selected from the group consisting of hydrogen, $OR^A$, halogen, cyano, nitro, $C_{1-4}$alkyl, for example methyl, halo$C_{1-4}$alkyl, for example chloro- or fluoro-methyl, dihalo$C_{1-4}$alkyl, for example dichloro- or difluoromethyl, and trihalo$C_{1-4}$alkyl, for example trichloro- or trifluoromethyl. More preferably each of $R^4$, $R^5$, $R^6$ and $R^7$ is independently selected from the group consisting of hydrogen, OH, halogen, cyano, methyl, or trifluoromethyl, or each of $R^4$, $R^5$, $R^6$ and $R^7$ independently represents hydrogen, halogen, cyano, nitro, or $C_{1-6}$-, preferably $C_{1-3}$-, alkyl. Most preferably each of $R^4$, $R^5$, $R^6$ and $R^7$ independently represents hydrogen, methyl and/or halogen, especially fluorine. For example, each of $R^4$, $R^5$, $R^6$ and $R^7$ may represent hydrogen; or $R^4$ may represent hydrogen, methyl or halogen, especially fluorine, and each of $R^5$, $R^6$ and $R^7$ may represent hydrogen.

In one embodiment of the invention, G represents

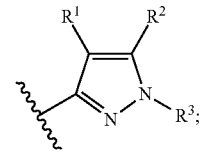

$R^1$ represents a 5-membered heterocycle substituted with two $C_{1-3}$alkyl groups; $R^2$ represents —C(NH$_2$)=N—OH; $R^3$ represents $C_{1-3}$alkyl; $R^4$ represents fluoro; and $R^5$, $R^6$ and $R^7$ represent hydrogen.

In one preferred embodiment, $R^1$ is selected from $C_{2-6}$alkenyl, $N(R^B)_2$, phenyl and 5-10 membered heterocyclyl, wherein said phenyl or heterocyclyl group is either unsubstituted or said phenyl or heterocyclyl group is substituted with from 1 to 3 substituents, each substituent being independently selected from the group consisting of halogen, cyano, nitro, $C_{1-6}$alkyl (especially $C_{1-3}$alkyl) and trihalo$C_{1-6}$alkyl (especially trihalo$C_{1-3}$alkyl); and each $R^B$ representing $C_{1-6}$alkyl (especially $C_{1-3}$alkyl); $R^3$ is selected from the group consisting of hydrogen, halogen, $C_{1-6}$alkyl, $C_{2-6}$alkenyl, $C_{2-6}$alkynyl, and $C_{3-8}$cycloalkyl; and each of $R^4$, $R^5$, $R^6$ and $R^7$ independently represents hydrogen, halogen, cyano, nitro or $C_{1-6}$alkyl (especially $C_{1-3}$alkyl).

In this embodiment, preferably each of $R^4$, $R^5$, $R^6$ and $R^7$ is independently selected from the group consisting of hydrogen, halogen and methyl, for example hydrogen and halogen. For example, $R^4$ may represent hydrogen, methyl or halogen, especially halogen, and $R^5$, $R^6$ and $R^7$ may represent hydrogen. Preferably $R^4$ represents hydrogen, methyl or fluoro, and each of $R^5$, $R^6$ and $R^7$ represents hydrogen.

In the above embodiments, preferably G represents

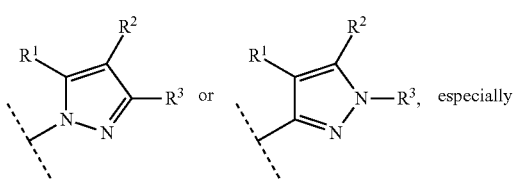

especially

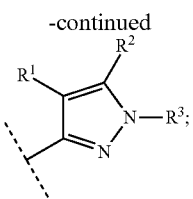

and preferably R² is selected from the group consisting of —CH=N—OH, —C(NH₂)=N—OH and —C(O)NH₂, especially —CH=N—OH and C(NH₂)=N—OH; and preferably R³ is $C_{1-3}$alkyl, especially methyl or ethyl, most especially methyl.

In this embodiment, preferably R¹ is selected from phenyl and 5- or 6-membered heterocyclyl, wherein said phenyl or heterocyclyl group is substituted with from 1 to 3 substituents, each substituent being independently selected from the group consisting of halogen and $C_{1-3}$alkyl. Most preferably R¹ represents a 5- or 6-membered heterocyclyl, especially 5-membered heterocyclyl, said heterocyclyl preferably being substituted with two $C_{1-3}$alkyl groups; for example methyl groups. Especially preferred are components in which R¹ represents 5-membered heterocyclyl, said heterocyclyl being substituted with two methyl groups.

5-membered heterocyclyl is preferably aromatic, and is suitably selected from isoxazolyl, isothiazolyl, pyrrolyl, furanyl, pyrazolyl and thiophenyl, especially isoxazolyl, especially dimethylisoxazolyl.

Thus in a particular embodiment, G represents

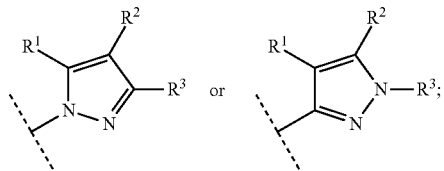

R¹ is selected from $C_{2-6}$alkenyl, $N(R^B)_2$, phenyl and 5-6 membered heterocyclyl, wherein said phenyl or heterocyclyl group is substituted with from 1 to 3 substituents, each substituent being independently selected from the group consisting of halogen, cyano and $C_{1-3}$alkyl; and each $R^B$ representing $C_{1-3}$alkyl; R² is selected from the group consisting of cyano, —CH=N—OH, —C(NH₂)=N—OH, —C(O)NH₂ and $C_{1-6}$alkyl-OH; R³ is independently selected from the group consisting of hydrogen and $C_{1-6}$alkyl; and each of R⁴, R⁵, R⁶ and R⁷ independently represents hydrogen or halogen.

In a further particular embodiment, G represents

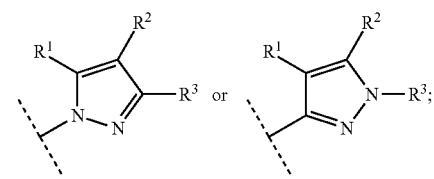

R¹ represents 3,5-dimethyl isoxazole-4-yl, 3,5-dimethyl-isothiazol-4-yl, 1,3-dimethylpyrrol-2-yl or —C(CH₃)=CH.CH₃; R² represents —CH=N—OH or —C(NH₂)=N—OH; R³ represents methyl or ethyl; R⁴ represents hydrogen, fluorine or methyl; and each of R⁵, R⁶ and R⁷ represents hydrogen.

Particularly preferred are compounds in which G represents

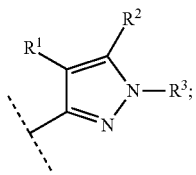

R¹ represents a 5-membered heterocyclyl, especially isoxazolyl, said heterocyclyl being substituted with two methyl groups; R² is selected from the group consisting of —CH=N—OH, —C(NH₂)=N—OH and —C(O)NH₂, especially —CH=N—OH or —C(NH₂)=N—OH; R³ is independently selected from the group consisting of hydrogen and $C_{1-3}$alkyl, especially methyl; R⁴ represents halogen, especially fluorine; and each of R⁵, R⁶ and R⁷ represents hydrogen.

Compounds of the formula (I) include, but are not limited to, the compounds specifically named in the Examples herein, and pharmaceutically acceptable esters, amides, solvates and salts thereof, including salts of such esters and amides, and solvates of such esters, amides and salts.

Further compounds of the formula (I) include, but are not limited to, the following compounds:

5-(2,4-dimethylfuran-3-yl)-1-(2-fluoro-4-hydroxyphenyl)-N-hydroxy-3-methyl-1H-pyrazole-4-carboximidamide;

5-(2,5-dimethyl-1H-imidazol-1-yl)-1-(2-fluoro-4-hydroxyphenyl)-N'-hydroxy-3-methyl-1H-pyrazole-4-carboximidamide;

4-(2,5-dimethyl-1H-imidazol-1-yl)-3-(2-fluoro-4-hydroxyphenyl)-N-hydroxy-1-methyl-1H-pyrazole-5-carboximidamide;

4-(2,4-dimethylfuran-3-yl)-3-(2-fluoro-4-hydroxyphenyl)-N-hydroxy-1-methyl-1H-pyrazole-5-carboximidamide;

4-(5-fluoro-2,4-dimethylfuran-3-yl)-3-(2-fluoro-4-hydroxyphenyl)-N'-hydroxy-1-methyl-1H-pyrazole-5-carboximidamide;

4-(5-chloro-2,4-dimethylfuran-3-yl)-3-(2-fluoro-4-hydroxyphenyl)-N'-hydroxy-1-methyl-1H-pyrazole-5-carboximidamide;

5-(2,4-dimethylfuran-3-yl)-1-(2-fluoro-4-hydroxyphenyl)-N'-hydroxy-3-methyl-1H-pyrazole-4-carboximidamide;

4-(1,4-dimethyl-1H-imidazol-5-yl)-3-(2-fluoro-4-hydroxyphenyl)-N'-hydroxy-1-methyl-1H-pyrazole-5-carboximidamide;

4-(1,3-dimethyl-1H-pyrrol-2-yl)-3-(2-fluoro-4-hydroxyphenyl)-N'-hydroxy-1-methyl-1H-pyrazole-5-carboximidamide;

5-(5-fluoro-2,4-dimethylfuran-3-yl)-1-(2-fluoro-4-hydroxyphenyl)-N'-hydroxy-3-methyl-1H-pyrazole-4-carboximidamide;

5-(5-chloro-2,4-dimethylfuran-3-yl)-1-(2-fluoro-4-hydroxyphenyl)-N'-hydroxy-3-methyl-1H-pyrazole-4-carboximidamide;

5-(1,4-dimethyl-1H-imidazol-5-yl)-1-(2-fluoro-4-hydroxyphenyl)-N'-hydroxy-3-methyl-1H-pyrazole-4-carboximidamide;

5-(3,5-dimethylisothiazol-4-yl)-1-(2-fluoro-4-hydroxyphenyl)-N'-hydroxy-3-methyl-1H-pyrazole-4-carboximidamide;

4-(2,4-dimethylfuran-3-yl)-3-(2-fluoro-4-hydroxyphenyl)-1-methyl-1H-pyrazole-5-carbaldehyde oxime;

4-(5-fluoro-2,4-dimethylfuran-3-yl)-3-(2-fluoro-4-hydroxyphenyl)-1-methyl-1H-pyrazole-5-carbaldehyde oxime;
4-(5-chloro-2,4-dimethylfuran-3-yl)-3-(2-fluoro-4-hydroxyphenyl)-1-methyl-1H-pyrazole-5-carbaldehyde oxime;
5-(2,4-dimethylfuran-3-yl)-1-(2-fluoro-4-hydroxyphenyl)-3-methyl-1H-pyrazole-4-carbaldehyde oxime;
4-(1,4-dimethyl-1H-imidazol-5-yl)-3-(2-fluoro-4-hydroxyphenyl)-1-methyl-1H-pyrazole-5-carbaldehyde oxime;
4-(2,5-dimethyl-1H-imidazol-1-yl)-3-(2-fluoro-4-hydroxyphenyl)-1-methyl-1H-pyrazole-5-carbaldehyde oxime;
5-(5-fluoro-2,4-dimethylfuran-3-yl)-1-(2-fluoro-4-hydroxyphenyl)-3-methyl-1H-pyrazole-4-carbaldehyde oxime;
5-(5-chloro-2,4-dimethylfuran-3-yl)-1-(2-fluoro-4-hydroxyphenyl)-3-methyl-1H-pyrazole-4-carbaldehyde oxime;
4-(1,3-dimethyl-1H-pyrrol-2-yl)-3-(2-fluoro-4-hydroxyphenyl)-1-methyl-1H-pyrazole-5-carbaldehyde oxime;
5-(3,5-dimethylisothiazol-4-yl)-1-(2-fluoro-4-hydroxyphenyl)-3-methyl-1H-pyrazole-4-carbaldehyde oxime;
5-(1,4-dimethyl-1H-imidazol-5-yl)-1-(2-fluoro-4-hydroxyphenyl)-3-methyl-1H-pyrazole-4-carbaldehyde oxime;
5-(2,5-dimethyl-1H-imidazol-1-yl)-1-(2-fluoro-4-hydroxyphenyl)-3-methyl-1H-pyrazole-4-carbaldehyde oxime;
or a pharmaceutically acceptable ester, amide, solvate or salt thereof, including a salt of such an ester or amide, and a solvate of such an ester, amide or salt.

In the compounds listed above and in the Examples, the compound names were generated in accordance with IUPAC by the ACD Labs 8.0/name program, version 8.05 and/or with ISIS DRAW Autonom 2000 and/or ChemBioDraw Ultra version 11.0.

Depending upon the substituents present in compounds of the formula I, the compounds may form esters, amides, carbamates and/or salts. Salts and solvates of compounds of formula (I) which are suitable for use in medicine are those wherein a counterion or associated solvent is pharmaceutically acceptable. However, salts and solvates having non-pharmaceutically acceptable counterions or associated solvents are within the scope of the present invention, for example, for use as intermediates in the preparation of the compounds of formula (I) and their pharmaceutically acceptable salts, solvates and physiologically functional derivatives. By the term "physiologically functional derivative" is meant a chemical derivative of a compound of formula (I) having the same physiological function as the free compound of formula (I), for example, by being convertible in the body thereto. Esters, amides and carbamates are examples of physiologically functional derivatives.

Suitable salts according to the invention include those formed with organic or inorganic acids. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_1$-$C_4$)-alkyl- or aryl-sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine. Other acids such as oxalic, while not in themselves pharmaceutically acceptable, may be useful as intermediates in obtaining the compounds of the invention and their pharmaceutical acceptable acid addition salts.

Compounds of formula (I) may have an appropriate group converted to an ester, an amide or a carbamate. Typical ester and amide and carbamate groups formed from an —OH or —NHR$^B$ group in the compound of the formula I include —OC(O)R$^B$, —NR$^B$C(O)R$^B$, —NR$^B$CO$_2$R$^B$—OSO$_2$R$^B$, and —NR$^B$SO$_2$R$^B$, where R$^B$ has one of the meanings given above.

Those skilled in the art of organic chemistry will appreciate that many organic compounds can form complexes with solvents in which they are reacted or from which they are precipitated or crystallized. These complexes are known as "solvates". For example, a complex with water is known as a "hydrate".

A compound which, upon administration to the recipient, is capable of being converted into a compound of formula (I) as described above, or an active metabolite or residue thereof, is known as a "prodrug". A prodrug may, for example, be converted within the body, e.g. by hydrolysis in the blood, into its active form that has medical effects. Pharmaceutical acceptable prodrugs are described in T. Higuchi and V. Stella, Prodrugs as Novel Delivery Systems, Vol. 14 of the A. C. S. Symposium Series (1976); "Design of Prodrugs" ed. H. Bundgaard, Elsevier, 1985; and in Edward B. Roche, ed., Bioreversible Carriers in Drug Design, American Pharmaceutical. Association and Pergamon Press, 1987, which are incorporated herein by reference.

The following definitions apply to the terms as used throughout this specification, unless otherwise limited in specific instances.

As used herein, the term "alkyl" means both straight and branched chain saturated hydrocarbon groups. Examples of alkyl groups include methyl, ethyl, n-propyl, iso-propyl, n-butyl, t-butyl, i-butyl, sec-butyl, pentyl and hexyl groups. Among unbranched alkyl groups, there are preferred methyl, ethyl, n-propyl, iso-propyl, n-butyl groups. Among branched alkyl groups, there may be mentioned t-butyl, i-butyl, 1-ethylpropyl and 1-ethylbutyl groups.

As used herein, the term "alkoxy" means the group O-alkyl, where "alkyl" is used as described above. Examples of alkoxy groups include methoxy and ethoxy groups. Other examples include propoxy and butoxy.

As used herein, the term "alkenyl" means both straight and branched chain unsaturated hydrocarbon groups with at least one carbon carbon double bond. Examples of alkenyl groups include ethenyl, propenyl, butenyl, pentenyl and hexenyl. Preferred alkenyl groups include ethenyl, 1-propenyl, 2-propenyl and but-2-enyl.

As used herein, the term "alkynyl" means both straight and branched chain unsaturated hydrocarbon groups with at least one carbon carbon triple bond. Examples of alkynyl groups include ethynyl, propynyl, butynyl, pentynyl and hexynyl. Preferred alkynyl groups include ethynyl, 1-propynyl and 2-propynyl.

As used herein, the term "cycloalkyl" means a saturated group in a ring system. A cycloalkyl group can be monocyclic or bicyclic. A bicyclic group may, for example, be fused or bridged. Examples of monocyclic cycloalkyl groups include cyclopropyl, cyclobutyl and cyclopentyl. Other examples of monocyclic cycloalkyl groups are cyclohexyl, cycloheptyl and cyclooctyl. Examples of bicyclic cycloalkyl groups include bicyclo[2.2.1]hept-2-yl. Preferably, the cycloalkyl group is monocyclic.

As used herein, the term "halogen" means fluorine, chlorine, bromine or iodine. Fluorine, chlorine and bromine are particularly preferred.

As used herein, the term "haloalkyl" means an alkyl group having a halogen substituent, the terms "alkyl" and "halogen" being understood to have the meanings outlined above. Similarly, the term "dihaloalkyl" means an alkyl group having two halogen substituents and the term "trihaloalkyl" means an alkyl group having three halogen substituents. Examples of haloalkyl groups include fluoromethyl, chloromethyl, bromomethyl, fluoromethyl, fluoropropyl and fluorobutyl groups; examples of dihaloalkyl groups include difluoromethyl and difluoroethyl groups; examples of trihaloalkyl groups include trifluoromethyl and trifluoroethyl groups.

As used herein, the term "heterocyclyl" means an aromatic or a non-aromatic cyclic group of carbon atoms wherein from one to three of the carbon atoms is/are replaced by one or more heteroatoms independently selected from nitrogen, oxygen or sulfur. A heterocyclyl group may, for example, be monocyclic or bicyclic. In a bicyclic heterocyclyl group there may be one or more heteroatoms in each ring, or only in one of the rings. A heteroatom is preferably O or N. Heterocyclyl groups containing a suitable nitrogen atom include the corresponding N-oxides.

Examples of monocyclic non-aromatic heterocyclyl groups (also referred to as monocyclic heterocycloalkyl rings) include aziridinyl, azetidinyl, pyrrolidinyl, imidazolidinyl, pyrazolidinyl, piperidinyl, piperazinyl, tetrahydrofuranyl, tetrahydropyranyl, morpholinyl, thiomorpholinyl and azepanyl.

Examples of bicyclic heterocyclyl groups in which one of the rings is non-aromatic include dihydrobenzofuranyl, indanyl, indolinyl, isoindolinyl, tetrahydroisoquinolinyl, tetrahydroquinolyl and benzoazepanyl.

Examples of monocyclic aromatic heterocyclyl groups (also referred to as monocyclic heteroaryl groups) include furanyl, thienyl, pyrrolyl, oxazolyl, thiazolyl, imidazolyl, oxadiazolyl, thiadiazolyl, pyridyl, triazolyl, triazinyl, pyridazyl, isothiazolyl, isoxazolyl, pyrazinyl, pyrazolyl and pyrimidinyl, with preferred monocyclic aromatic heterocyclyl groups being furanyl, thienyl, pyrrolyl, oxazolyl, imidazolyl, oxadiazolyl, thiadiazolyl, pyridyl, triazolyl, triazinyl, pyridazyl, isothiazolyl, isoxazolyl, pyrazinyl, pyrazolyl and pyrimidinyl.

Examples of bicyclic aromatic heterocyclyl groups (also referred to as bicyclic heteroaryl groups) include quinoxalinyl, quinazolinyl, pyridopyrazinyl, benzoxazolyl, benzothiophenyl, benzimidazolyl, naphthyridinyl, quinolinyl, benzofuranyl, indolyl, benzothiazolyl, oxazolyl[4,5-b]pyridiyl, pyridopyrimidinyl, isoquinolinyl and benzodroxazole.

Examples of preferred heterocyclyl groups include piperidinyl, tetrahydrofuranyl, tetrahydropyranyl, pyridyl, pyrimidinyl and indolyl. Preferred heterocyclyl groups also include thienyl, thiazolyl, furanyl, pyrazolyl, pyrrolyl, isoxazolyl and imidazolyl.

As used herein the term "cycloalkylalkyl" means a group cycloalkyl-alkyl-attached through the alkyl group, "cycloalkyl" and "alkyl" being understood to have the meanings outlined above.

As mentioned above, the compounds of the invention have activity as estrogen receptor ligands. The compounds of the invention have activity as estrogen receptor modulators, and may be agonists, partial agonists, antagonists, or partial antagonists of the estrogen receptor. Particularly preferred compounds of the invention have activity as an agonist or a partial agonist of ERβ. Preferred compounds of this type are selective agonists of the estrogen receptor-beta (ERβ).

The compounds of the invention may thus be used in the treatment of diseases or disorders associated with estrogen receptor activity. In particular, the compounds of the invention that are agonists or partial agonists of the estrogen receptor may be used in the treatment of diseases or disorders for which selective agonists or partial agonists of the estrogen receptor are indicated. The compounds of the invention that are antagonists or partial antagonists of the estrogen receptor may be used in the treatment of diseases or disorders for which selective antagonists or partial antagonists of the estrogen receptor are indicated.

Clinical conditions for which an agonist or partial agonist is indicated include, but are not limited to, bone loss, bone fractures, osteoporosis, cartilage degeneration, endometriosis, uterine fibroid disease, hot flashes, increased levels of LDL cholesterol, cardiovascular disease, impairment of cognitive functioning, cerebral degenerative disorders, restenosis, gynecomastia, vascular smooth muscle cell proliferation, obesity, incontinence, anxiety, depression, autoimmune disease, inflammation, IBD, IBS, sexual dysfunction, hypertension, retinal degeneration, and lung, colon, breast, uterus, and prostate cancer, lymphoma, and/or disorders related to estrogen functioning.

The compounds of the invention find particular application in the treatment or prophylaxis of the following: bone loss, bone fractures, osteoporosis, cartilage degeneration, endometriosis, uterine fibroid disease, hot flushes, increased levels of LDL cholesterol, cardiovascular disease, impairment of cognitive functioning, age-related mild cognitive impairment, cerebral degenerative disorders, restenosis, gynecomastia, vascular smooth muscle cell proliferation, obesity, incontinence, anxiety, depression, perimenopausal depression, post-partum depression, premenstrual syndrome, manic depression, dementia, obsessive compulsive behavior, attention deficit disorder, attention deficit hyperactivity disorder, sleep disorders, irritability, impulsivity, anger management, hearing disorders, multiple sclerosis, Parkinson's disease, Alzheimer's disease, Huntington's disease, amyotrophic lateral sclerosis, spinal cord injury, stroke, autoimmune disease, inflammation, IBD, IBS, sexual dysfunction, hypertension, retinal degeneration, lung cancer, colon cancer, breast cancer, uterus cancer, prostate cancer, and the bile duct cancer form named cholangiocarcinoma. The compounds of the invention also find particular application in the treatment or prophylaxis of the following: benign prostatic hyperplasia, lower urinary tract symptoms, overactive bladder, interstitial cystitis, painful bladder symptoms, vaginal atrophy, wound healing, chronic pain, sepsis, inflammatory and neuropathic pain, ovarian cancer, melanoma, and lymphoma (B-cell lymphoma, T-cell lymphoma).

In combination with drugs that are known to induce vasomotor symptoms, the compounds of the invention find utility as follows: in combination with SERMs such as tamoxifen, in its use for the treatment of breast cancer, and raloxifene, used for the treatment and/or prevention of osteoporosis, to alleviate SERM-induced vasomotor symptoms; in combination with an aromatase inhibitor, used for the treatment of breast cancer or endometriosis, to alleviate aromatase inhibitor-induced vasomotor symptoms; and in male prostate cancer patients that have undergone androgen deprivation therapy.

In one embodiment of the invention, the present compounds finds particular application in the treatment or prophylaxis of depression, perimenopausal depression, post-partum depression, premenstrual syndrome and manic depression.

The treatment or prophylaxis of hot flashes (or hot flushes) in males, is preferable for patients that have had an androgen ablation for treatment of prostate cancer.

The phrase "depression" includes but is not limited to, major depressive disorder, dysthymic disorder, bipolar disorder, cyclothymic disorder, mood disorder due to a general medical condition, substance-induced mood misorder, seasonal affective disorder (SAD), postpartum depression and premenstrual dysphoric disorder.

The invention also provides a method for the treatment or prophylaxis of a condition in a mammal mediated by an estrogen receptor, which comprises administering to the mammal a therapeutically effective amount of a compound according to the invention. Clinical conditions mediated by an estrogen receptor that may be treated by the method of the invention are preferably those described above.

The invention also provides the use of a compound according to the invention, for the manufacture of a medicament for the treatment or prophylaxis of a condition mediated by an estrogen receptor. Clinical conditions mediated by an estrogen receptor that may be treated by the method of the invention are preferably those described above.

The amount of active ingredient which is required to achieve a therapeutic effect will, of course, vary with the particular compound, the route of administration, the subject under treatment, including the type, species, age, weight, sex, and medical condition of the subject and the renal and hepatic function of the subject, and the particular disorder or disease being treated, as well as its severity. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day, for adult humans. For oral administration, the compositions are preferably provided in the form of tablets or other forms of presentation provided in discrete units containing 0.01, 0.05, 0.1, 0.5, 1.0, 2.5, 5.0, 10.0, 15.0, 25.0, 50.0, 100, and 500 milligrams of the active ingredient for the symptomatic adjustment of the dosage to the patient to be treated. A medicament typically contains from about 0.01 mg to about 500 mg of the active ingredient, preferably from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

While it is possible for the active ingredient to be administered alone, it is preferable for it to be present in a pharmaceutical formulation or composition. Accordingly, the invention provides a pharmaceutical formulation comprising a compound according to the invention, and a pharmaceutically acceptable diluent, excipient or carrier (collectively referred to herein as "carrier" materials). Pharmaceutical compositions of the invention may take the form of a pharmaceutical formulation as described below.

The pharmaceutical formulations according to the invention include those suitable for oral, parenteral (including subcutaneous, intradermal, intramuscular, intravenous [bolus or infusion], and intraarticular), inhalation (including fine particle dusts or mists which may be generated by means of various types of metered does pressurized aerosols), nebulizers or insufflators, rectal, intraperitoneal and topical (including dermal, buccal, sublingual, and intraocular) administration, although the most suitable route may depend upon, for example, the condition and disorder of the recipient.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets, pills or tablets each containing a predetermined amount of the active ingredient; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate, calcium sulfate, sorbitol, glucose and/or lactose and/or other excipients, binders, extenders, disintegrants, diluents and lubricants such as those known in the art. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Disintegrators include without limitation starch, methylcellulose, agar, bentonite, xanthan gum and the like. The compounds of formula (I) can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use. Lubricants used in these dosage forms include sodium oleate, sodium stearate, magnesium stearate, sodium benzoate, sodium acetate, sodium chloride and the like. For oral administration in liquid form, the oral drug components can be combined with any oral, non-toxic, pharmaceutically acceptable inert carrier such as ethanol, glycerol, water, and the like.

The compounds of the present invention can also be administered in the form of liposome delivery systems, such as small unilamellar vesicles, large unilamellar vesicles and multilamellar vesicles.

Liposomes can be formed from a variety of phospholipids, 1,2-dipalmitoylphosphatidylcholine, phosphatidyl ethanolamine (cephaline), or phosphatidylcholine (lecithin).

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Formulations for rectal administration may be presented as a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

Whilst a compound of the invention may be used as the sole active ingredient in a medicament, it is also possible for the compound to be used in combination with one or more further active agents. Such further active agents may be further compounds according to the invention, or they may be different therapeutic agents, for example an antidepressant, an anxiolytic, an anti-psychotic, an agent useful in the prevention or treatment of osteoporosis, an agent useful in the prevention or treatment of cancer or other pharmaceutically active material. For example, the compounds of the instant invention may be effectively administered in combination with effective amounts of other agents such as an antidepressant, an anxiolytic, an anti-psychotic, an organic bisphosphonate or a cathepsin K inhibitor. In one preferred embodiment, the compounds of the invention may be effectively administered in combination with an effective amount of an antidepressant. Nonlimiting examples of antidepressants include noradrenaline reuptake inhibitors (NRI), selective serotonin reuptake inhibitors, monoamine oxidase inhibitors, tricyclic antidepressants (TCA), dopamine reuptake inhibitors (DRI), opioids, selective seretonic reuptake enhancers, tetracyclic antidepressants, reversible inhibitors of monoamine oxidase, melatonin agonists, serotonin and noradrenaline reuptake inhibitors (SNRI), corticotropin releasing factor antagonists, $\alpha$-adrenoreceptor antagonists, 5HT1$\alpha$ receptor agonists and antagonists, lithium and atypical anti-psychotics. Examples of antidepressants of the SSRI class include Fluoxetine and Sertraline; examples of antidepressants of the SNRI class Venlafaxine, Citalopram, Paroxetine, Escitalopram, Fluvoxamine; examples of antidepressants of the SNRI class include Duloxetine; examples of antidepressants of the DRI and NRI classes include Bupropion; examples of antidepressants of the TCA class include Amitriptyline and Dothiepin (Dosulepin). Examples of atypical antipsychotics include: Clozapine, Olanzapine, Risperidone, Quetiapine, Ziprasidone and Dopamine partial agonists. Nonlimiting examples of anxiolytics include benzodiazepines and non-benzodiazapines. Examples of benzodiazapines include lorazepam, alprazolam, and diazepam. Examples of non-benzodiazapines include Buspirone (Buspar®), barbiturates and meprobamate. One or more of those further anti-depressants may be used in combination.

Examples of anti-cancer agents include tamoxifene or an aromatase inhibitor, used in treatment of breast cancer.

In the event that hot flashes are induced by a particular treatment, a compound of the invention may be used in combination therapy with the agent of such treatment. Nonlimiting examples of such combination treatment therapies include: a compound of the invention in combination with tamoxifene treatment of breast cancer, a compound of the invention in combination with aromatase inhibitor treatment of breast cancer or a compound of the invention in combination with raloxifene treatment of osteoporosis.

Nonlimiting examples of above-mentioned organic bisphosphonates include adendronate, clodronate, etidronate, ibandronate, incadronate, minodronate, neridronate, risedronate, piridronate, pamidronate, tiludronate, zoledronate, pharmaceutically acceptable salts or esters thereof, and mixtures thereof. Preferred organic biphosphonates include alendronate and pharmaceutically acceptable salts and mixtures thereof. Most preferred is alendronate monosodium trihydrate.

The precise dosage of the bisphosphonate will vary with the dosing schedule, the oral potency of the particular bisphosphonate chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. An appropriate amount can be determined by routine experimentation from animal models and human clinical studies. Generally, an appropriate amount of bisphosphonate is chosen to obtain a bone resorption inhibiting effect, i.e. a bone resorption inhibiting amount of the bisphosphonate is administered. For humans, an effective oral dose of bisphosphonate is typically from about 1.5 to about 6000 μg/kg of body weight and preferably about 10 to about 2000 μg/kg of body weight.

For human oral compositions comprising alendronate, pharmaceutically acceptable salts thereof, or pharmaceutically acceptable derivatives thereof, a unit dosage typically comprises from about 8.75 mg to about 140 mg of the alendronate compound, on an alendronic acid active weight basis, i.e. on the basis of the corresponding acid.

The compounds of the present invention can be used in combination with other agents useful for treating estrogen-mediated conditions. The individual components of such combinations can be administered separately at different times during the course of therapy or concurrently in divided or single combination forms. The present invention is therefore to be understood as embracing all such regimes of simultaneous or alternating treatment and the term "administering" is to be interpreted accordingly. It will be understood that the scope of combinations of the compounds of this invention with other agents useful for treating estrogen-mediated conditions includes in principle any combination with any pharmaceutical composition useful for treating disorders related to estrogen functioning.

The above other therapeutic agents, when employed in combination with the compounds of the present invention, may be used, for example, in those amounts indicated in the Physicians' Desk Reference (PDR) or as otherwise determined by one of ordinary skill in the art.

Where the compounds of the invention are utilized in combination with one or more other therapeutic agent(s), either concurrently or sequentially, the following combination ratios and dosage ranges are preferred:

When combined with an antidepressant, an anxiolytic, an anti-psychotic, an organic bisphosphonate or a cathepsin K inhibitor, the compounds of formula (I) may be employed in a weight ratio to the additional agent within the range from about 10:1 to about 1:10.

The compounds of the invention as described above also find use, optionally in labelled form, as a diagnostic agent for the diagnosis of conditions associated with malfunction of the estrogen receptor. For example, such a compound may be radioactively labelled.

The compounds of the invention as described above, optionally in labelled form, also find use as a reference compound in methods of discovering other agonists, partial agonists, antagonists or partial antagonists of the estrogen receptor. Thus, the invention provides a method of discovering a ligand of the estrogen receptor which comprises use of a compound of the invention or a compound of the invention in labelled form, as a reference compound. For example, such a method may involve a competitive binding experiment in which binding of a compound of the invention to the estrogen receptor is reduced by the presence of a further compound which has estrogen receptor-binding characteristics, for example stronger estrogen receptor-binding characteristics than the compound of the invention in question.

Numerous synthetic routes to the compounds of the present invention can be devised by any person skilled in the art and the possible synthetic routes described below do not limit the invention. Many methods exist in the literature for the synthesis of pyrazoles, for example: *Heterocyclic Chemistry*, Joule, J. A.; Mills, K. 2000. A number of possible synthetic routes are shown schematically below. Where appropriate, any initially produced compound according to the invention can be converted into another compound according to the invention by known methods.

General Method I

The following general method can be used to prepare compounds of formula (I) wherein G represents

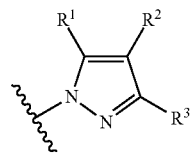

and $R^2$ is cyano, —CH=N—OH, —C(O)NH$_2$, or —C(NH$_2$)=N—OH.

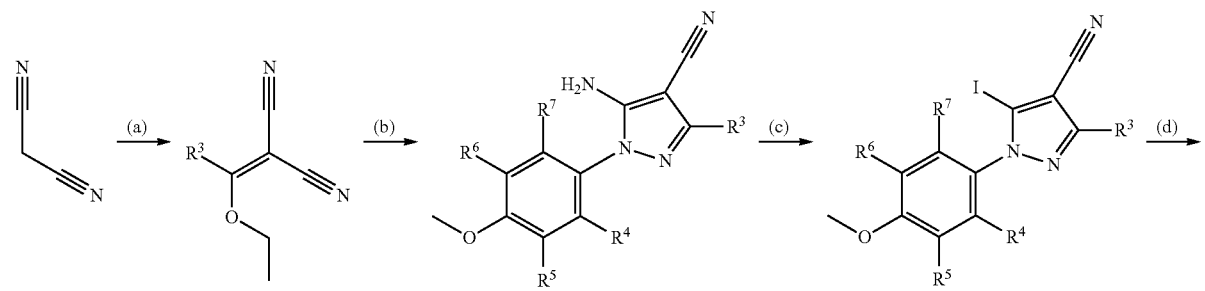

-continued

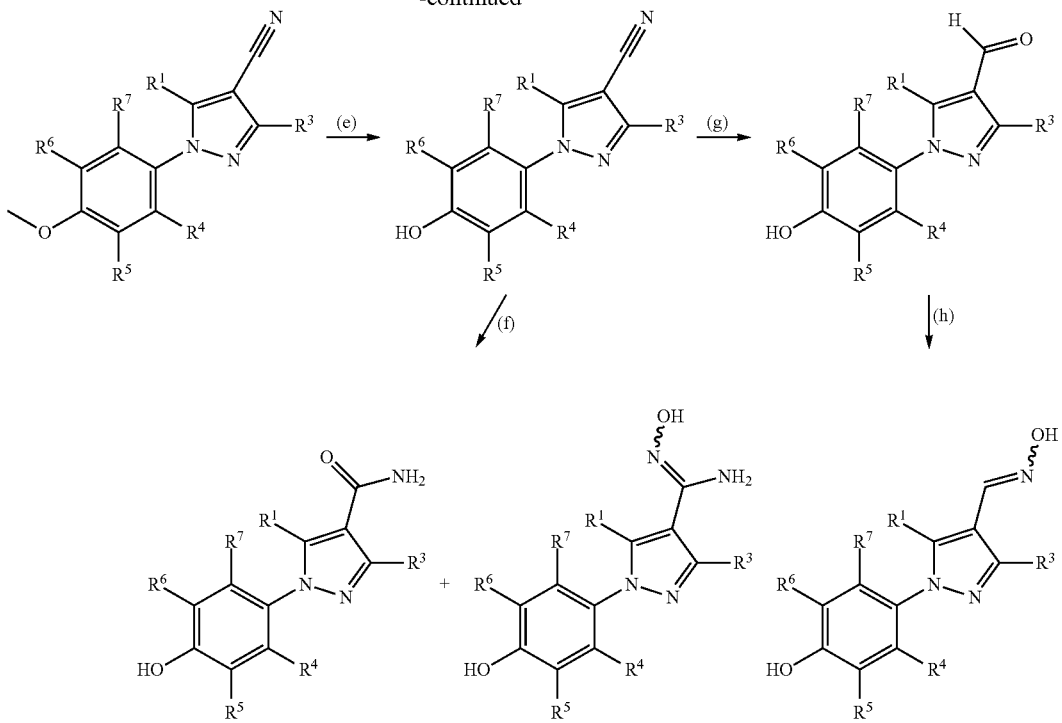

(a) 1,1,1-triethoxyalkane, Ac$_2$O; (b) (4-methoxyphenyl)hydrazine (EtOH); (c) isoamyl nitrite, diiodomethane (MeCN); (d) PdCl$_2$(PPh$_3$)$_2$, R$^1$SnBu$_3$ (DME/dioxane); (e) BBr$_3$ (CH$_2$Cl$_2$); (f) NH$_2$OH (MeOH/water); (g) DIBAL—H (CH$_2$Cl$_2$); (h) NH$_2$OH*HCl, py (EtOH)

General Method I as shown in the reaction scheme above was used for the synthesis of the following Examples: 1-3, 17-37, 39, 54 and 55. Full experimental details of the individual steps of the general method applicable for the synthesis of the final compounds of those Examples are described in Examples 1, 2, 3, 4 and 5.

General Method II

The following general method can be used to prepare compounds of formula (I) wherein G represents

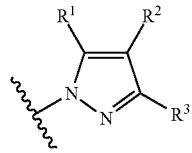

and R$^2$ is cyano, —CH=N—OH or —C(NH$_2$)=N—OH.

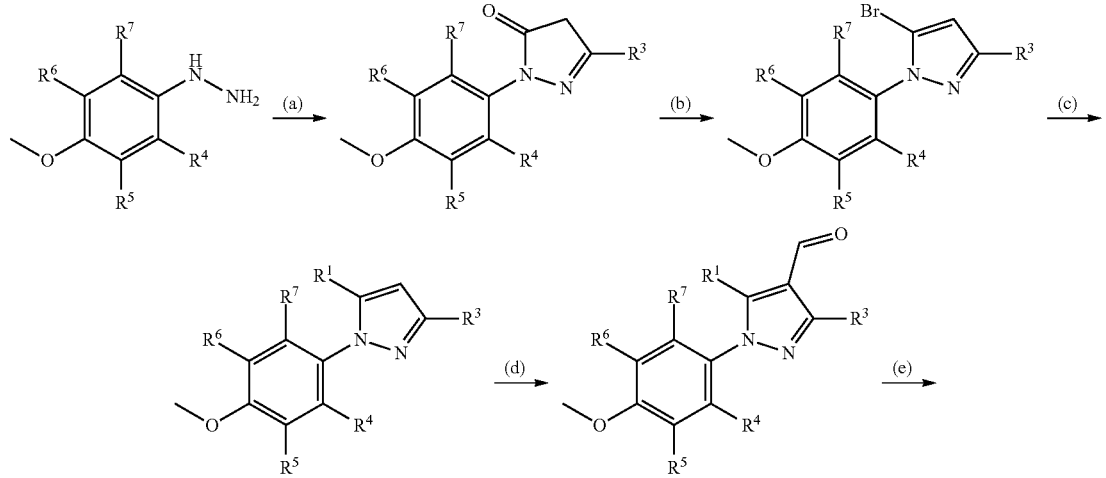

-continued

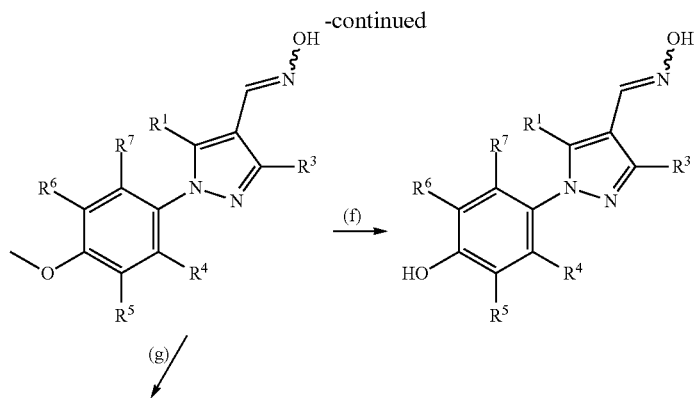

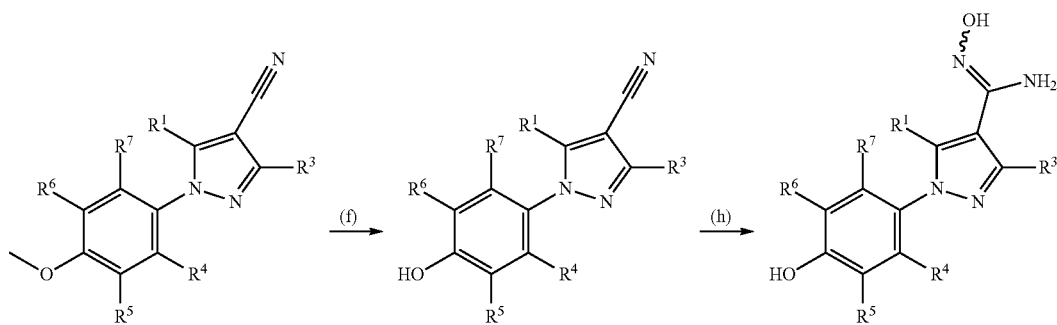

(a) R³C(O)CH₂CO₂Et, AcOH, Et₃N; (b) PBr₃ (MeCN); (c) Pd(PPh₃)₄, R¹B(OH)₂, K₂CO₃, NaI (dioxane/water); (d) POCl₃, DMF (toluene); (e) NH₂OH*HCl, pyridine (EtOH
(f) BBr₃ (DCM); (g) Ac₂O; (h) NH₂OH (DMSO/water)

General Method II as shown in the reaction scheme above was used for the synthesis of examples 4 and 5. Full experimental details of the individual steps of the general method applicable for the synthesis of the final compounds of those Examples are described in Examples 4 and 5.

General Method III

The following general method can be used to prepare compounds of formula (I) wherein G represents

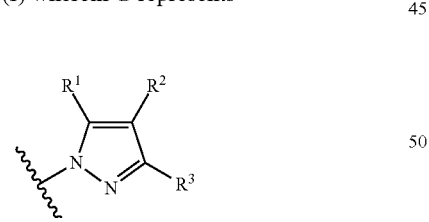

R¹ is a pyrrolyl group attached through its nitrogen, and R² is cyano or —C(NH₂)=N—OH.

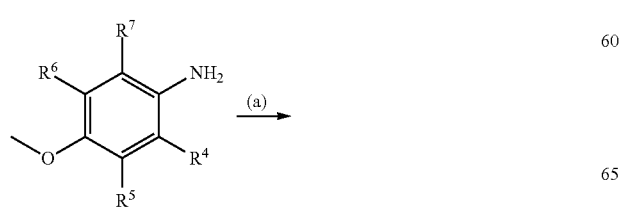

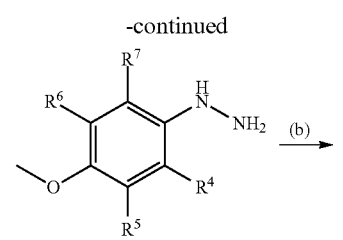

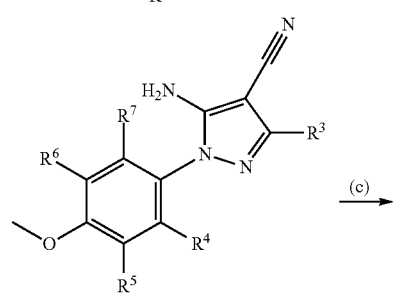

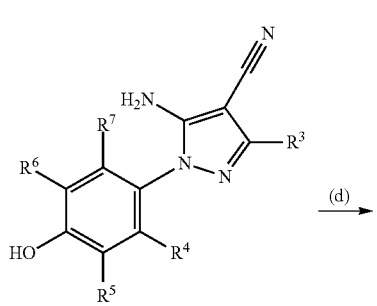

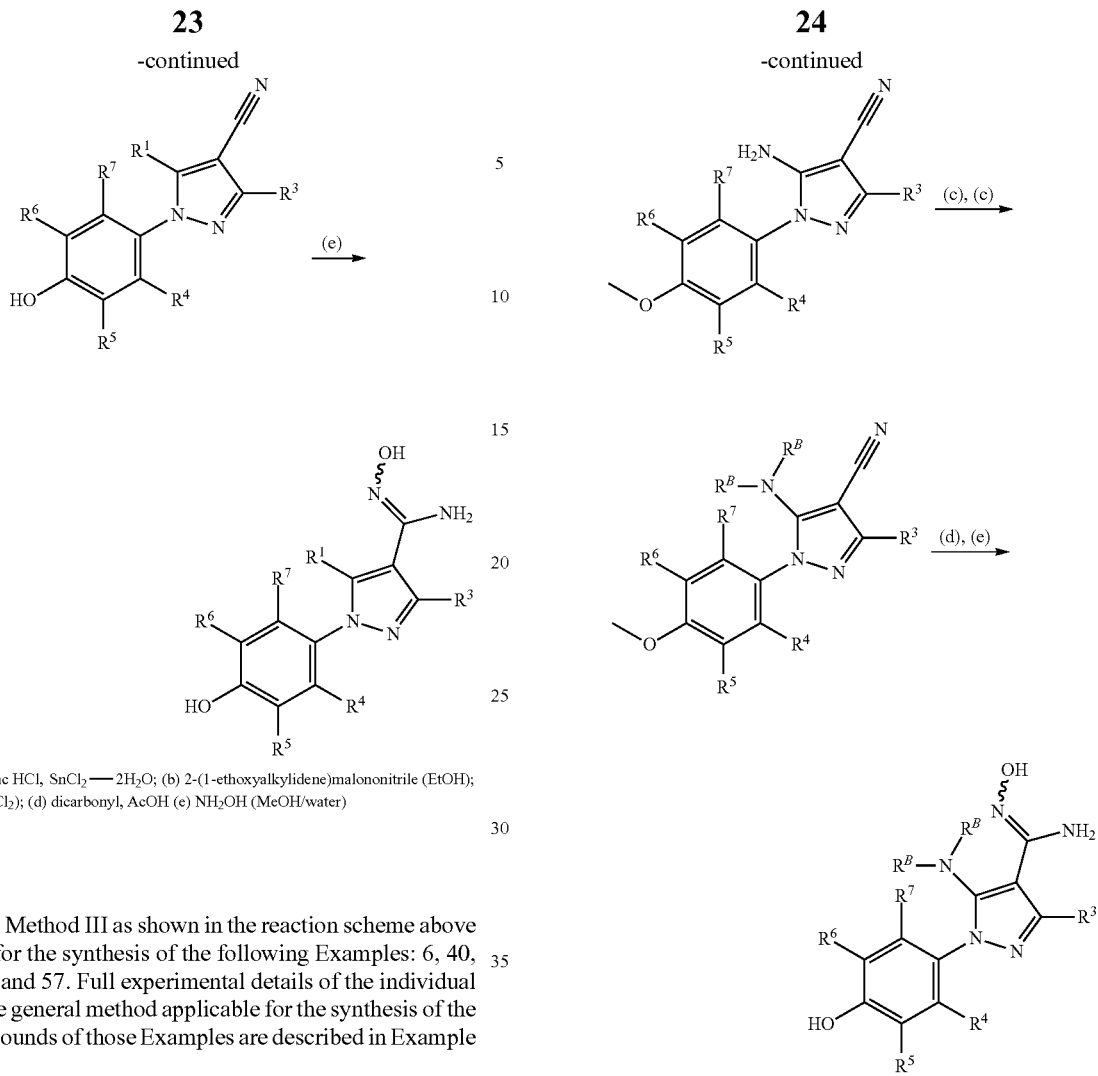

(a) NaNO₂, conc HCl, SnCl₂—2H₂O; (b) 2-(1-ethoxyalkylidene)malononitrile (EtOH); (c) BBr₃ (CH₂Cl₂); (d) dicarbonyl, AcOH (e) NH₂OH (MeOH/water)

General Method III as shown in the reaction scheme above was used for the synthesis of the following Examples: 6, 40, 41, 42, 56 and 57. Full experimental details of the individual steps of the general method applicable for the synthesis of the final compounds of those Examples are described in Example 6.

General Method IV

The following general method can be used to prepare compounds of formula (I) wherein G represents

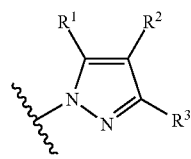

R¹ is an N(R$^B$)₂ group, and R² is —C(NH₂)=N—OH.

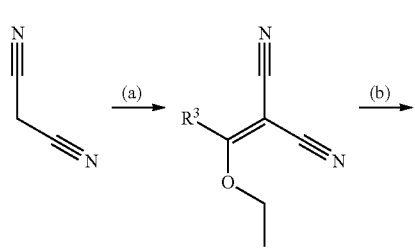

(a) 1,1,1-triethoxyalkane, Ac₂O; (b) (4-methoxyphenyl)hydrazine (EtOH); (c) LDA, R$^B$Br (THF); (d) BBr₃ (CH₂Cl₂); (e) NH₂OH (MeOH/water)

General Method IV as shown in the reaction scheme above was used for the synthesis Example 7: Full experimental details of the individual steps of the general method applicable for the synthesis of the final compounds of those Examples are described in Example 7.

General Method V

The following general method can be used to prepare compounds of formula (I) wherein G represents

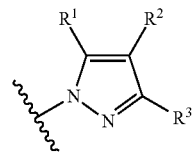

R¹ is a pyrrolyl group attached through a carbon, and R² is cyano or —C(NH₂)=N—OH.

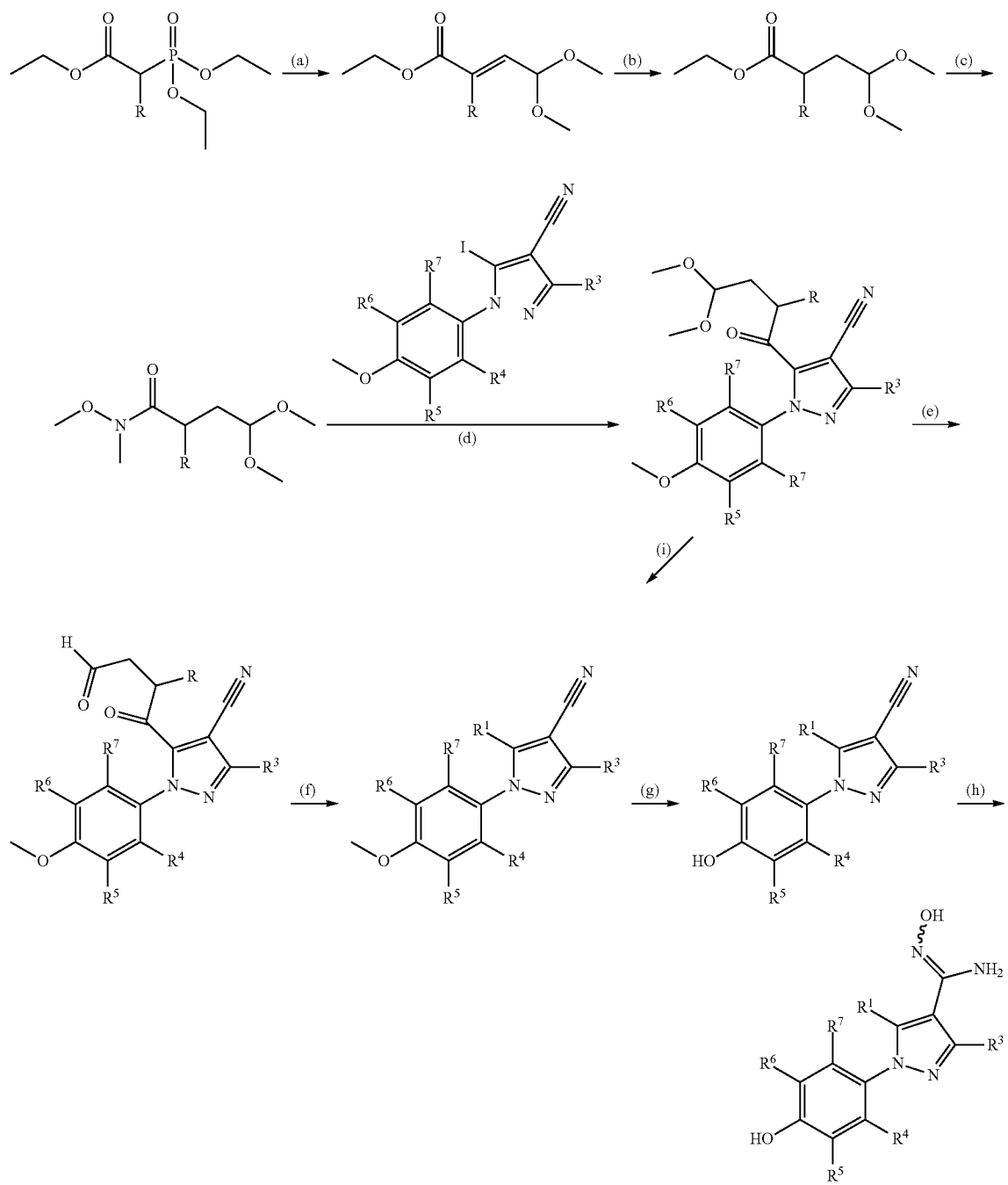

(a) 2,2-dimethoxy acetaldehyde, K$_2$CO$_3$ (heptane); (b) PtO$_2$, H$_2$ (EtOAc); (c) N,O-dimethylamine hydrochloride, isopropyl magnesium chloride (THF); (d) n-BuLi (Et$_2$O); (e) TFA, H$_2$O (CHCl$_3$); (f) RNH$_2$ (CH$_2$Cl$_2$); (g) BBr$_3$ (CH$_2$Cl$_2$); (h) NH$_2$OH (MeOH); (i) RNH$_2$, HCl$_{conc.}$ (MeOH).

General Method V as shown in the reaction scheme above was used for the synthesis of the following Examples: 8, 9, 10, 43, 44 and 45. Full experimental details of the individual steps of the general method applicable for the synthesis of the final compounds of those Examples are described in Examples 8, 9 and 10.

General Method VI

The following general method can be used to prepare compounds of formula (I) wherein G represents

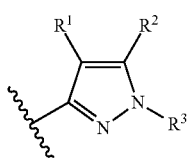

and R$^2$ is cyano, C$_{1-6}$alkyl-OH, —CH=N—OH, —C(O)NH$_2$, or —C(NH$_2$)=N—OH.

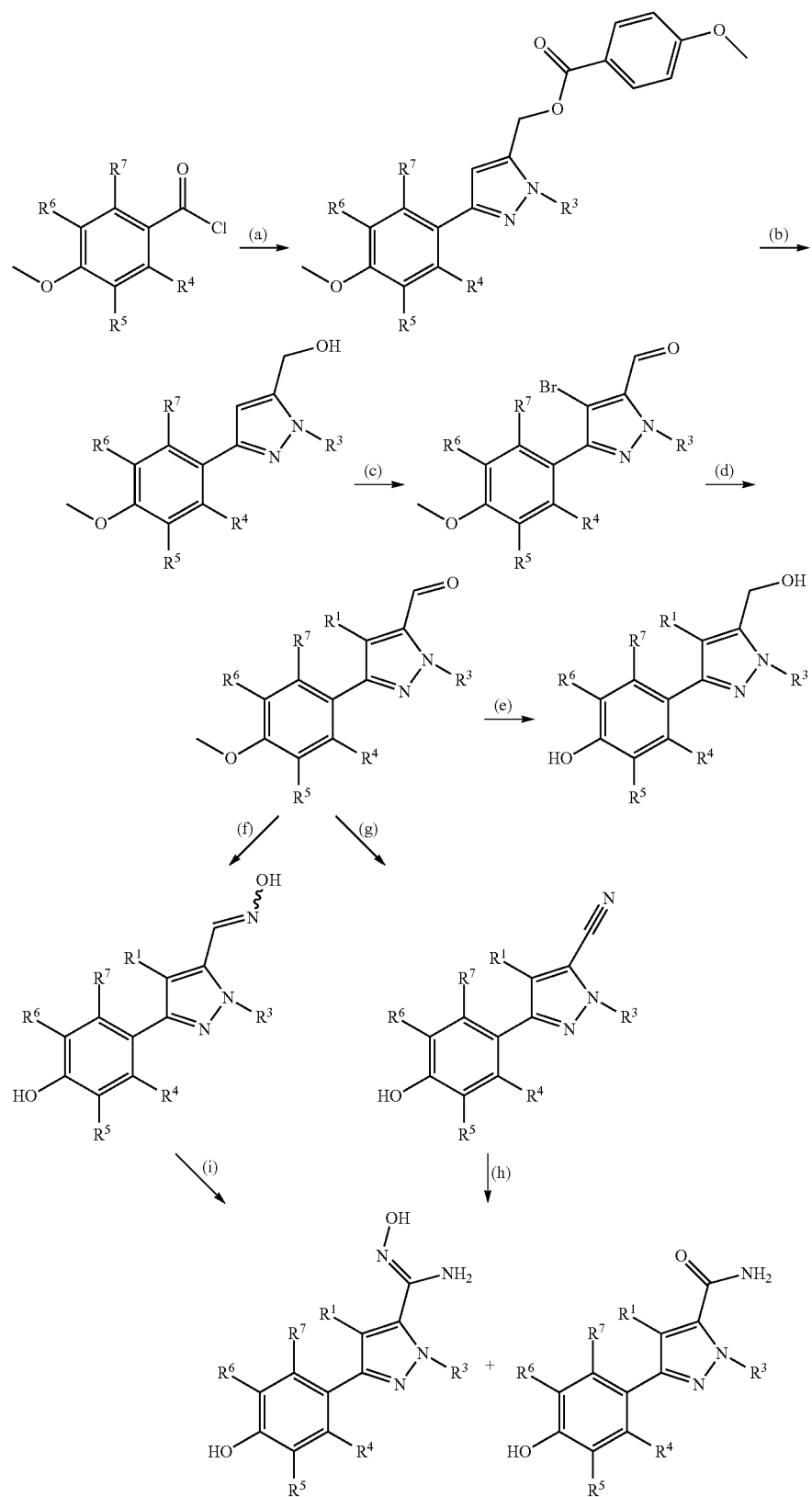
(a) 1) prop-2-yn-1-ol, PdCl$_2$(PPh$_3$)$_2$, CuI, TEA, 2) MeOH, AcOH R$^3$NHNH$_2$; (b) LiBH$_4$ (EtOAc); (c) 1) NBS (MeCN) 2) Dess-Martin-periodinane; (d) R$^1$B(OH)$_2$, Pd(PPh$_3$)$_4$ K$_2$CO$_3$, (DME/H$_2$O); (e) 1) LiBH$_4$ (Et$_2$O), 2) BF$_3$*Me$_2$S (DCM); (f) 1) NH$_2$OH•HCl, pyridine (EtOH), 2) BF$_3$*Me$_2$S (DCM); (g) 1) NH$_2$OH•HCl, pyridine (EtOH), 2) SOCl$_2$, 3) BF$_3$*Me$_2$S (DCM); (h) NH$_2$OH (DMSO/water); (i) 1) Ac$_2$O, 2) NH$_2$OH (DMSO/water)

General Method VI as shown in the reaction scheme above was used for the synthesis of the following Examples: 11, 12, 13, 14, 16, 46, 47, 48, 49, 50, 59, 60, 61, 63, 64 and 65. Full experimental details of the individual steps of the general method applicable for the synthesis of the final compounds of those Examples are described in Examples 11, 12, 13, 14 and 16.

General Method VII

The following general method can be used to prepare compounds of formula (I) wherein G represents

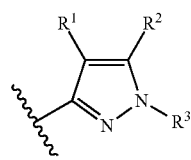

and $R^2$ is $C_{1-6}$alkyl-OH.

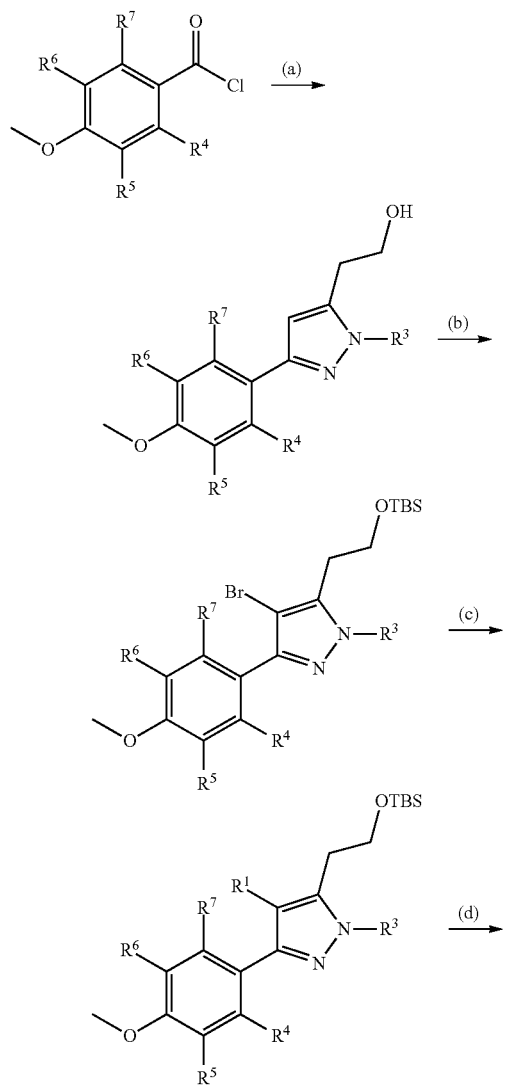

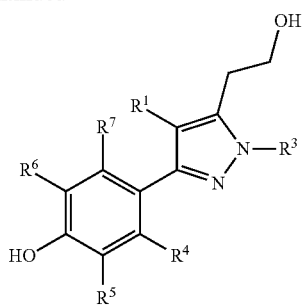

(a) 1) but-3-yn-1-ol, PdCl$_2$(PPh$_3$)$_2$, CuI, TEA, 2) AcOH, R$^3$NHNH$_2$ (MeOH);
(b) 1) NBS (MeCN), 2) TBSOTf, TEA (DCM); (c) R$^1$B(OH)$_2$, Pd(PPh$_3$)$_4$, K$_2$CO$_3$ (DME/water); (d) BF$_3$*Me$_2$S (DCM)

General Method VII as shown in the reaction scheme above was used for the synthesis of Example 15. Full experimental details of the individual steps of the general method applicable for the synthesis of the final compounds of those Examples are described in Example 15.

General Method VIII

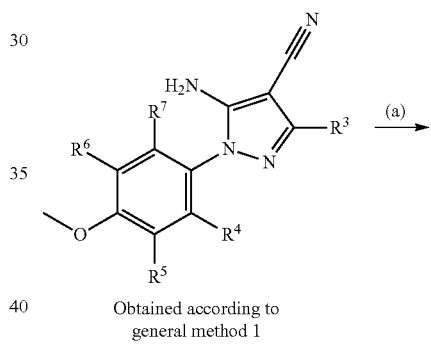

Obtained according to general method 1

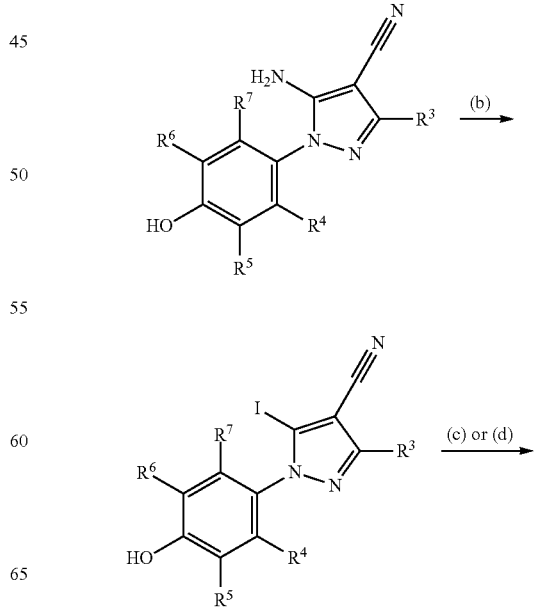

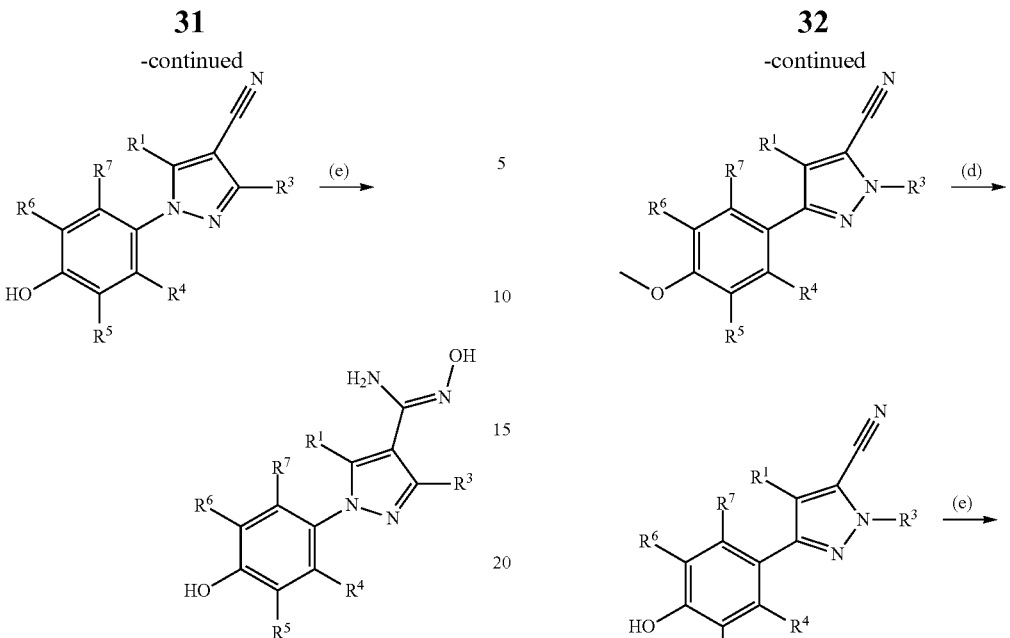

(a) BBr₃ (CH₂Cl₂); (b) isoamyl nitrite, diiodomethane (MeCN); (c) Pd(PPh₃)₄, R₁B(OH)₂, K₂CO₃ (DME/H₂O); (d) PdCl₂(PPh₃)₂, R₁SnBu₃ (DME/dioxane); (e) NH₂OH (MeOH/water)

General Method VIII as shown in the reaction scheme above was used for the synthesis of Examples 51, 52 and 53. Full experimental details of the individual steps of the general method applicable for the synthesis of the final compounds of those Examples are described in Examples 51 and 52.

General Method IX

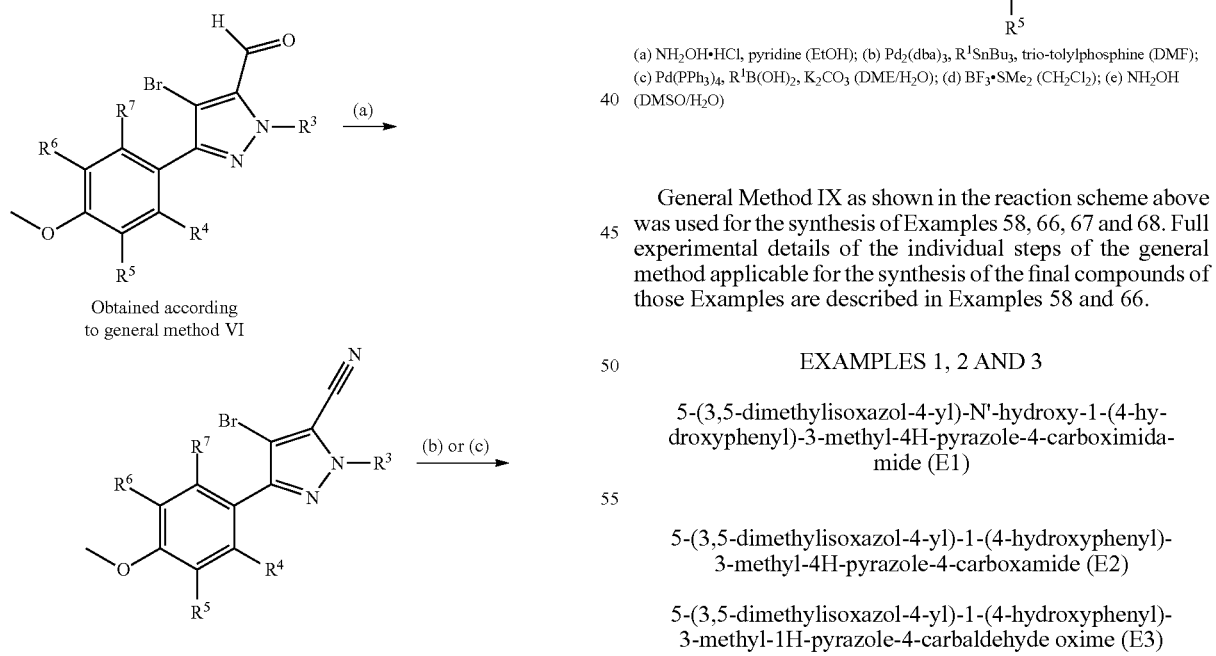

Obtained according to general method VI (a) NH₂OH·HCl, pyridine (EtOH); (b) Pd₂(dba)₃, R¹SnBu₃, trio-tolylphosphine (DMF); (c) Pd(PPh₃)₄, R¹B(OH)₂, K₂CO₃ (DME/H₂O); (d) BF₃·SMe₂ (CH₂Cl₂); (e) NH₂OH (DMSO/H₂O)

General Method IX as shown in the reaction scheme above was used for the synthesis of Examples 58, 66, 67 and 68. Full experimental details of the individual steps of the general method applicable for the synthesis of the final compounds of those Examples are described in Examples 58 and 66.

EXAMPLES 1, 2 AND 3

5-(3,5-dimethylisoxazol-4-yl)-N'-hydroxy-1-(4-hydroxyphenyl)-3-methyl-4H-pyrazole-4-carboximidamide (E1)

5-(3,5-dimethylisoxazol-4-yl)-1-(4-hydroxyphenyl)-3-methyl-4H-pyrazole-4-carboxamide (E2)

5-(3,5-dimethylisoxazol-4-yl)-1-(4-hydroxyphenyl)-3-methyl-1H-pyrazole-4-carbaldehyde oxime (E3)

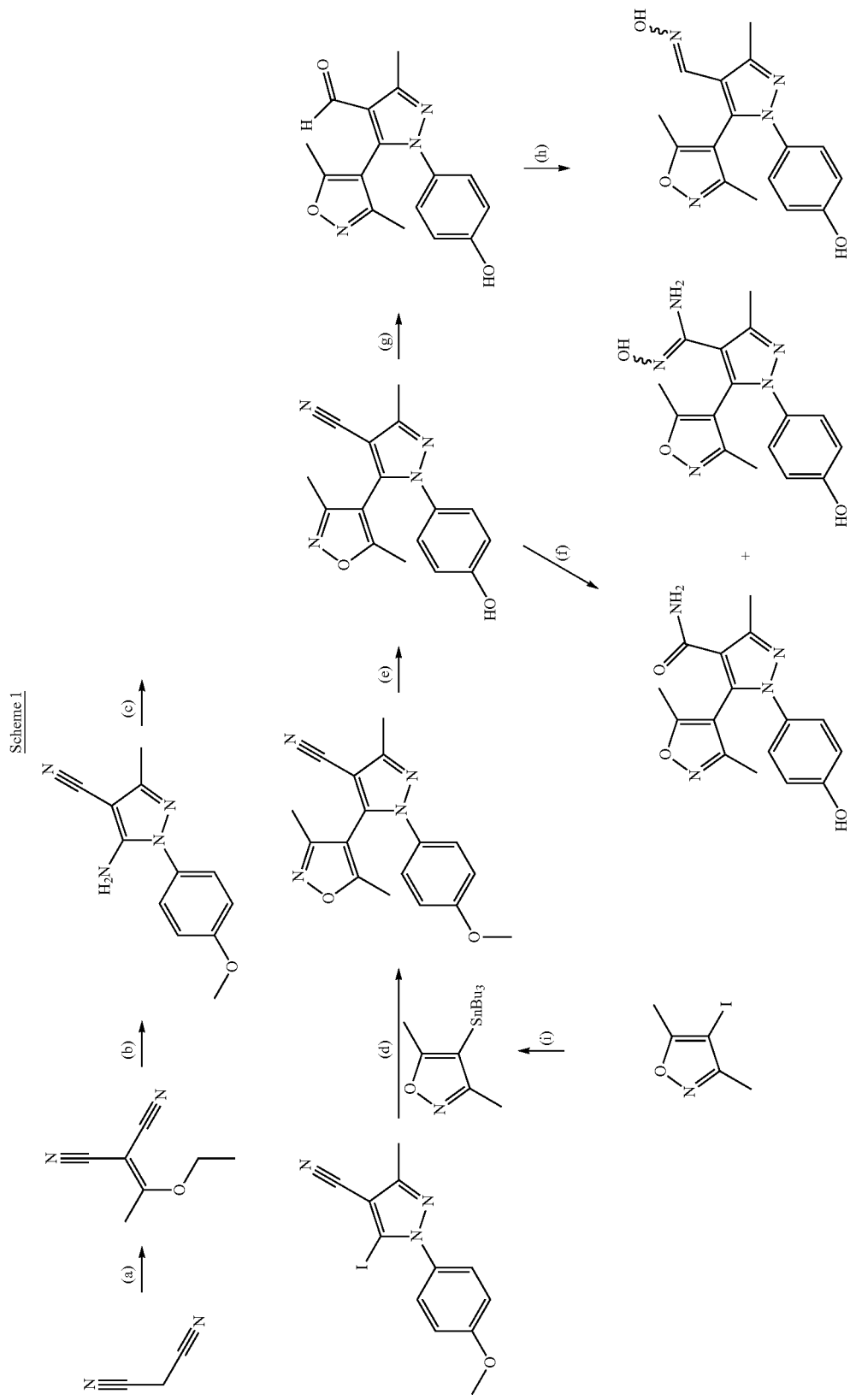

Step (a): To a stirred solution of malononitrile (2.64 g, 40.0 mmol) in acetic anhydride (9 mL) was added 1,1,1-triethoxyethane (6.48 g, 40.0 mmol). The solution was stirred for 15 h at reflux, cooled, and poured into water. The mixture was extracted with ether, and the organic extract was washed with aqueous NaHCO$_3$ and then brine. The solution was dried (MgSO$_4$) and concentrated under reduced pressure to afford a solid identified as 2-(1-ethoxyethylidene)malononitrile (4.35 g, 80%). The procedure was adapted from *J. Med. Chem.* 2004, 47, 5894-5911.

Step (b): To a stirred solution of 2-(1-ethoxyethylidene)malononitrile (958 mg, 7.04 mmol) in EtOH (12 mL) was added (4-methoxyphenyl)hydrazine (1.12 g, 8.09 mmol). (Prior to using the hydrazine its HCl salt was washed with NaHCO$_3$/CH$_2$Cl$_2$. The organic phase was concentrated and used directly.) The solution was heated to 105° C. in the microwave for 20 minutes. CH$_2$Cl$_2$ was added and the organic phase was washed with 1 M HCl and the organic extract was washed with aqueous NaHCO$_3$. The solution was dried using a phase separator and concentrated under reduced pressure to give 5-amino-1-(4-methoxyphenyl)-3-methyl-1H-pyrazole-4-carbonitrile (1.30 g, 81%) which was used as such in the next step. The procedure was adapted from *J. Med. Chem.* 2004, 47, 5894-5911.

Step (c): To a stirred solution of 5-amino-1-(4-methoxyphenyl)-3-methyl-1H-pyrazole-4-carbonitrile (1.30 g, 5.70 mmol) in MeCN (8 mL) was added diiodomethane (1.93 mL, 23.9 mmol) followed by isoamyl nitrite (0.19 mL, 1.42 mmol). The reaction vessel was heated using a heating gun to initiate the reaction. After the rest of isoamyl nitrite (1.72 mL, 12.8 mmol) was added and the reaction was stirred for 1 hour at 50° C. The reaction was concentrated into silica and purified using silica gel (Heptane-CH$_2$Cl$_2$ 1:0 to 0:1) gave 5-iodo-1-(4-methoxyphenyl)-3-methyl-1H-pyrazole-4-carbonitrile (1.45 g, 75%).

Step (d): 5-iodo-1-(4-methoxyphenyl)-3-methyl-1H-pyrazole-4-carbonitrile (450 mg, 1.33 mmol), 3,5-dimethyl-4-(tributylstannyl)isoxazole (907 mg, 2.35 mmol) and PdCl$_2$(PPh$_3$)$_2$ (186 mg, 0.27 mmol), were mixed with 1 mL degassed dioxane and 1 mL degassed DME under nitrogen in a microwave vial. The reaction was run at 145° C. in the microwave for 30 min. Water was added, extracted with CH$_2$Cl$_2$, filtered through a phase separator. The organic phase was evaporated and the residue was purified using silica to give 5-(3,5-dimethylisoxazol-4-yl)-1-(4-methoxyphenyl)-3-methyl-1H-pyrazole-4-carbonitrile (555 mg, >100%) which was used as such in the next step.

Step (e): 5-(3,5-dimethylisoxazol-4-yl)-1-(4-methoxyphenyl)-3-methyl-1H-pyrazole-4-carbonitrile (555 mg, 1.33 mmol) was dissolved in CH$_2$Cl$_2$ (50 mL) and BBr$_3$ (1 M solution in DCM, 7 mL, 7.0 mmol) was added. The reaction was stirred over night at room temperature. Water was added and the product was extracted with CH$_2$Cl$_2$. Filtration through a phase separator, concentration and purification using silica gave 5-(3,5-dimethylisoxazol-4-yl)-1-(4-methoxyphenyl)-3-methyl-1H-pyrazole-4-carbonitrile (303 mg, 78%).

Step (f): A hydroxylamine solution was prepared. Hydroxylamine-HCl (26 mg, 0.37 mmol) and NaHCO$_3$ (32 mg, 0.37 mmol) dissolved in water (0.2 mL), methanol (0.4 mL) was stirred 2 min until gas ceased to evolve, the mixture was filtered and degassed (N$_2$). This was added to the 5-(3,5-dimethylisoxazol-4-yl)-1-(4-methoxyphenyl)-3-methyl-1H-pyrazole-4-carbonitrile (11 mg, 0.037 mmol) and stirred at 130° C. for 30 min in the microwave. EtOAc and brine were added and the phases were separated. Purification using preparative HPLC gave E1 5-(3,5-dimethylisoxazol-4-yl)-N'-hydroxy-1-(4-hydroxyphenyl)-3-methyl-1H-pyrazole-4-carboximidamide (2.52 mg, 7.71 µmol, 21%) ES/MS m/z: 328.19 (M+H), 326.22 (M−H); $^1$H NMR (acetone-d6, 500 MHz): 7.10 m 2H; 6.84 m 2H, 2.36 s 3H, 2.10 s 3H, 1.89 s 3H. Starting material 5-(3,5-dimethylisoxazol-4-yl)-1-(4-hydroxyphenyl)-3-methyl-1H-pyrazole-4-carbonitrile was recovered (0.99 mg, 3.36 µmol) as well as E2 5-(3,5-dimethylisoxazol-4-yl)-1-(4-hydroxyphenyl)-3-methyl-1H-pyrazole-4-carboxamide (3.22 mg, 0.01 mmol) ES/MS m/z: 313.17 (M+H), 311.22 (M−H); $^1$H NMR (acetone-d6, 500 MHz): 7.10 m 2H, 6.85 m 2H, 2.47 s 3H, 2.12 s 3H, 1.95 s 3H. Identification of Example 6 by $^1$H-NMR showed that the oxime product was a single isomer, but did not confirm whether the (E) or (Z) oxime isomer had been obtained.

Step (g): To a stirred solution of 5-(3,5-dimethylisoxazol-4-yl)-1-(4-hydroxyphenyl)-3-methyl-1H-pyrazole-4-carbaldehyde (69 mg, 0.23 mmol), in dry CH$_2$Cl$_2$ (3 mL) under N$_2$ at −78° C. was added DIBAL-H (1 M solution in hexane, 1.17 mL, 1.17 mmol) over approximately 10 min. The reaction was allowed to reach room temperature. After 1 h the reaction was again cooled to −78° C. and EtOH (1 mL) followed by 3 M HCl (6 mL) was added carefully. The mixture was extracted into EtOAc and after concentration onto silica and purification (silica short plug) EtOAc:heptane 1:1 gave 5-(3,5-dimethylisoxazol-4-yl)-1-(4-hydroxyphenyl)-3-methyl-1H-pyrazole-4-carbaldehyde in quantitative yield, that was used directly in the next step.

Step (h): The semi-crude 5-(3,5-dimethylisoxazol-4-yl)-1-(4-hydroxyphenyl)-3-methyl-1H-pyrazole-4-carbaldehyde was mixed with hydroxylamine hydrochloride (100 mg, 0.014 mmol) and pyridine (0.15 mL) in dry ethanol (1.5 mL) and heated at 150° C. for 10 min in the microwave. 1 M HCl and CH$_2$Cl$_2$ were added and the phases were separated. The oxime was purified on preparative HPLC to give E3 5-(3,5-dimethylisoxazol-4-yl)-1-(4-hydroxyphenyl)-3-methyl-1H-pyrazole-4-carbaldehyde oxime (37 mg, 50%). Identification of the title compound by $^1$H-NMR showed that the product was an approximately 1:1 mixture of the (E) and (Z) oxime isomers. ES/MS m/z: 313.17 (M+H), 311.19 (M−H); $^1$H NMR (acetone-d6, 500 MHz): 7.83 s 1H, 7.13 m 2H, 6.87 m 2H; 2.41 s 3H, 1.88 s 3H.

Step (i): n-BuLi (1.6 M solution in hexanes, 6 mL, 9.6 mmol) was added to a cooled (−78° C.) solution of 4-iodo-3,5-dimethylisoxazole (1.47 g, 6.60 mmol) in THF (24 mL) under nitrogen. After 15 min, tributyltin chloride (26 mL, 9.60 mmol) was added and the reaction was stirred over night while warming to room temperature. The reaction was quenched by 1 M HCl, CH$_2$Cl$_2$ was added, the phases separated and the solvent were evaporated. The residue was purified by flash chromatography with heptane:CH$_2$Cl$_2$ (75:25-0:100) to give 3,5-dimethyl-4-(tributylstannyl)isoxazole (1.00 g, 39%).

EXAMPLE 4 AND 5

5-(3,5-dimethylisoxazol-4-yl)-1-(4-hydroxyphenyl)-3-propyl-1H-pyrazole-4-carbaldehyde oxime (E4)

5-(3,5-dimethylisoxazol-4-yl)-N'-hydroxy-1-(4-hydroxyphenyl)-3-propyl-1H-pyrazole-4-carboximidamide (E5)

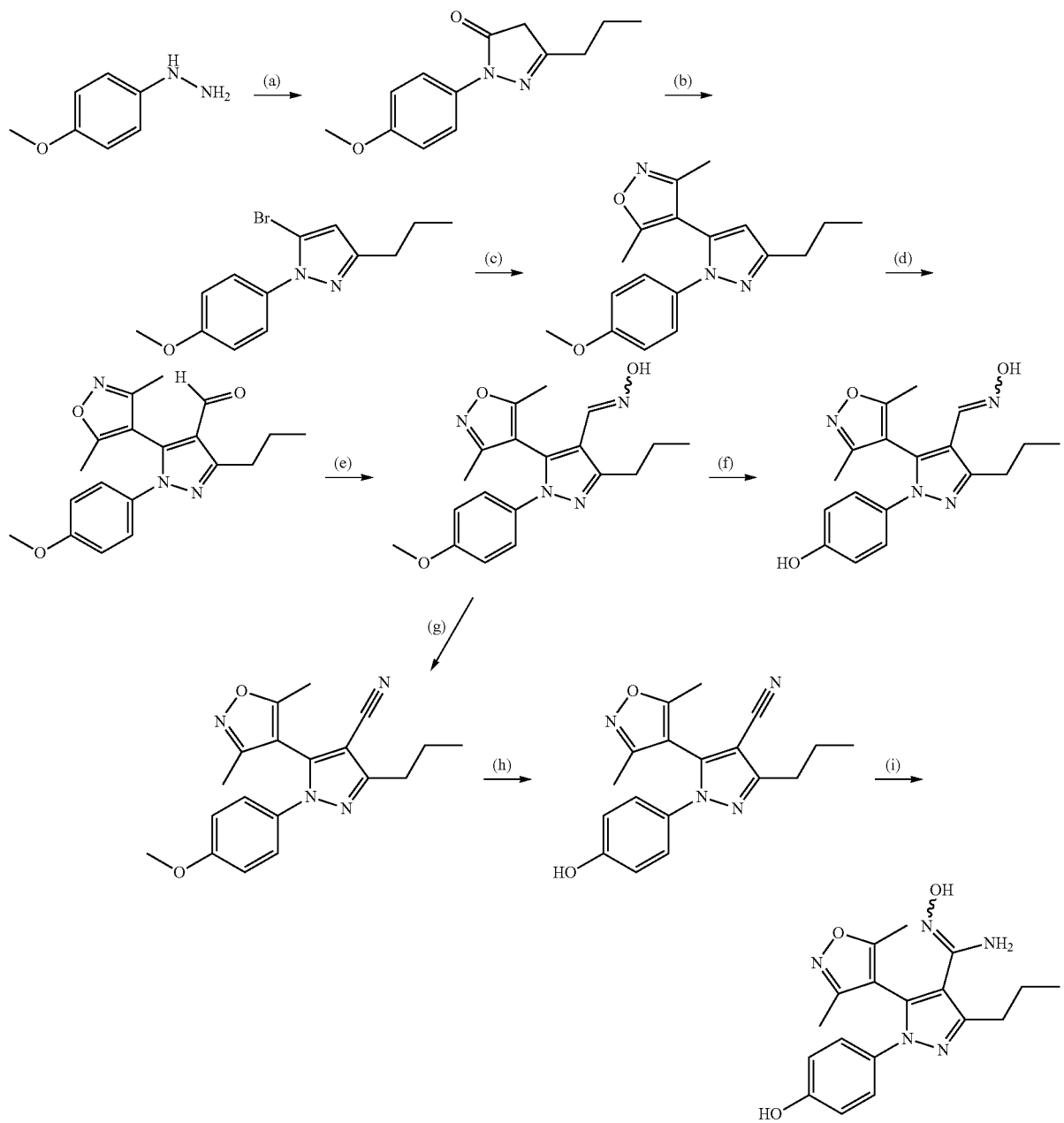

(a) ethyl 3-oxohexanoate, AcOH, Et₃N; (b) PBr₃ (MeCN); (c) Pd(PPh₃)₄, 3,5-dimethylisoxazol-4-ylboronic acid, K₂CO₃ NaI (dioxane/water); (d) POCl₃, DMF (toluene); (e) NH₂OH*HCl, pyridine (EtOH); (f) BBr₃ (DCM); (g) Ac₂O; (h) BBr₃ (DCM); (i) NH₂OH (DMSO/water)

Step (a): To a suspension of ethyl 3-oxohexanoate (0.58 mL, 3.62 mmol) and (4-methoxyphenyl)hydrazine (0.50 g, 3.62 mmol) in AcOH (3.5 mL) was added Et₃N (0.58 mL, 4.16 mmol). The mixture was stirred at 120° C. for 30 h. The solvent was removed by evaporation, and the residue was dissolved in DCM/EtOAc which was washed with saturated aqueous NaHCO₃, followed by water and dried using phase separator. Concentration in vacuo, and purification using silica chromatography (CH$_2$Cl$_2$:Et$_2$O 3:1) gave 1-(4-methoxyphenyl)-3-propyl-1H-pyrazol-5(4H)-one (495 mg, 59%).

Step (b): 1-(4-Methoxyphenyl)-3-propyl-1H-pyrazol-5(4H)-one (495 mg, 2.13 mmol) was put in a microwave tube and closed, MeCN (2.1 mL) and PBr$_3$ (6.4 mL, 68.2 mmol) were added via syringe and the reaction was stirred at 150° C. for 40 min in the microwave. The product poured onto ice and was extracted with EtOAc. The organic phase was separated from the water phase and evaporated. The crude product was purified on silica column (CH$_2$Cl$_2$/Et$_2$O, 1:1) to give 5-bromo-1-(4-methoxyphenyl)-3-propyl-1H-pyrazole (287 mg, 46%).

Step (c): 5-Bromo-1-(4-methoxyphenyl)-3-propyl-1H-pyrazole (287 mg, 0.97 mmol), 3,5-dimethylisoxazol-4-ylboronic acid (274 mg, 1.94 mmol), K$_2$CO$_3$ (806 mg, 5.83 mmol), sodium iodide (291 mg, 1.94 mmol) and Pd(PPh$_3$)$_4$ (90 mg, 0.08 mmol) were mixed with degassed dioxane (1 mL) and degassed H$_2$O (1 mL) under nitrogen in a microwave vial. The reaction was heated at 150° C. for 20 min. The crude mixture was diluted with CH$_2$Cl$_2$ and washed with water. The organic phase was separated from the water phase, dried using a phase separator and evaporated. The crude product was purified on silica column (CH$_2$Cl$_2$:Et$_2$O, 90:10) to give 4-(1-(4-methoxyphenyl)-3-propyl-1H-pyrazol-5-yl)-3,5-dimethylisoxazole (178 mg, 59%).

Step (d): Phosphorus oxychloride (599 μL, 6.42 mmol) was added dropwise to dry N,N-dimethylformamide, (497 μL, 6.42 mmol) in toluene (0.6 mL) at 0° C. The mixture was stirred for 5 minutes. Then 4-(1-(4-methoxyphenyl)-3-propyl-1H-pyrazol-5-yl)-3,5-dimethylisoxazole (160 mg, 0.51 mmol) was added, dissolved in toluene (0.5 mL) and the reaction mixture was heated at 150° C. for 20 minutes in the microwave. CH$_2$Cl$_2$ and water were added, a phase separator was used to separate and dry the organic phase. Filtration through a short silica plug gave semi-crude 5-(3,5-dimethylisoxazol-4-yl)-1-(4-methoxyphenyl)-3-propyl-1H-pyrazole-4-carbaldehyde which was used as such in the next step without further purification.

Step (e): The semi-crude 5-(3,5-dimethylisoxazol-4-yl)-1-(4-methoxyphenyl)-3-propyl-1H-pyrazole-4-carbaldehyde from step (d) was mixed with hydroxylamine hydrochloride (200 mg, 2.89 mmol) and pyridine (0.3 mL, 3.71 mmol) in dry ethanol (3 mL) and heated at 150° C. for 10 minutes in the microwave. 1 M HCl and CH$_2$Cl$_2$ were added and the phases were separated. The oxime was purified on preparative HPLC, to give 5-(3,5-dimethylisoxazol-4-yl)-1-(4-methoxyphenyl)-3-propyl-1H-pyrazole-4-carbaldehyde oxime (13 mg, 0.037 mmol).

Step (f): 10% of the crude (E)-5-(3,5-dimethylisoxazol-4-yl)-1-(4-methoxyphenyl)-3-propyl-1H-pyrazole-4-carbaldehyde oxime (1.2 mg, 0.003 mmol) from step (e) was dissolved in CH$_2$Cl$_2$ (4 mL) and BBr$_3$ (1 M solution in DCM, 0.4 mL, 0.37 mmol) was added. The mixture was stirred at room temperature for 4 h. Water and DCM were added and the phases were separated. The organic phase was purified on preparative HPLC to give E4 5-(3,5-dimethylisoxazol-4-yl)-1-(4-methoxyphenyl)-3-propyl-1H-pyrazole-4-carbaldehyde oxime (0.58 mg, 3% over three steps). Identification of the title compound by $^1$H-NMR showed that the oxime product was a single isomer, but did not confirm whether the (E) or (Z) oxime isomer had been obtained. ES/MS m/z: 341.16 (M+H), 339.25 (M−H); $^1$H NMR (acetone-d6, 500 MHz): 7.84 s 1H, 7.14 m 2H, 6.85 m 2H; (missing m 2H under H2O); 2.18 s 3H, 1.85 s 3H, 1.75 m 2H, 0.99 t (7.6 Hz) 3H.

Step (g): 90% of the crude (E)-5-(3,5-dimethylisoxazol-4-yl)-1-(4-methoxyphenyl)-3-propyl-1H-pyrazole-4-carbaldehyde oxime (12 mg, 0.034 mmol) from step (e) was dissolved in acetic anhydride and heated at 140° C. for 40 minutes in the microwave. The reaction mixture was concentrated onto silica and filtered through a silica plug to give 5-(3,5-dimethylisoxazol-4-yl)-1-(4-methoxyphenyl)-3-propyl-1H-pyrazole-4-carbonitrile (12 mg, 100%).

Step (h): (3,5-Dimethylisoxazol-4-yl)-1-(4-methoxyphenyl)-3-propyl-1H-pyrazole-4-carbonitrile (12 mg, 0.036 mmol) was dissolved in CH$_2$Cl$_2$ (3 mL) and BBr$_3$ (1 M solution in DCM, 0.3 mL, 0.28 mmol) was added. The mixture was stirred at room temperature over night. Water and DCM were added and the phases were separated. The organic phase was purified on a silica plug to give 5-(3,5-dimethylisoxazol-4-yl)-1-(4-hydroxyphenyl)-3-propyl-1H-pyrazole-4-carbonitrile (5.4 mg, 47%).

Step (i): A neutral 2 M solution of hydroxylamine hydrochloride and NaOH in water (0.5 mL, 1.0 mmol) was added to 5-(3,5-dimethylisoxazol-4-yl)-1-(4-hydroxyphenyl)-3-propyl-1H-pyrazole-4-carbonitrile (5.4 mg, 0.017 mmol) in DMSO (0.5 mL) and stirred at 65° C. over night. Crude LCMS on the reaction mixture show 41% product, 38% amide and 21% starting material. Purification using preparative HPLC gave E5 5-(3,5-dimethylisoxazol-4-yl)-N'-hydroxy-1-(4-hydroxyphenyl)-3-propyl-1H-pyrazole-4-carboximidamide (1.42 mg, 24%). Identification of the title compound by $^1$H-NMR showed that the oxime product was a single isomer, but did not confirm whether the (E) or (Z) oxime isomer had been obtained. ES/MS m/z: 356.2 (M+H), 354.21 (M−H); $^1$H NMR (acetone-d6, 500 MHz): 7.11 m 2H, 6.85 m 2H, 2.77 m 2H, 2.11 s 3H, 1.88 s 3H, 1.75 m 2H, 0.98 t (7.5 Hz) 3H.

EXAMPLE 6

5-(2,5-dimethyl-1H-pyrrol-1-yl)-1-(2-fluoro-4-hydroxyphenyl)-N'-hydroxy-3-methyl-1H-pyrazole-4-carboximidamide (E6)

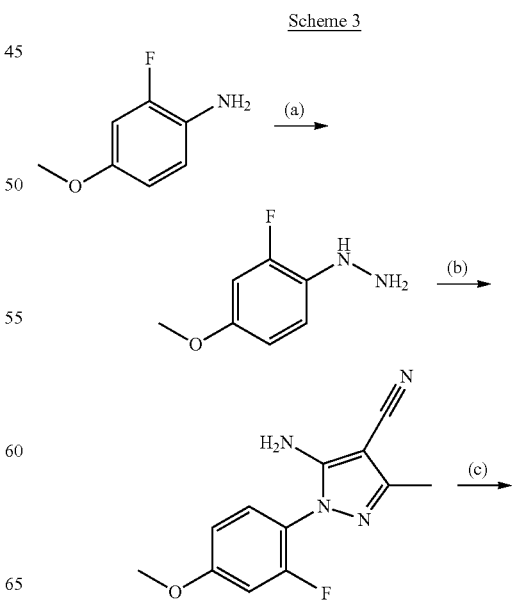

Scheme 3

-continued

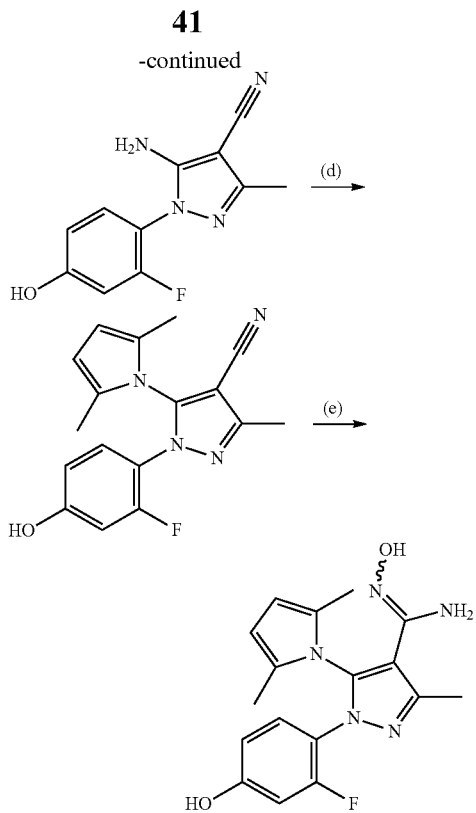

(a) NaNO₂, conc HCl, SnCl₂—2H₂O; (b) 2-(1-ethoxyethylidene)malononitrile (EtOH); (c) BBr₃ (CH₂Cl₂); (d) acetonylacetone, AcOH (e) NH₂OH (MeOH/water)

Step (a): To a vigorously stirred suspension of 2-fluoro-4-methoxyaniline hydrochloride (665 mg, 3.7 mmol) in conc. HCl (5.5 mL) cooled to 0° C. was added a cold solution of NaNO₂ (312 mg, 4.5 mmol) in H₂O (1 mL). The mixture was stirred at 0° C. for 90 min. A cold solution of SnCl₂·2H₂O (3.4 g, 15.0 mmol) in conc. HCl (5.5 mL) was then added slowly to the solution of diazonium salt. The reaction was allowed to warm to room temperature, stirred for 30 min and the reaction was filtered. The collected precipitate was washed on the filter with several large portions of ether and dried under vacuum. The solid was dissolved in DCM and washed saturated NaHCO₃, extracted and dried using a phase separator. Evaporation gave (2-fluoro-4-methoxyphenyl)hydrazine (220 mg 38%), which was used in the next step without further purification. The procedure was adapted from *J. Med. Chem.* 2000, 43, 4701.

Step (b): To a stirred solution of 2-(1-ethoxyethylidene)malononitrile (167 mg, 1.23 mmol) was added (2-fluoro-4-methoxyphenyl)hydrazine (220 mg, 1.41 mmol) in EtOH (3 mL). The solution was heated to 105° C. in the microwave for 30 min. CH₂Cl₂ and 1 M HCl was added and separated, the organic extract was washed with aqueous NaHCO₃. The solution was dried using a phase separator and concentrated under reduced pressure to give 5-amino-1-(2-fluoro-4-methoxyphenyl)-3-methyl-1H-pyrazole-4-carbonitrile (256 mg, 85%), which was used in the next step without further purification.

Step (c): The crude 5-amino-1-(2-fluoro-4-methoxyphenyl)-3-methyl-1H-pyrazole-4-carbonitrile (256 mg, 1.04 mmol) from above was dissolved in CH₂Cl₂ (25 mL) and BBr₃ (1 M solution in DCM, 5 mL, 5.0 mmol) was added and stirred over night. CH₂Cl₂ and water were added and the phases separated. The aqueous phase was again extracted with EtOAc/CH₂Cl₂ (1:1). The solution was dried using a phase separator and concentrated under reduced pressure to give 5-amino-1-(2-fluoro-4-hydroxyphenyl)-3-methyl-1H-pyrazole-4-carbonitrile (217 mg, 76%), which was used as such in the next step.

Step (d): A solution of 5-amino-1-(2-fluoro-4-hydroxyphenyl)-3-methyl-1H-pyrazole-4-carbonitrile (100 mg, 0.43 mmol) and acetonylacetone (507 µL, 4.31 mmol) in glacial acetic (3 mL) acid was heated at 140° C. in the micro for 30 min. The mixture was transferred to a round bottom flask using EtOAc and evaporated, toluene was added and again evaporated, CH₂Cl₂ and silica was finally added and the mixture was evaporated to dryness. Purification using silica chromatography (short plug) gave 5-(2,5-dimethyl-1H-pyrrol-1-yl)-1-(2-fluoro-4-hydroxyphenyl)-3-methyl-1H-pyrazole-4-carbonitrile (132 mg, 99%) as a 1:1 mixture with the starting material acetonylacetone. The product was used as such in the next step.

Step (e): Hydroxylamine (50 wt % solution in water, 0.8 mL, 13.5 mmol) was added to 5-(2,5-dimethyl-1H-pyrrol-1-yl)-1-(2-fluoro-4-hydroxyphenyl)-3-methyl-1H-pyrazole-4-carbonitrile (28 mg, 0.09 mmol) dissolved in MeOH (1.6 mL). The reaction was heated at 150° C. in the microwave for 15 min. Purification using preparative HPLC gave 5-(2,5-dimethyl-1H-pyrrol-1-yl)-1-(2-fluoro-4-hydroxyphenyl)-N'-hydroxy-3-methyl-1H-pyrazole-4-carboximidamide (8.68 mg, 28%). Identification of the title compound by ¹H-NMR showed that the oxime product was a single isomer, but did not confirm whether the (E) or (Z) oxime isomer had been obtained. ES/MS m/z: 344.14 (M+H), 342.25 (M−H); ¹H NMR (acetone-d6, 500 MHz): 7.13 (t, 1H, J=8.5 Hz), 6.68 (m, 2H), 5.76 (s, 2H), 2.40 (s, 3H) and 1.95 (s, 6H).

EXAMPLE 7

5-(diethylamino)-3-ethyl-N'-hydroxy-1-(4-hydroxyphenyl)-1H-pyrazole-4-carboximidamide (E7)

Scheme 4

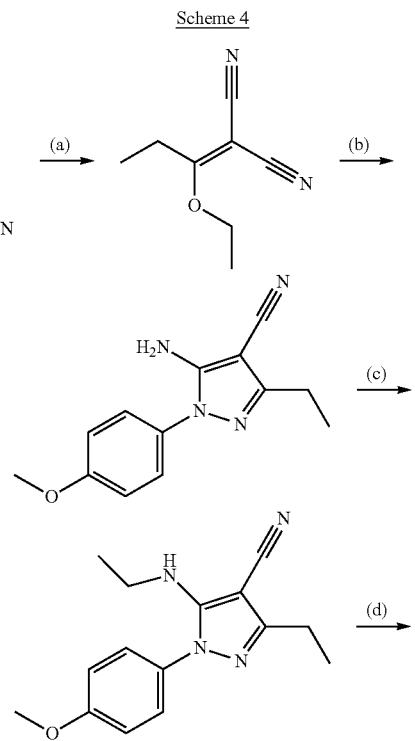

-continued

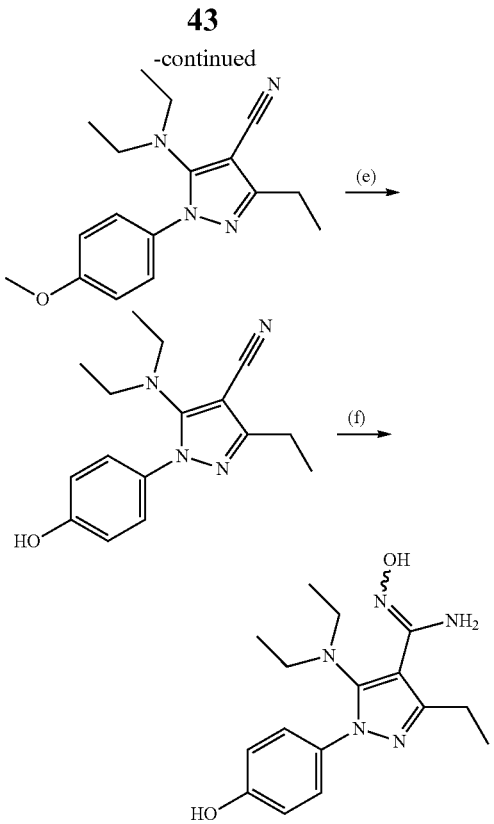

(a) 1,1,1-triethoxypropane, Ac₂O; (b) (4-methoxyphenyl)hydrazine (EtOH); (c) LDA, EtBr (THF); (d) LDA, EtBr (THF); (e) BBr₃ (CH₂Cl₂) (f) NH₂OH (MeOH/water)

Step (a): To a stirred solution of malononitrile (2.64 g, 40.0 mmol) in acetic anhydride (9 mL) was added 1,1,1-triethoxypropane (8.04 g, 40.0 mmol). The solution was stirred for 15 h at reflux, cooled, and poured into water. The mixture was extracted with ether, and the organic extract was washed with aqueous NaHCO₃ and then brine. The solution was dried (MgSO₄) and concentrated under reduced pressure to afford a solid identified as 2-(1-ethoxypropylidene)malononitrile (5.80 g, 97%). The procedure was adapted from *J. Med. Chem.* 2004, 47, 5894-5911.

Step (b): To a stirred solution of 2-(1-ethoxyethylidene) malononitrile (1.00 g, 6.66 mmol) in EtOH (8 mL) was added (4-methoxyphenyl)hydrazine (1.29 g, 9.32 mmol). (Prior to use the hydrazine its HCl salt was washed with NaHCO₃/CH₂Cl₂. The organic phase was concentrated and used directly.) The solution was heated to 105° C. in the microwave for 20 min. CH₂Cl₂ was added and the organic phase was washed with 1M HCl and the organic extract was washed with aqueous NaHCO₃. The solution was dried using a phase separator and concentrated under reduced pressure to give 5-amino-1-(4-methoxyphenyl)-3-methyl-1H-pyrazole-4-carbonitrile (1.38 g, 85%) which was used as such in the next step. The procedure was adapted from *J. Med. Chem.* 2004, 47, 5894-5911.

Step (c): To 5-amino-3-ethyl-1-(4-methoxyphenyl)-1H-pyrazole-4-carbonitrile (0.50 g, 2.06 mmol) in THF (10 mL) at −78C was added LDA (0.6 M in THF, 4.5 mL, 2.7 mmol) and stirred for 5 min, followed by EtBr (500 μL, 6.81 mmol) and the reaction was stirred over night at room temperature. Et₂O and water were added, and the organic phase was separated. The water phase was acidified using 1 M HCl which was extracted with EtOAc. After drying using MgSO₄, and evaporation of solvent the crude was purified using silica chromatography to give 3-ethyl-5-(ethylamino)-1-(4-methoxyphenyl)-1H-pyrazole-4-carbonitrile (130 mg, 23%).

Step (d): 3-ethyl-5-(ethylamino)-1-(4-methoxyphenyl)-1H-pyrazole-4-carbonitrile (130 mg, 0.48 mmol) in THF (2.4 mL) at −78C was added LDA (0.6 M solution in THF, 1.0 mL, 0.6 mmol) and stirred for 5 min, followed by EtBr (118 μL, 1.5 mmol) and the reaction was stirred over night at room temperature. Et₂O and water were added, and the organic phase was separated. The water phase was acidified using 1 M HCl which was extracted with EtOAc. After drying using MgSO₄, and evaporation of solvent the crude was purified using silica chromatography to give 3-ethyl-5-(ethylamino)-1-(4-methoxyphenyl)-1H-pyrazole-4-carbonitrile (39 mg, 27%).

Step (e): The 5-(diethylamino)-3-ethyl-1-(4-methoxyphenyl)-1H-pyrazole-4-carbonitrile (39 mg, 0.13 mmol) from above was dissolved in CH₂Cl₂ (5 mL) and BBr₃ (1 M solution in DCM, 1 mL, 1.0 mmol) was added and stirred over night. CH₂Cl₂ and water were added and the phases were separated, the aqueous phase was again extracted with EtOAc/CH₂Cl₂ (1:1). The solution was dried using a phase separator and concentrated under reduced pressure. Purification using preparative HPLC gave 5-(diethylamino)-3-ethyl-1-(4-hydroxyphenyl)-1H-pyrazole-4-carbonitrile (36 mg, 97%).

Step (f): Hydroxylamine (50 wt % solution in water, 0.45 mL, 7.3 mmol) was added to 5-(diethylamino)-3-ethyl-1-(4-hydroxyphenyl)-1H-pyrazole-4-carbonitrile (16 mg, 0.06 mmol) dissolved in DMSO (1 mL) in a microwave vial. The reaction was heated at 160° C. in the microwave for 30 min. Purification using preparative HPLC gave (Z)-5-(diethylamino)-3-ethyl-N'-hydroxy-1-(4-hydroxyphenyl)-1H-pyrazole-4-carboximidamide (6.22 mg, 35%). Identification of the title compound by ¹H-NMR showed that the oxime product was a single isomer, but did not confirm whether the (E) or (Z) oxime isomer had been obtained. ES/MS m/z: 318.29 (M+H), 316.32 (M−H); ¹H NMR (acetone-d6, 500 MHz): 7.40 (m, 2H), 6.90 (m, 2H), 2.96 (q, 4H, J=7.2 Hz), 2.65 (q, 2H, J=7.4 Hz), 1.19 (t, 3H, J=7.4 Hz) and 0.95 (t, 6H, J=7.2 Hz).

EXAMPLES 8 AND 9

5-(1,3-dimethyl-1H-pyrrol-2-yl)-1-(2-fluoro-4-hydroxyphenyl)-N'-hydroxy-3-methyl-1H-pyrazole-4-carboximidamide (E8)

5-(5-bromo-1,3-dimethyl-1H-pyrrol-2-yl)-1-(2-fluoro-4-hydroxyphenyl)-N'-hydroxy-3-methyl-1H-pyrazole-4-carboximidamide (E9)

Scheme 5

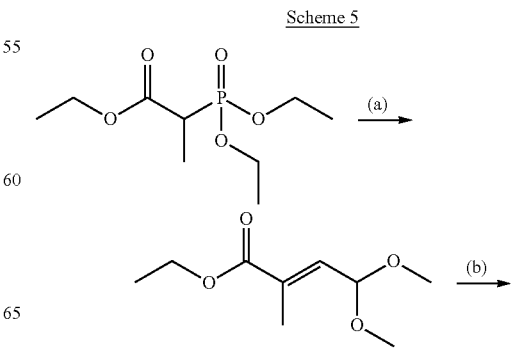

-continued

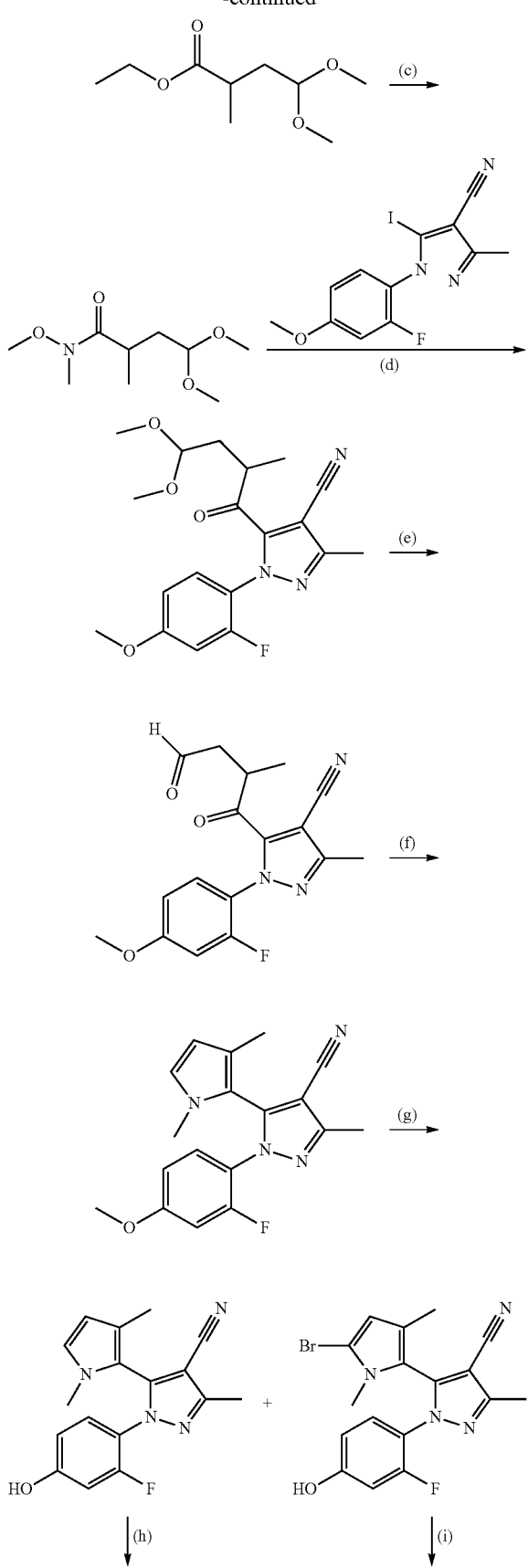

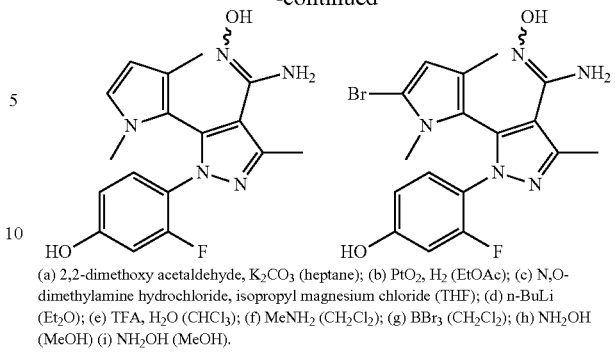

(a) 2,2-dimethoxy acetaldehyde, $K_2CO_3$ (heptane); (b) $PtO_2$, $H_2$ (EtOAc); (c) N,O-dimethylamine hydrochloride, isopropyl magnesium chloride (THF); (d) n-BuLi ($Et_2O$); (e) TFA, $H_2O$ ($CHCl_3$); (f) $MeNH_2$ ($CH_2Cl_2$); (g) $BBr_3$ ($CH_2Cl_2$); (h) $NH_2OH$ (MeOH) (i) $NH_2OH$ (MeOH).

Step (a): To a stirred solution of ethyl 2-(diethoxyphosphoryl)propanoate (450 μL, 2.1 mmol) in heptane (5 mL) was added 2,2-dimethoxy acetaldehyde (60% in water, 1.0 mL, 4.2 mmol). The solution was stirred for 15 h at 60° C. After the reaction was cooled, water was added and the mixture was extracted with $CH_2Cl_2$ and filtered through a phase separator and a silica plug. Concentration under reduced pressure afforded (E)-ethyl 4,4-dimethoxy-2-methylbut-2-enoate (480 mg, >100%). The procedure was adapted from *Tetrahedron* 2002, 2533.

Step (b): To a stirred solution of (E)-ethyl 4,4-dimethoxy-2-methylbut-2-enoate (1.32 g, 7.01 mmol) in EtOAc (30 mL) was added $PtO_2$ (51 mg, 0.22 mmol). The slurry was hydrogenated over night. Filtration trough celite, concentration and purification using silica gel ($CH_2Cl_2$-$Et_2O$ 1:0 to 0:1) afforded ethyl 4,4-dimethoxy-2-methylbutanoate (0.88 g, 66%).

Step (c): To a stirred solution of ethyl 4,4-dimethoxy-2-methylbutanoate (90 mL, 0.53 mmol) and N,O-dimethylamine hydrochloride (80 mg, 0.81 mmol) in THF (1 mL) at −20° C., was added dropwise isopropyl magnesium chloride (2 M solution in THF, 0.8 mL, 1.58 mmol). After stirring at −10° C. for 90 min the reaction was quenched with water, extracted into EtOAc/$CH_2Cl_2$ and dried using a phase separator. Concentration gave N,4,4-trimethoxy-N,2-dimethylbutanamide (80 mg, 74%). Crude H-NMR indicated complete conversion to the Weinreb amide. The product was used as such in the next step.

Step (d): To 1-(2-fluoro-4-methoxyphenyl)-5-iodo-3-methyl-1H-pyrazole-4-carbonitrile (66 mg, 0.18 mmol) in $Et_2O$ (1.5 mL) at −78° C. was added n-BuLi (2.5 M solution in hexane, 0.1 mL, 0.24 mmol). After stirring for 15 min, N,4,4-trimethoxy-N,2-dimethylbutanamide was added in $Et_2O$ (1.5 mL). The reaction was stirred at −78° C. for 15 hours while warming to −40° C. The reaction was quenched with water and extracted using a mixture of $Et_2O$ and DCM. Drying using a phase separator followed by concentration and purification using silica gel (heptane-EtOAc, 1:0 to 0:1) afforded 5-(4,4-dimethoxy-2-methylbutanoyl)-1-(2-fluoro-4-methoxyphenyl)-3-methyl-1H-pyrazole-4-carbonitrile (33 mg, 48%).

Step (e): A solution of 5-(4,4-dimethoxy-2-methylbutanoyl)-1-(2-fluoro-4-methoxyphenyl)-3-methyl-1H-pyrazole-4-carbonitrile (33 mg, 0.09 mmol) in $CHCl_3$ (1.5 mL) was added TFA (0.4 mL) and water (0.4 mL) and the reaction was stirred 3 h at room temperature. The mixture was diluted with saturated aqueous solution of $NaHCO_3$ and $CH_2Cl_2$. The organic phase was separated and the aqueous phase was extracted with $CH_2Cl_2$. The organic phase was then washed with saturated aqueous solution of NaHCO₃. The combined extracts were dried with a phase separator and concentrated. The desired 1-(2-fluoro-4-methoxyphenyl)-3-methyl-5-(2-methyl-4-oxobutanoyl)-1H-pyrazole-4-carbonitrile (29 mg, 100%) was obtained and used immediately in the next step.

Step (f): To a stirred solution of 1-(2-fluoro-4-methoxyphenyl)-3-methyl-5-(2-methyl-4-oxobutanoyl)-1H-pyrazole-4-carbonitrile (29 mg, 0.09 mmol) in CH₂Cl₂ (2 mL) was added methylamine (2.0 M solution in methanol, 0.61 mL, 1.2 mmol) at ambient temperature in a closed microwave tube. The reaction mixture was stirred at ambient temperature for 14 h and concentrated under reduced pressure. Purification using a silica plug (heptane/CH₂Cl₂/Et₂O-1:0:0-1:1:0-0:1:0-0:1:1) yielded 5-(1,3-dimethyl-1H-pyrrol-2-yl)-1-(2-fluoro-4-methoxyphenyl)-3-methyl-1H-pyrazole-4-carbonitrile (20 mg, 62%).

Step (g): 5-(1,3-Dimethyl-1H-pyrrol-2-yl)-1-(2-fluoro-4-methoxyphenyl)-3-methyl-1H-pyrazole-4-carbonitrile (20 mg, 0.06 mmol) was dissolved in CH₂Cl₂ (3 mL) and BBr₃ (1 M solution on DCM, 0.3 mL, 0.3 mmol) was added and stirred at room temperature over night. The reaction was quenched using water and extracted with CH₂Cl₂. Concentration and purification using preparative HPLC gave 5-(1,3-dimethyl-1H-pyrrol-2-yl)-1-(2-fluoro-4-hydroxyphenyl)-3-methyl-1H-pyrazole-4-carbonitrile (10 mg, 53%). Also 5-(5-bromo-1,3-dimethyl-1H-pyrrol-2-yl)-1-(2-fluoro-4-hydroxyphenyl)-3-methyl-1H-pyrazole-4-carbonitrile (7 mg) was isolated.

Step (h): Hydroxylamine (16.3 M solution in water, 0.3 mL, 4.8 mmol) was added to 5-(1,3-dimethyl-1H-pyrrol-2-yl)-1-(2-fluoro-4-hydroxyphenyl)-3-methyl-1H-pyrazole-4-carbonitrile (10 mg, 0.032 mmol) in MeOH (0.6 mL) and the reaction was stirred at 150° C. for 20 min in the microwave reactor. The crude reaction was purified on preparative HPLC to give E8 5-(1,3-dimethyl-1H-pyrrol-2-yl)-1-(2-fluoro-4-hydroxyphenyl)-N'-hydroxy-3-methyl-1H-pyrazole-4-carboximidamide (4.27 mg, 39%). Identification of the title compound by ¹H-NMR showed that the oxime product was a single isomer, but did not confirm whether the (E) or (Z) oxime isomer had been obtained. ES/MS m/z: 344.12 (M+H), 342.24 (M−H); ¹H NMR (acetone-d6, 500 MHz): 8.11 (s, 1H), 7.17 (t, 1H, J=8.8 Hz), 6.70 (d, 1H, J=2.87 Hz), 6.67 (m, 1H), 6.61 (dd, 1H, J=2.6, 11.9 Hz), 5.83 (d, 1H, J=2.71), 3.38 (s, 3H), 2.39 (s, 3H) and 1.72 (s, 3H).

Step (i): Hydroxylamine (16.3 M solution in water, 0.3 mL, 4.8 mmol) was added to 5-(5-bromo-1,3-dimethyl-1H-pyrrol-2-yl)-1-(2-fluoro-4-hydroxyphenyl)-3-methyl-1H-pyrazole-4-carbonitrile (7 mg, 0.018 mmol) in MeOH (0.6 mL) and the reaction was stirred at 150° C. for 20 min in the microwave. The crude reaction was purified on preparative HPLC to give E9 5-(5-bromo-1,3-dimethyl-1H-pyrrol-2-yl)-1-(2-fluoro-4-hydroxyphenyl)-N'-hydroxy-3-methyl-1H-pyrazole-4-carboximidamide (2.47 mg, 33%). Identification of the title compound by ¹H-NMR showed that the oxime product was a single isomer, but did not confirm whether the (E) or (Z) oxime isomer had been obtained. ES/MS m/z: 422.00, 424.00 (M+H), 420.09, 422.07 (M−H); ¹H NMR (acetone-d6, 500 MHz): 8.11 (s, 1H), 7.20 (t, 1H, J=8.8 Hz), 6.86 (s, 1H), 6.70 (m, 1H), 6.62 (dd, 1H, J=2.6, 11.9 Hz), 3.41 (s, 3H), 2.39 (s, 3H) and 1.66 (s, 3H).

EXAMPLE 10

3-ethyl-N'-hydroxy-1-(4-hydroxyphenyl)-5-(3-methylfuran-2-yl)-1H-pyrazole-4-carboximidamide (E10)

Scheme 6

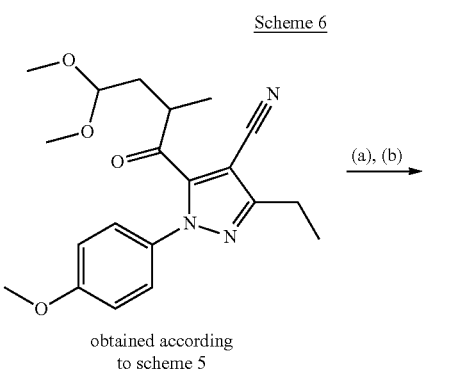

obtained according to scheme 5

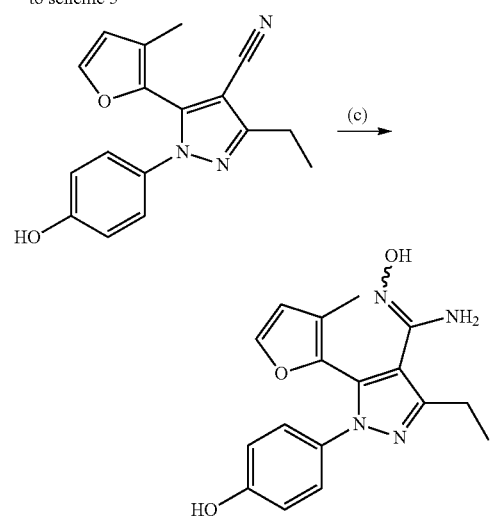

(a) MeNH₂, HCl_conc. (MeOH); (b) BBr₃ (CH₂Cl₂); (c) NH₂OH (MeOH)

Step (a): To a stirred solution of 5-(4,4-dimethoxy-2-methylbutanoyl)-3-ethyl-1-(4-methoxyphenyl)-1H-pyrazole-4-carbonitrile (20 mg, 0.05 mmol) in MeOH (1.5 mL) were added methylamine (2.0 M solution in methanol, 0.20 mL, 0.4 mmol) and conc. HCl (0.1 mL) at ambient temperature in a closed microwave tube. The reaction mixture was stirred at ambient temperature for 14 h then additional methylamine (2.0 M solution in methanol, 2.70 mL, 5.4 mmol) and conc. HCl (0.3 mL) were added and the reaction was heated to 8° C. for 14 hours. Water and CH₂Cl₂ was added, the phases separated and the organic phase was concentrated under reduced pressure. Purification using a silica plug (heptane/CH₂Cl₂/Et₂O-1:0:0-1:1:0-0:1:0-0:1:1) yielded 3-ethyl-1-(4-methoxyphenyl)-5-(3-methylfuran-2-yl)-1H-pyrazole-4-carbonitrile (5 mg, 0.02 mmol, 30%).

Step (b): 3-ethyl-1-(4-methoxyphenyl)-5-(3-methylfuran-2-yl)-1H-pyrazole-4-carbonitrile (5 mg, 0.02 mmol) was dissolved in CH₂Cl₂ (3 mL) and BBr₃ (1 M solution on DCM, 0.3 mL, 0.3 mmol) was added and stirred at room temperature over night. The reaction was quenched using water and extracted with CH₂Cl₂. Concentration gave a crude 3-ethyl-1-(4-hydroxyphenyl)-5-(3-methylfuran-2-yl)-1H-pyrazole-4-carbonitrile (5 mg, 0.02 mmol, 100%) which was used as such in the next step.

Step (c): Hydroxylamine (16.3 M solution in water, 0.3 mL, 4.8 mmol) was added to 3-ethyl-1-(4-hydroxyphenyl)-5-(3-methylfuran-2-yl)-1H-pyrazole-4-carbonitrile (5 mg, 0.02 mmol) in MeOH (0.6 mL) and the reaction was stirred at 150° C. for 20 min in the microwave reactor. The crude reaction was purified on preparative HPLC to give 3-ethyl-N'-hydroxy-1-(4-hydroxyphenyl)-5-(3-methylfuran-2-yl)-1H-pyrazole-4-carboximidamide (3.34 mg, 63%). Identification of the title compound by $^1$H-NMR showed that the oxime product was a single isomer, but did not confirm whether the (E) or (Z) oxime isomer had been obtained. ES/MS m/z: 327.1 (M+H), 325.23 (M−H); $^1$H NMR (acetone-d6, 500 MHz): 8.13 (s, 1H), 7.53 (d, 1H, J=1.9 Hz), 7.05 (m, 2H), 6.80 (m, 2H), 6.36 (d, 2H, J=1.9 Hz), 2.83 (q, 2H, J=7.6 Hz), 1.76 (s, 3H), and 1.26 (t, 3H, J=7.6 Hz).

EXAMPLES 11, 12, 13 AND 14

4-(4-(3,5-dimethylisoxazol-4-yl)-5-(hydroxymethyl)-1-methyl-1H-pyrazol-3-yl)phenol (E11)

4-(3,5-dimethylisoxazol-4-yl)-3-(4-hydroxyphenyl)-1-methyl-1H-pyrazole-5-carbaldehyde oxime (E12)

4-(3,5-dimethylisoxazol-4-yl)-N'-hydroxy-3-(4-hydroxyphenyl)-1-methyl-1H-pyrazole-5-carboximidamide (E13)

4-(3,5-dimethylisoxazol-4-yl)-3-(4-hydroxyphenyl)-1-methyl-1H-pyrazole-5-carboxamide (E14)

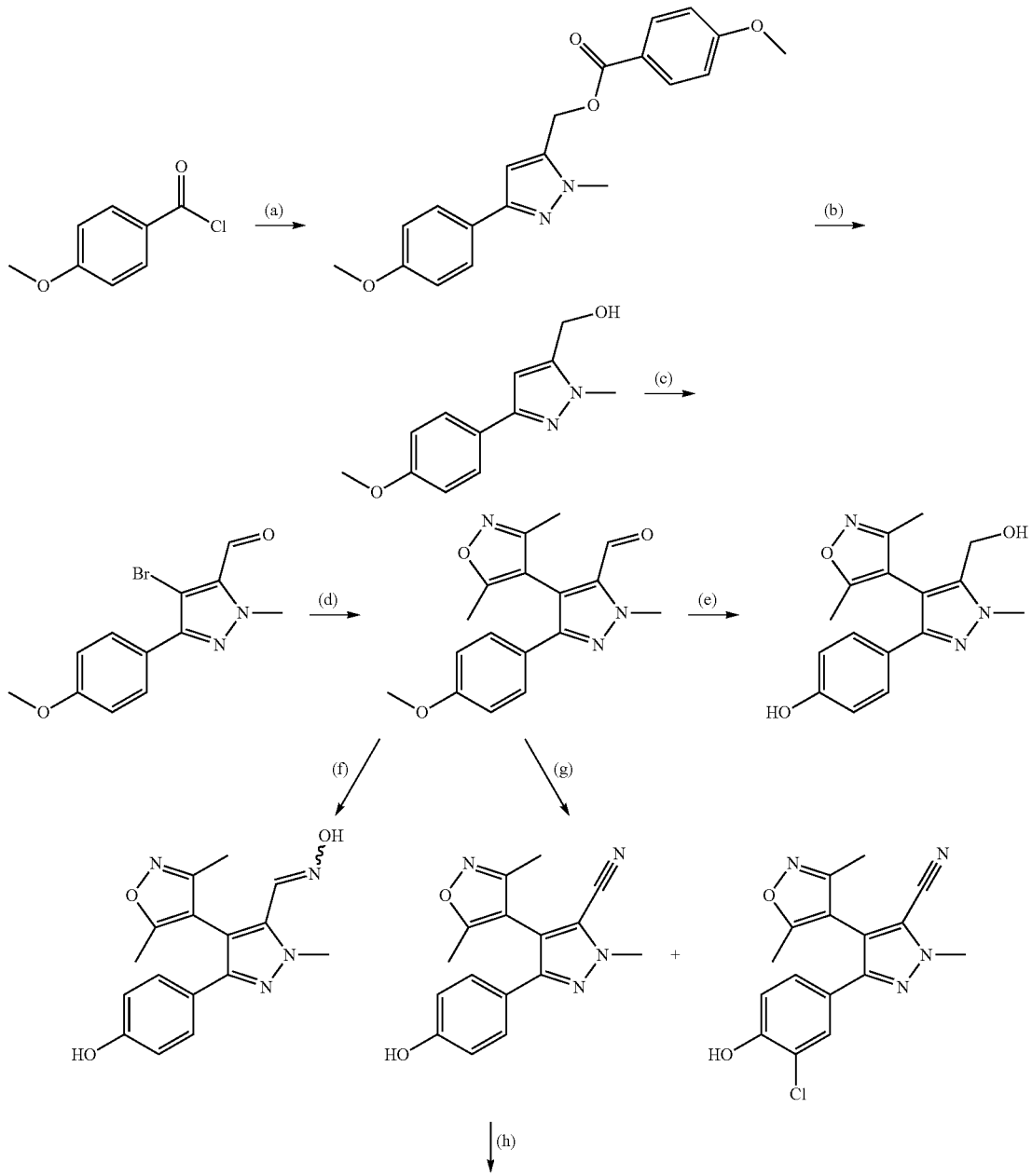

Scheme 7

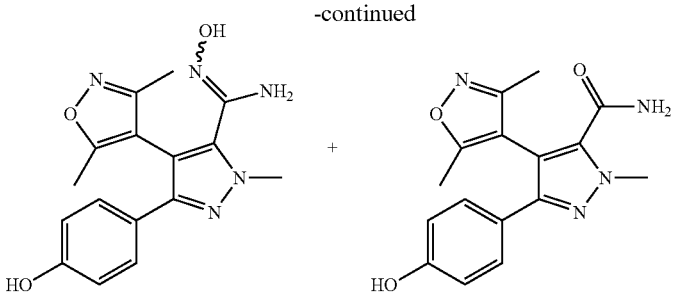

(a) 1) prop-2-yn-1-ol, PdCl$_2$(PPh$_3$)$_2$, CuI, TEA, 2) MeOH, AcOH MeNHNH$_2$; (b) LiBH$_4$ (EtOAc); (c) 1) NBS (MeCN) 2) Dess-Martin-periodinane; (d) 3,5-dimethylisoxazol-4-ylboronic acid, Pd(PPh$_3$)$_4$, K$_2$CO$_3$, (DME/H$_2$O); (e) 1) LiBH$_4$ (Et$_2$O), 2) BF$_3$·Me$_2$S (DCM); (f) NH$_2$OH·HCl, pyridine (EtOH), 2) BF$_3$·Me$_2$S (DCM); (g) 1) NH$_2$OH·HCl, pyridine (EtOH), 2) SOCl$_2$, 3) BF$_3$·Me$_2$S (DCM); (h) NH$_2$OH (DMSO/water)

Step (a): A mixture of prop-2-yn-1-ol (61.7 mg, 1.10 mmol), methoxybenzoylchloride (396 mg, 2.32 mmol) and triethylamine (229 µL, 1.65 mmol) in THF (2.5 mL) was stirred at room temperature for 50 min, then PdCl$_2$(PPh$_3$)$_2$ (30.9 mg, 0.04 mmol), CuI (16.8 mg, 0.09 mmol) and another 1.5 equiv triethylamine (167 mg, 1.65 mmol) were added to the mixture, degassed with N$_2$ and stirred at room temperature for 1 h. Then MeOH (0.6 mL), AcOH (0.6 mL) and methylhydrazine (118 µL, 2.2 mmol) were added to the reaction mixture and irradiated in the microwave at 150° C. for 25 min. The mixture was concentrated and purified on silica gel to give (3-(4-methoxyphenyl)-1-methyl-1H-pyrazol-5-yl)methyl 4-methoxybenzoate (269 mg, 0.76 mmol, 69%).

Step (b): To a solution of (3-(4-methoxyphenyl)-1-methyl-1H-pyrazol-5-yl)methyl 4-methoxybenzoate (80.0 mg, 0.23 mmol) in THF/Ether (2 mL/3 mL) was added LiBH$_4$ (12.0 mg, 0.44 mmol), and the reaction stirred at room temperature for 2 h. TLC indicated low consumption and more LiBH$_4$ (12.0 mg, 0.44 mmol) was added and stirred over night, quenched with water and extracted with EtOAc (2×10 mL), concentrated and purified on silica gel to give (3-(4-methoxyphenyl-1-methyl-1H-pyrazol-5-yl)methanol (44.0 mg, 0.20 mmol, 89%).

Step (c): A solution of (3-(4-methoxyphenyl)-1-methyl-1H-pyrazol-5-yl)methanol (398 mg, 1.82 mmol) and N-bromosuccinimide (341 mg, 1.91 mmol) in MeCN (35 mL) was stirred at room temperature for 40 min. To the solution was added Dess-Martin periodinane (812 mg, 1.91 mmol) and stirred at room temperature over night. The reaction mixture was filtered, concentrated and purified on silica gel to give 4-bromo-3-(4-methoxyphenyl-1-methyl-1H-pyrazole-5-carbaldehyde (477 mg, 1.62 mmol, 89%).

Step (d): A mixture of 4-bromo-3-(4-methoxyphenyl)-1-methyl-1H-pyrazole-5-carbaldehyde (74.5 mg, 0.25 mmol), 3,5-dimethylisoxazol-4-ylboronic acid (53.4 mg, 0.38 mmol), K$_2$CO$_3$ (140 mg, 1.01 mmol) and Pd(PPh$_3$)$_4$ (14.6 mg, 0.01 mmol) in 1 DME/water (1 mL/1 mL) was flushed with argon and irradiated in the microwave at 140° C. for 30 min, extracted with EtOAc (3×4 mL) after 3 mL water were added. The mixture was concentrated and purified on silica gel to give 4-(3,5-dimethylisoxazol-4-yl)-3-(4-methoxyphenyl)-1-methyl-1H-pyrazole-5-carbaldehyde (25.6 mg, 0.08 mmol, 33%).

Step (e): To a solution of 4-(3,5-dimethylisoxazol-4-yl)-3-(4-methoxyphenyl)-1-methyl-1H-pyrazole-5-carbaldehyde (4.1 mg, 0.013 mmol) in diethyl ether (3 mL) was added LiBH$_4$ (12 mg, 0.55 mmol) and stirred at room temperature over night. The reaction was then quenched with water and extracted with EtOAc, filtered through a phase separator and concentrated. To the raw product in DCM (1 mL) was added BF$_3$·Me$_2$S (1 M solution in DCM, 0.2 mL, 0.2 mmol) and stirred over night at room temperature. The formed precipitate was twice washed with 0.5 mL DCM, dissolved in MeOH and purified on preparative HPLC to give E11 4-(4-(3,5-dimethylisoxazol-4-yl)-5-(hydroxymethyl)-1-methyl-1H-pyrazol-3-yl)phenol (2.8 mg, 0.009 mmol, 71%). ES/MS m/z: 299.6 (M+H), 297.7 (M−H); $^1$H NMR (MeOD, 500 MHz): 7.18 (m, 2H), 6.71 (m, 2H), 3.98 (s, 3H), 3.74 (s, 2H), 2.20 (s, 3H) and 1.87 (s, 3H).

Step (f): A mixture of 4-(3,5-dimethylisoxazol-4-yl)-3-(4-methoxyphenyl)-1-methyl-1H-pyrazole-5-carbaldehyde (9.1 mg, 0.029 mmol), hydroxylamine hydrochloride (54.9 mg, 0.79 mmol) and pyridine (69 µL, 0.85 mmol) in dry EtOH (1 mL) was heated at 100° C. for 3 minutes in the microwave. 1 mL 2 M HCl and 5 mL DCM were added and the phases were separated. The organic phase was filtered through a phase separator and concentrated to give a raw product, that was dissolved in DCM (0.5 mL). BF$_3$·Me$_2$S (1 M solution in DCM, 0.5 mL, 0.5 mmol) was added and the mixture was stirred at room temperature over night. Methanol was added to quenched the reaction and the mixture was purified on preparative HPLC to give E12 4-(3,5-dimethylisoxazol-4-yl)-3-(4-hydroxyphenyl)-1-methyl-1H-pyrazole-5-carbaldehyde oxime (3.0 mg, 0.01 mmol, 32%). Identification of the title compound by $^1$H-NMR showed that the oxime product was a single isomer, but did not confirm whether the (E) or (Z) oxime isomer had been obtained. ES/MS m/z: 313.22 (M+H), 311.21 (M−H); $^1$H NMR (acetone-d6, 500 MHz): 7.92 (s, 1H), 7.31 (m, 2H), 6.79 (m, 2H), 4.08 (s, 3H), 2.15 (s, 3H) and 1.86 (s, 3H).

Step (g): A mixture of 4-(3,5-dimethylisoxazol-4-yl)-3-(4-methoxyphenyl)-1-methyl-1H-pyrazole-5-carbaldehyde (45.0 mg, 0.14 mmol), hydroxylamine hydrochloride (100 mg, 1.45 mmol) and pyridine (129 µL, 1.59 mmol) in ethanol (1 mL) was heated at 100° C. for 3 minutes in the microwave. 1 mL 2 M HCl and 5 mL DCM were added. A precipitate was formed, which was found to be the desired product. The remaining solution was extracted with DCM (5×3 mL). The DCM layer was filtered through a phase separator and concentrated together with the precipitate to give the raw product. To this was added thionyl chloride (3 mL) and the mixture was stirred at room temperature for 2 h and concentrated. Dry DCM (1 mL) and BF$_3$·Me$_2$S (1 M solution in DCM, 0.5 mL, 0.5 mmol) were added and stirred at room temperature over night. The mixture was concentrated and MeOH was added to quench the reaction The crude product was purified on silica gel to give 4-(3,5-dimethylisoxazol-4-yl)-3-(4-hydroxyphenyl)-1-methyl-1H-pyrazole-5-carbonitrile (30.5 mg, 0.01 mmol, 68%), and 3-(3-chloro-4-hydroxyphenyl)-4-(3,5-dimethylisoxazol-4-yl)-1-methyl-1H-pyrazole-5-carbonitrile (6.0 mg, 0.018 mmol, 13%).

Step (h): To a solution of 4-(3,5-dimethylisoxazol-4-yl)-3-(4-hydroxyphenyl)-1-methyl-1H-pyrazole-5-carbonitrile in DMSO (1.5 mL) was added neutral hydroxylamine solution (2 M in water, 1.27 mL, 2.55 mmol) and stirred at 130° C. for 10 min. EtOAc and water were added and the phases were separated. The crude product was purified on preparative HPLC to give E13 4-(3,5-dimethylisoxazol-4-yl)-N'-hydroxy-3-(4-hydroxyphenyl)-1-methyl-1H-pyrazole-5-carboximidamide (11.3 mg, 0.035 mmol, 34%) ES/MS m/z: 328.1 (M+H), 326.5 (M−H); $^1$H NMR (acetone-d6, 500 MHz): 7.29 (m, 2H), 6.78 (m, 2H), 3.95 (s, 3H), 2.10 (s, 3H) and 1.88 (s, 3H), and E14 4-(3,5-dimethylisoxazol-4-yl)-3-(4-hydroxyphenyl)-1-methyl-1H-pyrazole-5-carboxamide (12.7 mg, 0.041 mmol, 40%), ES/MS m/z: 313.1 (M+H), 311.5 (M−H); $^1$H NMR (acetone-d6, 500 MHz): 7.25 (m, 2H), 6.79 (m, 2H), 4.11 (s, 3H), 2.11 (s, 3H) and 1.92 (s, 3H).

For Example 18, identification of the title compound by $^1$H-NMR showed that the oxime product was a single isomer, but did not confirm whether the (E) or (Z) oxime isomer had been obtained.

EXAMPLE 15

4-(4-(3,5-dimethylisoxazol-4-yl)-5-(2-hydroxyethyl)-1-methyl-1H-pyrazol-3-yl)phenol (E15)

Scheme 8

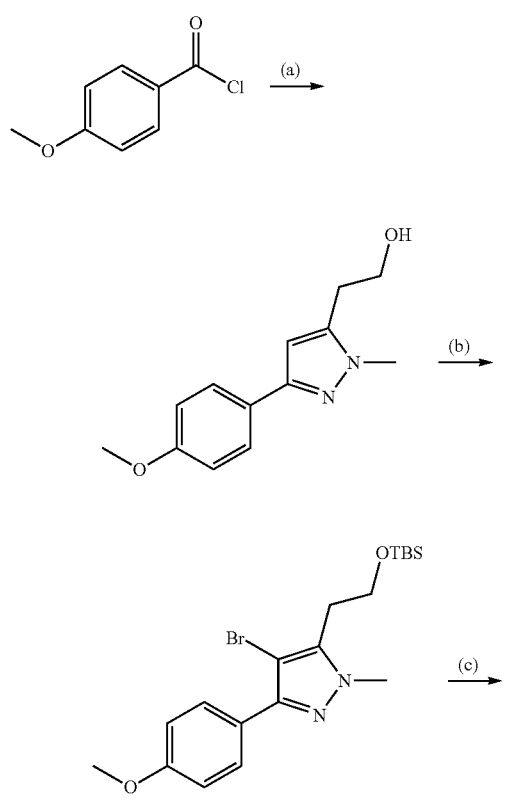

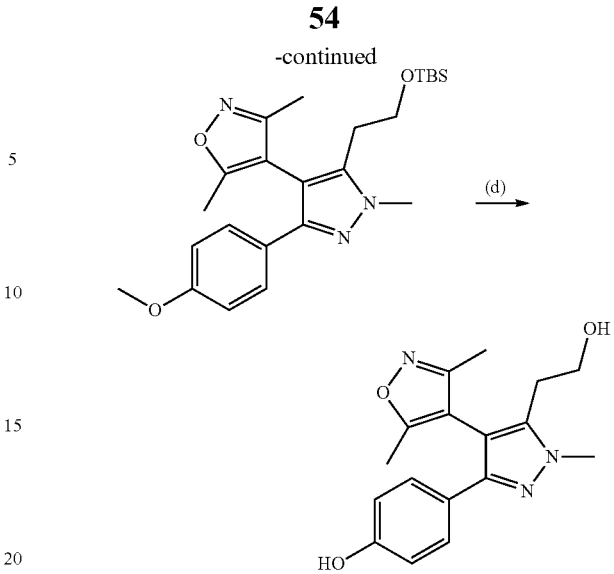

(a) 1) but-3-yn-1-ol, PdCl$_2$(PPh$_3$)$_2$, CuI, TEA, 2) AcOH, MeNHNH$_2$ (MeOH);
(b) 1) NBS (MeCN), 2) TBSOTf, TEA (DCM); (c) 3,5-dimethylisoxazol-4-ylboronic acid, Pd(PPh$_3$)$_4$, K$_2$CO$_3$ (DME/water); (d) BF$_3$*Me$_2$S (DCM)

Step (a): PdCl$_2$(PPh$_3$)$_2$ (14.0 mg, 0.02 mmol) and CuI (7.6 mg, 0.04 mmol) was added to dry THF (2 mL) and degassed. 4-Methoxybenzoic chloride (171 mg, 1.0 mmol), but-3-yn-1-ol (77.1 mg, 1.1 mmol) and triethylamine (292 μL, 1.1 mmol) were added to the mixture and stirred at room temperature for 1 h. Methylhydrazine (50.7 mg, 1.1 mmol) was added to the reaction mixture together with MeOH (0.5 mL) and acetic acid (0.5 mL) and the mixture was irradiated in the microwave at 150° C. for 10 min. The solution was concentrated and purified on silica gel to give 2-(3-(4-methoxyphenyl)-1-methyl-1H-pyrazol-5-yl)ethanol (173 mg, 0.74 mmol, 74%).

Step (b): A solution of 2-(3-(4-methoxyphenyl)-1-methyl-1H-pyrazol-5-yl)ethanol (153 mg, 0.66 mmol) and N-bromosuccinimide (123 mg, 0.69 mmol) in dry MeCN (4 mL) was stirred at 0° C. for 40 min, concentrated and was used without further purification.

The raw product was dissolved in DCM (6 mL) and TEA (183 μL, 1.31 mmol) was added. The mixture was stirred at room temperature for 5 min, then TBSOTf (159 μL, 0.69 mmol) was added at 0° C. and the reaction was stirred at 0° C. for 1 h, concentrated and purified on silica gel to give 4-bromo-5-(2-(tert-butyldimethylsilyloxy)ethyl)-3-(4-methoxyphenyl)-1-methyl-1-H-pyrazole (281 mg, 0.66 mmol, 100%).

Step (c): A mixture of 4-bromo-5-(2-(tert-butyldimethylsilyloxy)ethyl)-3-(4-methoxyphenyl)-1-methyl-1-H-pyrazole (140 mg, 0.33 mmol), 3,5-dimethylisoxazol-4-ylboronic acid (92.8 mg, 0.66 mmol), K$_2$CO$_3$ (328 mg, 2.37 mmol) and Pd(PPh$_3$)$_4$ (19.0 mg, 0.02 mmol) in DME (1 mL) and water (1 mL) was flushed with argon and irradiated in the microwave at 140° C. for 20 min. Full conversion was not achieved. The mixture was filtered to remove palladium black. Irradiation in the microwave was continued until full conversion was achieved. Altogether 3,5-dimethylisoxazol-4-ylboronic acid (233 mg, 1.66 mmol) and Pd(PPh$_3$)$_4$ (57.0 mg, 0.06 mmol) were used and three irradiations were run. Water was added and the crude mixture was extracted with EtOAc. Purification on silica gel gave 4-(5-(2-(tert-butyldimethylsilyloxy)ethyl)-3-(4-methoxyphenyl)-1-methyl-1H-pyrazol-4-yl)-3,5-dimethylisoxazole (34.4 mg, 0.078 mmol, 24%).

Step (d): To a solution of 4-(5-(2-(tert-butyldimethylsilyloxy)ethyl)-3-(4-methoxyphenyl)-1-methyl-1H-pyrazol-4-yl)-3,5-dimethylisoxazole (41.5 mg, 0.094 mmol) in DCM (3 ml) was added BF$_3$.Me2S (1 M solution in DCM, 0.5 mL, 0.5 mmol) and the mixture was stirred at room temperature over night. The DCM layer was discarded and the precipitate was washed with another 0.2 ml DCM. The raw product was purified on silica gel to give 4-(4-(3,5-dimethylisoxazol-4-yl)-5-(2-hydroxyethyl)-1-methyl-1H-pyrazol-3-yl)phenol (28.6 mg, 0.091 mmol, 97%) ES/MS m/z: 314.22 (M+H), 312.31 (M−H); $^1$H NMR (MeOD, 500 MHz): 7.15 (m, 2H), 6.70 (m, 2H), 3.88 (s, 3H), 3.54 (t, 2H, J=6.8 Hz), 2.70 (t, 2H, J=6.8 Hz), 2.16 (s, 3H) and 1.87 (s, 3H).

EXAMPLE 16

4-(2,6-difluorophenyl)-N'-hydroxy-3-(4-hydroxyphenyl)-1-methyl-1H-pyrazole-5-carboximidamide (E16)

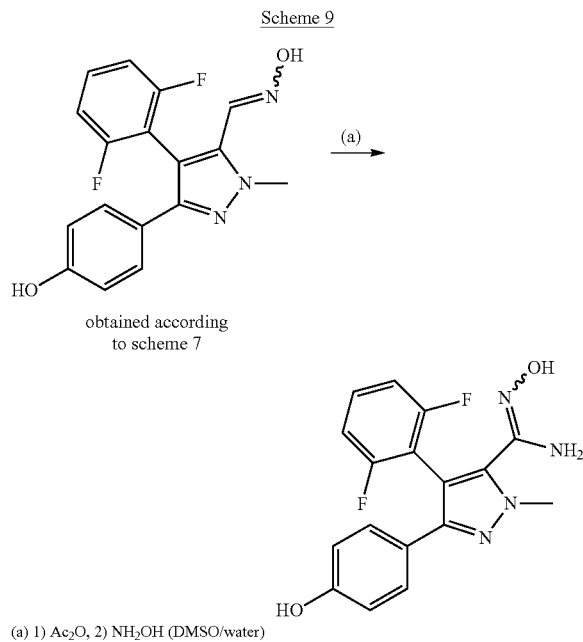

(a) 1) Ac$_2$O, 2) NH$_2$OH (DMSO/water)

Step (a): To 4-(2,6-difluorophenyl)-3-(4-hydroxyphenyl)-1-methyl-1H-pyrazole-5-carbaldehyde oxime (30.0 mg, 0.09 mmol) in acetic anhydride (1 mL) was irradiated in the microwave for 20 min 1.5 ml water was added and the mixture was stirred at rt for 3 h, extracted with DCM, filtered through a phase separator and concentrated. The raw product was dissolved in DMSO (1 mL) and neutral hydroxylamine solution (50 wt % in water, 0.12 mL, 1.96 mmol) was added. The mixture was stirred in the microwave at 130° C. for 10 min. EtOAc and water were added and the phases were separated. The mixture was purified on preparative HPLC to give (Z)-4-(2,6-difluorophenyl)-N'-hydroxy-3-(4-hydroxyphenyl)-1-methyl-1H-pyrazole-5-carboximidamide (5.2 mg, 0.016 mmol, 18%). Identification of the title compound by $^1$H-NMR showed that the oxime product was a single isomer, but did not confirm whether the (E) or (Z) oxime isomer had been obtained. ES/MS m/z: 345.11 (M+H), 343.26 (M−H); $^1$H NMR (MeOD, 500 MHz): 7.37 (m, 1H), 7.15 (m, 2H), 6.96 (m, 2H), 6.65 (m, 2H) and 3.99 (s, 3H).

EXAMPLES 17-42

The following compounds were prepared according to General Methods I, II and III above. Full experimental details of the individual steps of that general method are described in Examples 1, 2, 3, 4, 5 and 6 above.

For each of Examples 18, 19, 20, 23, 24, 25, 27, and 30-42, identification of the title compound by $^1$H-NMR showed that the oxime product was a single isomer, but did not confirm whether the (E) or (Z) oxime isomer had been obtained. For each of Examples 21, 22, 26, 28 and 29, identification of the title compound by $^1$H-NMR showed that the product was an approximately 1:1 mixture of the (E) and (Z) oxime isomers.

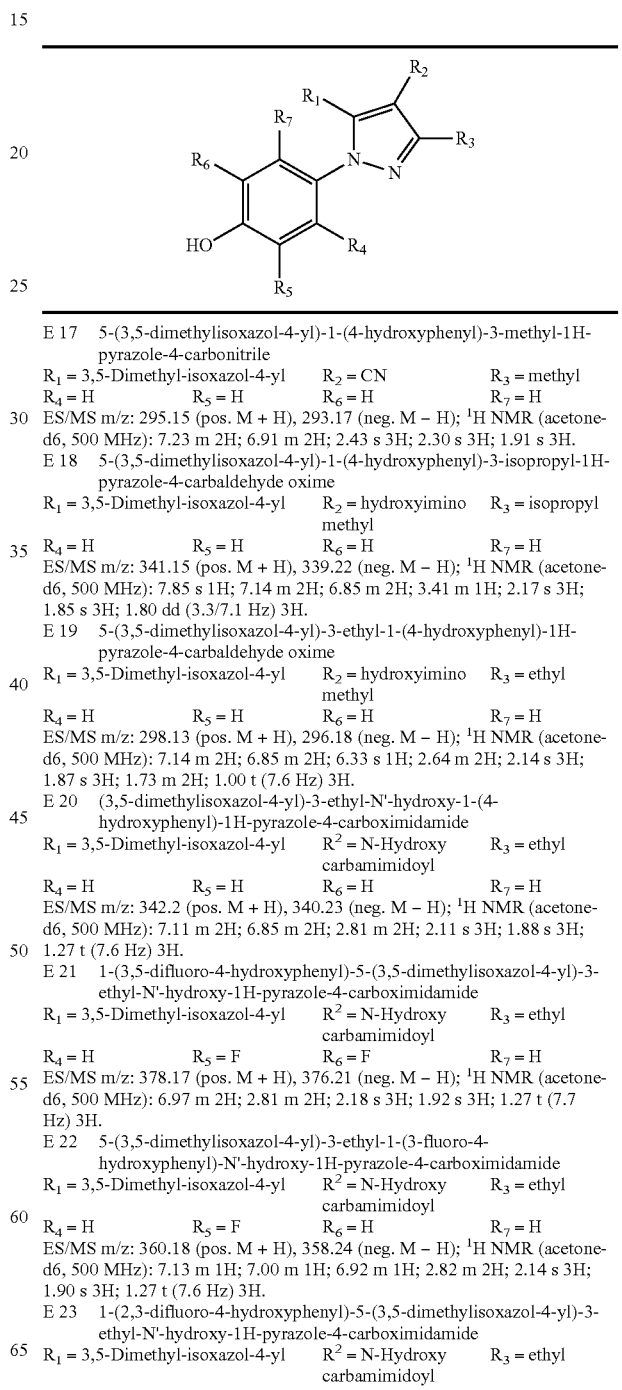

E 17 5-(3,5-dimethylisoxazol-4-yl)-1-(4-hydroxyphenyl)-3-methyl-1H-pyrazole-4-carbonitrile
$R_1$ = 3,5-Dimethyl-isoxazol-4-yl   $R_2$ = CN   $R_3$ = methyl
$R_4$ = H   $R_5$ = H   $R_6$ = H   $R_7$ = H
ES/MS m/z: 295.15 (pos. M + H), 293.17 (neg. M − H); $^1$H NMR (acetone-d6, 500 MHz): 7.23 m 2H; 6.91 m 2H; 2.43 s 3H; 2.30 s 3H; 1.91 s 3H.

E 18 5-(3,5-dimethylisoxazol-4-yl)-1-(4-hydroxyphenyl)-3-isopropyl-1H-pyrazole-4-carbaldehyde oxime
$R_1$ = 3,5-Dimethyl-isoxazol-4-yl   $R_2$ = hydroxyimino methyl   $R_3$ = isopropyl
$R_4$ = H   $R_5$ = H   $R_6$ = H   $R_7$ = H
ES/MS m/z: 341.15 (pos. M + H), 339.22 (neg. M − H); $^1$H NMR (acetone-d6, 500 MHz): 7.85 s 1H; 7.14 m 2H; 6.85 m 2H; 3.41 m 1H; 2.17 s 3H; 1.85 s 3H; 1.80 dd (3.3/7.1 Hz) 3H.

E 19 5-(3,5-dimethylisoxazol-4-yl)-3-ethyl-1-(4-hydroxyphenyl)-1H-pyrazole-4-carbaldehyde oxime
$R_1$ = 3,5-Dimethyl-isoxazol-4-yl   $R_2$ = hydroxyimino methyl   $R_3$ = ethyl
$R_4$ = H   $R_5$ = H   $R_6$ = H   $R_7$ = H
ES/MS m/z: 298.13 (pos. M + H), 296.18 (neg. M − H); $^1$H NMR (acetone-d6, 500 MHz): 7.14 m 2H; 6.85 m 2H; 6.33 s 1H; 2.64 m 2H; 2.14 s 3H; 1.87 s 3H; 1.73 m 2H; 1.00 t (7.6 Hz) 3H.

E 20 (3,5-dimethylisoxazol-4-yl)-3-ethyl-N'-hydroxy-1-(4-hydroxyphenyl)-1H-pyrazole-4-carboximidamide
$R_1$ = 3,5-Dimethyl-isoxazol-4-yl   $R^2$ = N-Hydroxy carbamimidoyl   $R_3$ = ethyl
$R_4$ = H   $R_5$ = H   $R_6$ = H   $R_7$ = H
ES/MS m/z: 342.2 (pos. M + H), 340.23 (neg. M − H); $^1$H NMR (acetone-d6, 500 MHz): 7.11 m 2H; 6.85 m 2H; 2.81 m 2H; 2.11 s 3H; 1.88 s 3H; 1.27 t (7.6 Hz) 3H.

E 21 1-(3,5-difluoro-4-hydroxyphenyl)-5-(3,5-dimethylisoxazol-4-yl)-3-ethyl-N'-hydroxy-1H-pyrazole-4-carboximidamide
$R_1$ = 3,5-Dimethyl-isoxazol-4-yl   $R^2$ = N-Hydroxy carbamimidoyl   $R_3$ = ethyl
$R_4$ = H   $R_5$ = F   $R_6$ = F   $R_7$ = H
ES/MS m/z: 378.17 (pos. M + H), 376.21 (neg. M − H); $^1$H NMR (acetone-d6, 500 MHz): 6.97 m 2H; 2.81 m 2H; 2.18 s 3H; 1.92 s 3H; 1.27 t (7.7 Hz) 3H.

E 22 5-(3,5-dimethylisoxazol-4-yl)-3-ethyl-1-(3-fluoro-4-hydroxyphenyl)-N'-hydroxy-1H-pyrazole-4-carboximidamide
$R_1$ = 3,5-Dimethyl-isoxazol-4-yl   $R^2$ = N-Hydroxy carbamimidoyl   $R_3$ = ethyl
$R_4$ = H   $R_5$ = F   $R_6$ = H   $R_7$ = H
ES/MS m/z: 360.18 (pos. M + H), 358.24 (neg. M − H); $^1$H NMR (acetone-d6, 500 MHz): 7.13 m 1H; 7.00 m 1H; 6.92 m 1H; 2.82 m 2H; 2.14 s 3H; 1.90 s 3H; 1.27 t (7.6 Hz) 3H.

E 23 1-(2,3-difluoro-4-hydroxyphenyl)-5-(3,5-dimethylisoxazol-4-yl)-3-ethyl-N'-hydroxy-1H-pyrazole-4-carboximidamide
$R_1$ = 3,5-Dimethyl-isoxazol-4-yl   $R^2$ = N-Hydroxy carbamimidoyl   $R_3$ = ethyl

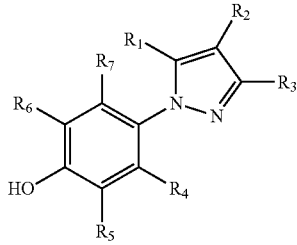
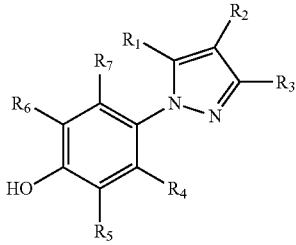

| $R_4$ = F | $R_5$ = F | $R_6$ = H | $R_7$ = H |
|---|---|---|---|

ES/MS m/z: 378.19 (pos. M + H), 376.2 (neg. M − H); $^1$H NMR (acetone-d6, 500 MHz): 7.13 m 1H; 6.93 m 1H; 2.95 m 2H; 2.11 s 3H; 1.98 s 3H; 1.27 t (7.5 Hz) 3H.

E 24 5-(3,5-dimethylisoxazol-4-yl)-3-ethyl-1-(2-fluoro-4-hydroxyphenyl)-N'-hydroxy-1H-pyrazole-4-carboximidamide

| $R_1$ = 3,5-Dimethyl-isoxazol-4-yl | $R^2$ = N-Hydroxy carbamimidoyl | $R_3$ = ethyl |
|---|---|---|
| $R_4$ = F | $R_5$ = H | $R_6$ = H | $R_7$ = H |

ES/MS m/z: 360.24 (pos. M + H), 358.27 (neg. M − H); $^1$H NMR (acetone-d6, 500 MHz): 7.30 t (8.8 Hz) 1H; 6.76 m 1H; 6.65 m 1H; 2.82 q (7.49 Hz) 2H; 2.09 s 3H; 1.97 s 3H; 1.26 t (7.49 Hz) 3H E 25 (E) or (Z)-1-(2,3-difluoro-4-hydroxyphenyl)-5-(3,5-dimethylisoxazol-4-yl)-3-ethyl-1H-pyrazole-4-carbaldehyde oxime

| $R_1$ = 3,5-Dimethyl-isoxazol-4-yl | $R^2$ = hydroxyimino methyl | $R_3$ = ethyl |
|---|---|---|
| $R_4$ = F | $R_5$ = F | $R_6$ = H | $R_7$ = H |

ES/MS m/z: 363.21 (pos. M + H), 361.23 (neg. M − H); $^1$H NMR (acetone-d6, 500 MHz): 7.25 s 1H; 7.15 m 1H; 6.93 m 1H; (missing m 2H under H2O); 2.14 s 3H; 1.93 s 3H; 1.26 t (7.6 Hz) 3H.

E 26 (E) or (Z)-1-(2,3-difluoro-4-hydroxyphenyl)-5-(3,5-dimethylisoxazol-4-yl)-3-ethyl-1H-pyrazole-4-carbaldehyde oxime

| $R_1$ = 3,5-Dimethyl-isoxazol-4-yl | $R^2$ = hydroxyimino methyl | $R_3$ = ethyl |
|---|---|---|
| $R_4$ = F | $R_5$ = F | $R_6$ = H | $R_7$ = H |

ES/MS m/z: 363.2 (pos. M + H), 361.25 (neg. M − H); $^1$H NMR (acetone-d6, 500 MHz): 7.86 s 1H; 7.15 m 1H; 6.92 m 1H; 2.87 m 2H; 2.17 s 3H; 1.97 s 3H; 1.27 t (7.7 Hz) 3H.

E 27 5-(3,5-dimethylisoxazol-4-yl)-3-ethyl-1-(2-fluoro-4-hydroxyphenyl)-1H-pyrazole-4-carbaldehyde oxime

| $R_1$ = 3,5-Dimethyl-isoxazol-4-yl | $R^2$ = hydroxyimino methyl | $R_3$ = ethyl |
|---|---|---|
| $R_4$ = F | $R_5$ = H | $R_6$ = H | $R_7$ = H |

ES/MS m/z: 345.16 (pos. M + H), 343.24 (neg. M − H); $^1$H NMR (acetone-d6, 500 MHz): 7.85 s 1H; 7.35 m 1H; 6.77 m 1H; 6.66 m 1H; 2.86 m 2H; 2.14 s 3H; 1.95 s 3H; 1.27 t (7.8 Hz) 3H.

E 28 1-(3,5-difluoro-4-hydroxyphenyl)-5-(3,5-dimethylisoxazol-4-yl)-3-ethyl-1H-pyrazole-4-carbaldehyde oxime

| $R_1$ = 3,5-Dimethyl-isoxazol-4-yl | $R^2$ = hydroxyimino methyl | $R_3$ = ethyl |
|---|---|---|
| $R_4$ = H | $R_5$ = F | $R_6$ = F | $R_7$ = H |

ES/MS m/z: 363.19 (pos. M + H), 361.22 (neg. M − H); $^1$H NMR (acetone-d6, 500 MHz): 7.83 s 1H; 7.00 2H; 2.86 m 2H; 2.25 s 3H; 1.91 s 3H; 1.28 t (7.5 Hz) 3H.

E 29 1-(2,5-difluoro-4-hydroxyphenyl)-5-(3,5-dimethylisoxazol-4-yl)-3-ethyl-N'-hydroxy-1H-pyrazole-4-carboximidamide

| $R_1$ = 3,5-Dimethyl-isoxazol-4-yl | $R^2$ = N-Hydroxy carbamimidoyl | $R_3$ = ethyl |
|---|---|---|
| $R_4$ = H | $R_5$ = F | $R_6$ = H | $R_7$ = F |

ES/MS m/z: 378.17 (pos. M + H), 376.21 (neg. M − H); $^1$H NMR (acetone-d6, 500 MHz): 7.32 m 1H; 6.87 m 1H; 2.82 m 2H; 2.11 s 3H; 1.99 s 3H; 1.26 t (7.6 Hz) 3H.

E 30 1-(2,5-difluoro-4-hydroxyphenyl)-5-(3,5-dimethylisoxazol-4-yl)-3-ethyl-1H-pyrazole-4-carbaldehyde oxime

| $R_1$ = 3,5-Dimethyl-isoxazol-4-yl | $R^2$ = hydroxyimino methyl | $R_3$ = ethyl |
|---|---|---|
| $R_4$ = H | $R_5$ = F | $R_6$ = H | $R_7$ = F |

ES/MS m/z: 363.13 (pos. M + H), 361.21 (neg. M − H); $^1$H NMR (acetone-d6, 500 MHz): 7.85 s 1H; 7.39 s 1H; 6.86 m 1H; 2.86 m 2H; 2.16 s 3H; 1.97 s 3H; 1.28 t (7.4 Hz) 3H.

E 31 5-(3,5-dimethylisoxazol-4-yl)-1-(2-fluoro-4-hydroxyphenyl)-N'-hydroxy-3-methyl-1H-pyrazole-4-carboximidamide

| $R_1$ = 3,5-Dimethyl-isoxazol-4-yl | $R^2$ = N-Hydroxy carbamimidoyl | $R_3$ = methyl |
|---|---|---|
| $R_4$ = F | $R_5$ = H | $R_6$ = H | $R_7$ = H |

ES/MS m/z: 346.19 (pos. M + H), 344.25 (neg. M − H); $^1$H NMR (acetone-d6, 500 MHz): 7.29 (t, 1H, J = 8.7 Hz), 6.76 (m, 1H) and 6.65 (dd, 1H, J = 12.0, 2.6 Hz), 2.37 (s, 3H), 2.09 (s, 3H) and 1.98 (s, 3H).

E 32 5-(3,5-dimethylisoxazol-4-yl)-1-(2-fluoro-4-hydroxyphenyl)-N'-hydroxy-3-propyl-1H-pyrazole-4-carboximidamide

| $R_1$ = 3,5-Dimethyl-isoxazol-4-yl | $R^2$ = N-Hydroxy carbamimidoyl | $R_3$ = propyl |
|---|---|---|
| $R_4$ = F | $R_5$ = H | $R_6$ = H | $R_7$ = H |

ES/MS m/z: 374.2 (pos. M + H), 372.22 (neg. M − H); $^1$H NMR (acetone-d6, 500 MHz): 7.29 (t, 1H, J = 8.3 Hz), 6.76 (m, 1H), 6.65 (dd, 1H, J = 11.9, 2.6 Hz), 2.77 (m, 2H), 2.09 (s, 3H), 1.97 (s, 3H), 1.74 (m, 2H) and 0.97 (t, 3H, J 07.3 Hz).

E 33 5-(3,5-dimethylisoxazol-4-yl)-1-(2-fluoro-4-hydroxyphenyl)-3-methyl-1H-pyrazole-4-carbaldehyde oxime

| $R_1$ = 3,5-Dimethyl-isoxazol-4-yl | $R^2$ = hydroxyimino methyl | $R_3$ = methyl |
|---|---|---|
| $R_4$ = F | $R_5$ = H | $R_6$ = H | $R_7$ = H |

ES/MS m/z: 331.24 (pos. M + H), 329.21 (neg. M − H); $^1$H NMR (acetone-d6, 500 MHz): 7.34 (t, 1H, J = 8.8 Hz), 6.77 (m, 1H), 6.66 (dd, 1H, J = 12.1, 2.7 Hz), 2.41 (s, 3H), 2.14 (s, 3H) and 1.96 (s, 3H).

E 34 1-(2,3-difluoro-4-hydroxyphenyl)-3-ethyl-5-(1-methyl-1H-pyrrol-2-yl)-1H-pyrazole-4-carbaldehyde oxime

| $R_1$ = 1-methyl-1H-pyrrol-2-yl | $R^2$ = hydroxyimino methyl | $R_3$ = ethyl |
|---|---|---|
| $R_4$ = F | $R_5$ = F | $R_6$ = H | $R_7$ = H |

ES/MS m/z: 347.23 (pos. M + H), 345.21 (neg. M − H); $^1$H NMR (acetone-d6, 500 MHz): 7.80 (s, 1H), 7.07 (s, 1H), 6.86 (m, 1H), 6.81 (t, 1H, J = 2.3 Hz), 6.05 (m, 2H), 3.40 (s, 3H), 2.88 (q, 2H, J = 7.6 Hz) and 1.27 (t, 3H, J = 7.6 Hz).

E 35 2-(2-fluoro-4-hydroxyphenyl)-2',4',5-trimethyl-2H,2'H-3,3'-bipyrazole-4-carbaldehyde oxime

| $R_1$ = 1,4-dimethyl-1H-pyrazole-5yl | $R^2$ = hydroxyimino methyl | $R_3$ = methyl |
|---|---|---|
| $R_4$ = F | $R_5$ = H | $R_6$ = H | $R_7$ = H |

ES/MS m/z: 330.24 (pos. M + H), 328.28 (neg. M − H); $^1$H NMR (acetone-d6, 500 MHz): 7.76 (s, 1H), 7.27 (t, 1H, J = 8.9 Hz), 7.21 (s, 1H), 6.73 (m, 1H), 6.64 (dd, 1H, J = 12.0, 2.5 Hz), 3.56 (s, 3H), 2.44 (s, 3H) and 1.73 (s, 3H).

E 36 2-(2-fluoro-4-hydroxyphenyl)-N'-hydroxy-2',4',5-trimethyl-2H,2'H-3,3'-bipyrazole-4-carboximidamide

| $R_1$ = 1,4-dimethyl-1H-pyrazole-5yl | $R^2$ = N-Hydroxy carbamimidoyl | $R_3$ = methyl |
|---|---|---|
| $R_4$ = F | $R_5$ = H | $R_6$ = H | $R_7$ = H |

ES/MS m/z: 345.22 (pos. M + H), 343.28 (neg. M − H); $^1$H NMR (acetone-d6, 500 MHz): 7.22 (t, 1H, J = 8.8 Hz), 7.14 (s, 1H), 6.70 (m, 1H), 6.62 (dd, 1H, J = 12.0, 2.6 Hz), 3.61 (s, 3H), 2.40 (s, 3H) and 1.70 (s, 3H).

E 37 5-(2,6-dimethylphenyl)-1-(2-fluoro-4-hydroxyphenyl)-N'-hydroxy-3-methyl-1H-pyrazole-4-carboximidamide

| $R_1$ = 2,6-dimethylphenyl | $R^2$ = N-Hydroxy carbamimidoyl | $R_3$ = methyl |
|---|---|---|
| $R_4$ = F | $R_5$ = H | $R_6$ = H | $R_7$ = H |

ES/MS m/z: 355.18 (pos. M + H), 353.21 (neg. M − H); $^1$H NMR (acetone-d6, 500 MHz): 7.14 (t, 1H, J = 7.7 Hz), 7.08 (t, 1H, J = 8.6 Hz), 7.01 (m, 2H), 6.58 (m, 2H), 2.40 (s, 3H) and 2.07 (s, 6H).

E 38 5-(2,5-dimethyl-1H-pyrrol-1-yl)-3-ethyl-N'-hydroxy-1-(4-hydroxyphenyl)-1H-pyrazole-4-carboximidamide

| $R_1$ = 2,5-dimethyl-1H-pyrrol-1-yl | $R^2$ = N-Hydroxy carbamimidoyl | $R_3$ = ethyl |
|---|---|---|
| $R_4$ = H | $R_5$ = H | $R_6$ = H | $R_7$ = H |

ES/MS m/z: 340.19 (pos. M + H), 338.22 (neg. M − H); $^1$H NMR (acetone-d6, 500 MHz): 6.92 (m, 2H), 6.78 (m, 2H), 5.87 (s, 2H), 2.88 (q, 2H, J = 7.4 Hz), 1.91 (s, 6H) and 1.28 (t, 3H, J = 7.4 Hz).

E 39 5-(2,6-dimethylphenyl)-1-(2-fluoro-4-hydroxyphenyl)-3-methyl-1H-pyrazole-4-carbaldehyde oxime

| $R_1$ = 2,6-dimethylphenyl | $R^2$ = hydroxyimino methyl | $R_3$ = methyl |
|---|---|---|

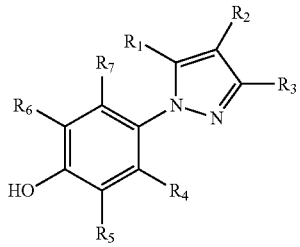

R₄ = F    R₅ = H    R₆ = H    R₇ = H
ES/MS m/z: 340.16 (pos. M + H), 338.2 (neg. M − H); ¹H NMR (acetone-d6, 500 MHz): 7.58 (s, 1H), 7.19 (t, 1H, J = 7.7 Hz), 7.14 (t, 1H, J = 8.9 Hz), 7.06 (m, 2H), 6.63 (m, 1H), 6.59 (dd, 1H, J = 12.1, 2.6 Hz), 2.44 (s, 3H) and 2.03 (s, 6H).

E 40    5-(2,5-dimethyl-1H-pyrrol-1-yl)-1-(3-fluoro-4-hydroxyphenyl)-N'-hydroxy-3-methyl-1H-pyrazole-4-carboximidamide
R₁ = 2,5-dimethyl-1H-pyrrol-1-yl    R² = N-Hydroxy carbamimidoyl    R₃ = methyl
R₄ = H    R₅ = F    R₆ = H    R₇ = H
ES/MS m/z: 344.13 (pos. M + H), 342.2 (neg. M − H); ¹H NMR (acetone-d6, 500 MHz): 6.95 (t, 1H, J = 8.9 Hz), 6.73 (m, 2H), 5.93 (s, 2H), 2.42 (s, 3H) and 1.92 (s, 6H).

E 41    1-(2,3-difluoro-4-hydroxyphenyl)-5-(2,5-dimethyl-1H-pyrrol-1-yl)-N'-hydroxy-3-methyl-1H-pyrazole-4-carboximidamide
R₁ = 2,5-dimethyl-1H-pyrrol-1-yl    R² = N-Hydroxy carbamimidoyl    R₃ = methyl
R₄ = F    R₅ = F    R₆ = H    R₇ = H
ES/MS m/z: 362.11 (pos. M + H), 360.16 (neg. M − H); ¹H NMR (acetone-d6, 500 MHz): 6.90 (m, 2H), 5.78 (m, 2H), 2.42 (s, 3H) and 1.96 (s, 6H).

E 42    1-(3,5-difluoro-4-hydroxyphenyl)-5-(2,5-dimethyl-1H-pyrrol-1-yl)-N'-hydroxy-3-methyl-1H-pyrazole-4-carboximidamide
R₁ = 2,5-dimethyl-1H-pyrrol-1-yl    R² = N-Hydroxy carbamimidoyl    R₃ = methyl
R₄ = H    R₅ = F    R₆ = F    R₇ = H
ES/MS m/z: 362.16 (pos. M + H), 360.22 (neg. M − H); ¹H NMR (acetone-d6, 500 MHz): 6.57 (m, 2H), 5.98 (s, 2H), 2.43 (s, 3H) and 1.93 (s, 6H).

EXAMPLES 43-50

The following compounds were prepared according to General Methods V and VI above. Full experimental details of the individual steps of that general method are described in Examples 11, 12, 13 and 14 above.

For each of Examples 44, 45, 47, 48 and 50, identification of the title compound by ¹H-NMR showed that the oxime product was a single isomer, but did not confirm whether the (E) or (Z) oxime isomer had been obtained.

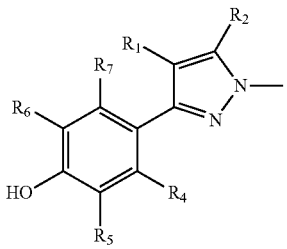

E 43    3-(3-chloro-4-hydroxyphenyl)-4-(3,5-dimethylisoxazol-4-yl)-1-methyl-1H-pyrazole-5-carboxamide
R₁ = 3,5-dimethylisoxazol-4-yl    R² = N-Hydroxy carbamimidoyl
R₄ = H    R₅ = Cl    R₆ = H    R₇ = H
ES/MS m/z: 347, 349.1 (pos. M + H), 345.1, 346.9 (neg. M − H); ¹H NMR (acetone-d6, 500 MHz): 7.49 (d, 1H, J = 2.2 Hz), 7.13 (dd, 1H, J = 8.6, 2.2 Hz), 6.96 (d, 1H, J = 8.6 Hz), 4.12 (s, 3H), 2.14 (s, 3H) and 1.95 (s, 3H).

E 44    4-(2,6-difluorophenyl)-3-(4-hydroxyphenyl)-1-methyl-1H-pyrazole-5-carbaldehyde oxime

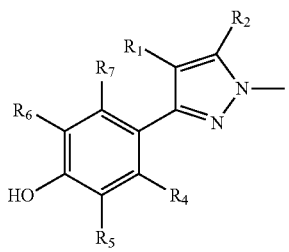

R₁ = 2,6-difluorophenyl    R² = hydroxyimino methyl
R₄ = H    R₅ = H    R₆ = H    R₇ = H
ES/MS m/z: 330.07 (pos. M + H), 328.07 (neg. M − H); ¹H NMR (acetone-d6, 500 MHz): 7.92 (s, 1H), 7.51 (m, 1H), 7.27 (m, 2H), 7.10 (m, 2H), 6.74 (m, 2H) and 4.11 (s, 3H).

E 45    4-(2,6-dichlorophenyl)-3-(4-hydroxyphenyl)-1-methyl-1H-pyrazole-5-carbaldehyde oxime
R₁ = 2,6-dichlorophenyl    R² = hydroxyimino methyl
R₄ = H    R₅ = H    R₆ = H    R₇ = H
ES/MS m/z: 362.6, 364.4 (pos. M + H), 362.5, 360.1 (neg. M − H); ¹H NMR (acetone-d6, 500 MHz): 7.81 (s, 1H), 7.53 (m, 2H), 7.46 (m, 2H), 7.23 (m, 2H), 6.71 (m, 2H) and 4.12 (s, 3H).

E 46    4-(2,6-dichlorophenyl)-3-(4-hydroxyphenyl)-1-methyl-1H-pyrazole-5-carboxamide
R₁ = 2,6-dichlorophenyl    R² = carboxamide
R₄ = H    R₅ = H    R₆ = H    R₇ = H
ES/MS m/z: 362.02, 364.00 (pos. M + H), 360.05, 362.11 (neg. M − H); ¹H NMR (acetone-d6, 500 MHz): 7.57 (m, 2H), 7.49 (dd, 1H, J = 9.0, 7.4 Hz), 7.18 (m, 2H), 6.71 (m, 2H) and 4.17 (s, 3H).

E 47    4-(2,6-dichlorophenyl)-N'-hydroxy-3-(4-hydroxyphenyl)-1-methyl-1H-pyrazole-5-carboximidamide
R₁ = 2,6-dichlorophenyl    R² = N-Hydroxy carbamimidoyl
R₄ = H    R₅ = H    R₆ = H    R₇ = H
ES/MS m/z: 377.01, 379.04 (pos. M + H); ¹H NMR (acetone-d6, 500 MHz): 7.48 (m, 2H), 7.40 (dd, 1H, J = 9.0, 7.2 Hz), 7.21 (m, 2H), 6.70 (m, 2H) and 4.01 (s, 3H).

E 48    4-(3,5-dimethylisoxazol-4-yl)-3-(2-fluoro-4-hydroxyphenyl)-1-methyl-1H-pyrazole-5-carbaldehyde oxime
R₁ = 3,5-dimethylisoxazol-4-yl    R² = hydroxyimino methyl
R₄ = F    R₅ = H    R₆ = H    R₇ = H
ES/MS m/z: 331.06 (pos. M + H), 329.17 (neg. M − H); ¹H NMR (acetone-d6, 500 MHz): 7.99 (s, 1H), 7.24 (t, 1H, J = 8.5 Hz), 6.70 (dd, 1H, J = 8.5, 2.4 Hz), 6.55 (dd, 1H, J = 11.9, 2.4 Hz), 4.10 (s, 3H), 2.05 (s, 3H) and 1.87 (s, 3H).

E 49    4-(3,5-dimethylisoxazol-4-yl)-3-(2-fluoro-4-hydroxyphenyl)-1-methyl-1H-pyrazole-5-carboxamide
R₁ = 3,5-dimethylisoxazol-4-yl    R² = carboxamide
R₄ = F    R₅ = H    R₆ = H    R₇ = H
ES/MS m/z: 331.07 (pos. M + H), 329.13 (neg. M − H); ¹H NMR (acetone-d6, 500 MHz): 7.21 (t, 1H, J = 8.6 Hz), 6.70 (dd, 1H, J = 8.6, 2.4 Hz), 6.55 (dd, 1H, J = 11.8, 2.4 Hz), 4.13 (s, 3H), 2.02 (s, 3H) and 1.93 (s, 3H).

E 50    4-(3,5-dimethylisoxazol-4-yl)-3-(2-fluoro-4-hydroxyphenyl)-N'-hydroxy-1-methyl-1H-pyrazole-5-carboximidamide
R₁ = 3,5-dimethylisoxazol-4-yl    R² = N-Hydroxy carbamimidoyl
R₄ = F    R₅ = H    R₆ = H    R₇ = H
ES/MS m/z: 346.09 (pos. M + H), 344.17 (neg. M − H); ¹H NMR (acetone-d6, 500 MHz): 7.22 (t, 1H, J = 8.5 Hz), 6.71 (dd, 1H, J = 8.5, 2.4 Hz), 6.57 (dd, 1H, J = 11.9, 2.4 Hz), 4.00 (s, 3H), 2.03 (s, 3H) and 1.91 (s, 3H).

EXAMPLE 51 AND 52

5-((Z)-but-2-en-2-yl)-1-(2-fluoro-4-hydroxyphenyl)-N'-hydroxy-3-methyl-1H-pyrazole-4-carboximidamide (E51)

5-(2,4-dimethylthiophen-3-yl)-1-(2-fluoro-4-hydroxyphenyl)-N'-hydroxy-3-methyl-1H-pyrazole-4-carboximidamide (E52)

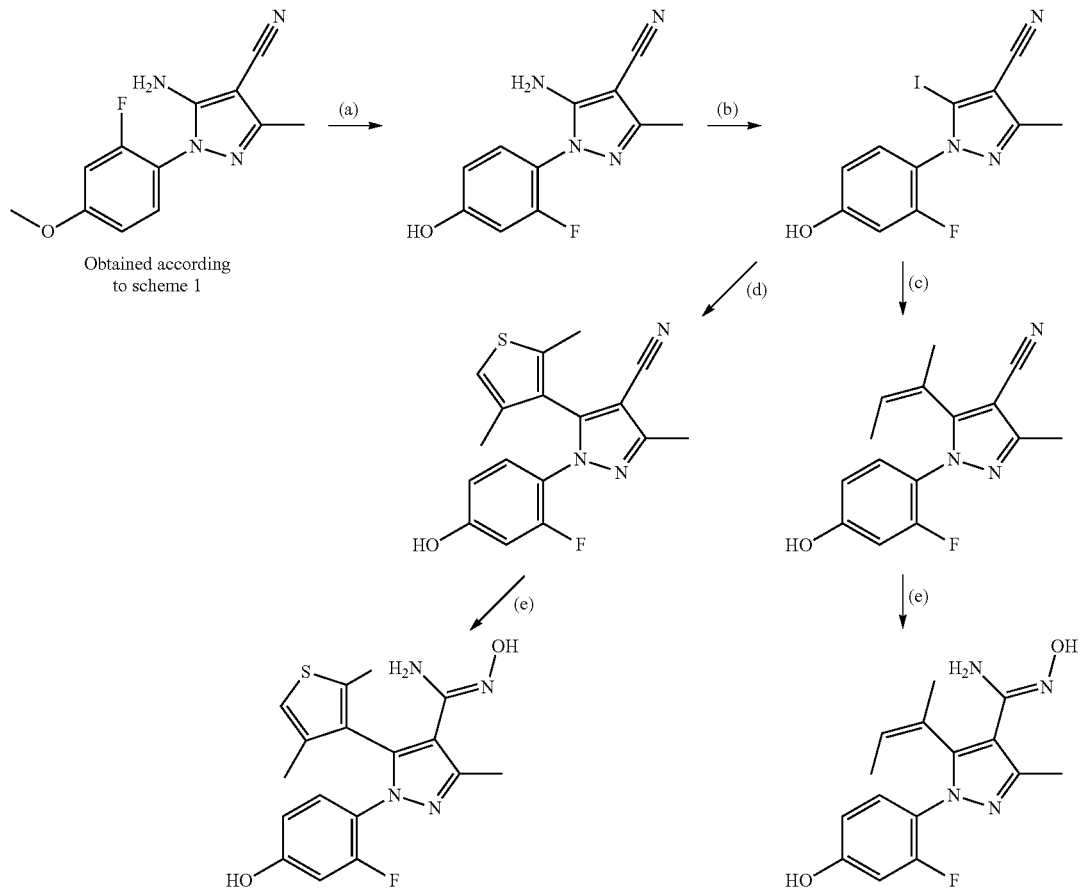

(a) BBr₃ (CH₂Cl₂); (b) isoamyl nitrite, diiodomethane (MeCN); (c) Pd(PPh₃)₄, (E)-but-2-en-2-ylboronic acid, K₂CO₃ (DME/H₂O); PdCl₂(PPh₃)₂, tributyl(2,4-dimethylthiophen-3-yl)stannane (DME/dioxane); (e) NH₂OH (MeOH/water)

Step (a): 5-amino-1-(2-fluoro-4-methoxyphenyl)-3-methyl-1H-pyrazole-4-carbonitrile (256 mg, 1.0 mmol) was dissolved in CH₂Cl₂ (25 mL) and BBr₃ (1 M solution in DCM, 4.91 mL, 4.91 mmol) was added and stirred at room temperature over night. The reaction was quenched using water, extracted with CH₂Cl₂ and dried using a phase separator. Concentration gave 5-amino-1-(2-fluoro-4-hydroxyphenyl)-3-methyl-1H-pyrazole-4-carbonitrile (232.1 mg, 100%) which was used as such in the next step.

Step (b): To a stirred solution of 5-amino-1-(2-fluoro-4-hydroxyphenyl)-3-methyl-1H-pyrazole-4-carbonitrile (114 mg, 0.49 mmol) in MeCN (2.5 mL) was added diiodomethane (0.293 mL, 3.63 mmol) followed by isoamyl nitrite (0.029 mL, 0.216 mmol). The reaction vessel was heated using a heating gun to initiate the reaction. After the rest of isoamyl nitrite (0.261 mL, 1.94 mmol) was added and the reaction was stirred for 1 hour at 50° C. The reaction was diluted with DCM and concentrated into silica and purified using silica gel (Heptane-EtOAc 1:0 to 0:1) to give 1-(2-fluoro-4-hydroxyphenyl)-5-iodo-3-methyl-1H-pyrazole-4-carbonitrile (90.0 mg, 53%).

Step (c): A mixture of 1-(2-fluoro-4-hydroxyphenyl)-5-iodo-3-methyl-1H-pyrazole-4-carbonitrile (40 mg, 0.12 mmol), (E)-but-2-en-2-ylboronic acid (23.3 mg, 0.23 mmol), K₂CO₃ (96.7 mg, 0.70 mmol) and Pd(PPh₃)₄ (13.47 mg, 0.01 mmol) in DME (1 mL) and water (1 mL) was flushed with N₂ and irradiated in the microwave at 150° C. for 10 min. Water and DCM were added and the phases were separated. The organic layer was concentrated and the crude product was purified on HPLC to give (Z)-5-(but-2-en-2-yl)-1-(2-fluoro-4-hydroxyphenyl)-3-methyl-1H-pyrazole-4-carbonitrile (23.0 mg, 73%).

Step (d): 1-(2-fluoro-4-hydroxyphenyl)-5-iodo-3-methyl-1H-pyrazole-4-carbonitrile (40 mg, 0.12 mmol), tributyl(2,4-dimethylthiophen-3-yl)stannane (140.3 mg, 0.35 mmol) and PdCl₂(PPh₃)₂ (24.55 mg, 0.03 mmol), were mixed with 0.5 mL degassed dioxane and 0.5 mL degassed DME under nitrogen in a microwave vial. The reaction was run at 145° C. in the microwave for 30 min. Water was added, the mixture was extracted with CH₂Cl₂ and the organic layer was concentrated. The crude product was purified on HPLC to give 5-(2,4-dimethylthiophen-3-yl)-1-(2-fluoro-4-hydroxyphenyl)-3-methyl-1H-pyrazole-4-carbonitrile (13 mg, 34%).

Step (e): Hydroxylamine (50 wt % solution in water, 0.5 mL, 8.11 mmol) was added to (Z)-5-(but-2-en-2-yl)-1-(2-fluoro-4-hydroxyphenyl)-3-methyl-1H-pyrazole-4-carbonitrile (22 mg, 0.08 mmol) dissolved in MeOH (1.0 mL) or Hydroxylamine (50 wt % solution in water, 0.24 mL, 3.97 mmol) was added to 5-(2,4-dimethylthiophen-3-yl)-1-(2-fluoro-4-hydroxyphenyl)-3-methyl-1H-pyrazole-4-carbonitrile (13 mg, 0.04 mmol) dissolved in MeOH (0.8 mL). The reaction was heated at 150° C. in the microwave for 15 min. Purification using preparative HPLC gave 5-((Z)-but-2-en-2-yl)-1-(2-fluoro-4-hydroxyphenyl)-N-hydroxy-3-methyl-1H-pyrazole-4-carboximidamide (E51) (11.44 mg, 46%), ES/MS m/z: 305.08 (M+H), 303.13 (M−H); $^1$H NMR (acetone-d6, 500 MHz): 7.22 (m, 1H), 6.76-6.71 (m, 2H), 5.65 (m, 1H), 2.30 (s, 3H), 1.83 (s, 3H) and 1.39 (d, 3H, J=6.7 Hz) or 5-(2,4-dimethylthiophen-3-yl)-1-(2-fluoro-4-hydroxyphenyl)-N'-hydroxy-3-methyl-1H-pyrazole-4-carboximidamide (E52) (4.31 mg, 30%) ES/MS m/z: 361.05 (M+H), 359.17 (M−H); $^1$H NMR (acetone-d6, 500 MHz): 7.14 (t, 1H, J=8.8 Hz), 6.83 (q, 1H, J=1.0 Hz), 6.66 (m, 1H), 6.61 (dd, 1H, J=11.9, 2.7 Hz), 2.38 (s, 3H), 2.16 (s, 3H) and 1.94 (d, 3H, J=1.0 Hz).

Identification of the title compounds by $^1$H-NMR showed that the oxime product was a single isomer, but did not confirm whether the (E) or (Z) oxime isomer had been obtained.

EXAMPLE 53-57

The following compounds were prepared according to General Methods I, III and VIII above. Full experimental details of the individual steps of that general method are described in Examples 1, 2, 3, 6 and 51 above.

For each of Examples 53-57, identification of the title compound by $^1$H-NMR showed that the oxime product was a single isomer, but did not confirm whether the (E) or (Z) oxime isomer had been obtained.

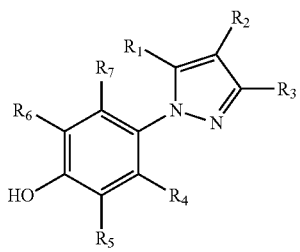

E 53  5-(3,5-dimethylpyridin-4-yl)-1-(2-fluoro-4-hydroxyphenyl)-N'-hydroxy-3-methyl-1H-pyrazole-4-carboximidamide
$R_1$ = 3,5-dimethylpyridin-4-yl    $R_2$ = N-Hydroxy carbamimidoyl    $R_3$ = methyl
$R_4$ = F    $R_5$ = H    $R_6$ = H    $R_7$ = H
ES/MS m/z: 356.1 (pos. M + H), 354.21 (neg. M − H); $^1$H NMR (MeOD, 500 MHz): 8.17 (s, 2H), 7.12 (t, 1H, J = 8.8 Hz), 6.56 (m, 1H), 6.49 (dd, 1H, J = 12.2, 2.6 Hz), 2.44 (s, 3H) and 2.10 (s, 6H).

E 54  5-(3,5-dimethylisoxazol-4-yl)-N'-hydroxy-1-(4-hydroxy-2-methylphenyl)-3-methyl-1H-pyrazole-4-carboximidamide
$R_1$ = 3,5-dimethylisoxazol-4-yl    $R_2$ = N-Hydroxy carbamimidoyl    $R_3$ = methyl
$R_4$ = methyl    $R_5$ = H    $R_6$ = H    $R_7$ = H
ES/MS m/z: 342.1 (pos. M + H), 340.19 (neg. M − H); $^1$H NMR (acetone-d6, 500 MHz): 6.89 (d, 1H, J = 8.6 Hz), 6.75 (d, 1H, J = 2.6 Hz), 6.65 (dd, 1H, J = 8.6, 2.6 Hz), 2.09 (s, 3H), 2.01 (s, 3H) and 1.95 (s, 3H).

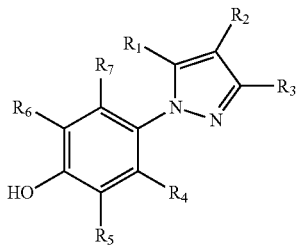

E 55  5-(3,5-dimethylisoxazol-4-yl)-3-ethyl-N'-hydroxy-1-(4-hydroxy-2-methylphenyl)-1H-pyrazole-4-carboximidamide
$R_1$ = 3,5-dimethylisoxazol-4-yl    $R_2$ = N-Hydroxy carbamimidoyl    $R_3$ = ethyl
$R_4$ = methyl    $R_5$ = H    $R_6$ = H    $R_7$ = H
ES/MS m/z: 356.09 (pos. M + H), 354.2 (neg. M − H); $^1$H NMR (acetone-d6, 500 MHz): 6.88 (d, 1H, J = 8.9 Hz), 6.76 (d, 1H, J = 2.7 Hz), 6.64 (dd, 1H, J = 8.9, 2.7 Hz), 2.82 (q, 2H, J = 7.5 Hz), 2.09 (s, 3H), 2.03 (s, 3H), 1.95 (s, 3H) and 1.26 (t, 3H, J = 7.5 Hz).

E 56  5-(3,5-dimethyl-1H-pyrrol-1-yl)-N'-hydroxy-1-(4-hydroxy-2-methylphenyl)-3-methyl-1H-pyrazole-4-carboximidamide
$R_1$ = 2,5-dimethyl-1H-pyrrol-1-yl    $R_2$ = N-Hydroxy carbamimidoyl    $R_3$ = methyl
$R_4$ = methyl    $R_5$ = H    $R_6$ = H    $R_7$ = H
ES/MS m/z: 340.07 (pos. M + H), 338.24 (neg. M − H); $^1$H NMR (acetone-d6, 500 MHz): 6.78 (d, 1H, J = 2.6 Hz), 6.71 (d, 1H, J = 8.7 Hz), 6.56 (dd, 1H; J = 8.7, 2.6 Hz), 5.76 (s, 2H), 2.41 (s, 3H), 2.17 (s, 3H) and 1.96 (s, 6H).

E 57  N'-hydroxy-1-(4-hydroxy-2-methylphenyl)-3-methyl-5-(2-methyl-5-propyl-1H-pyrrol-1-yl)-1H-pyrazole-4-carboximidamide
$R_1$ = 2-methyl-5-propyl-1H-pyrrol-1-yl    $R_2$ = N-Hydroxy carbamimidoyl    $R_3$ = methyl
$R_4$ = methyl    $R_5$ = H    $R_6$ = H    $R_7$ = H
ES/MS m/z: 368.12 (pos. M + H), 366.27 (neg. M − H); $^1$H NMR (acetone-d6, 500 MHz): 6.78 (d, 1H, J = 2.6 Hz), 6.69 (d, 1H, J = 8.3 Hz), 6.54 (dd, 1H; J = 8.3, 2.6 Hz), 5.83 (d, 1H, J = 3.0 Hz), 5.79 (d, 1H, J = 3.0 Hz), 2.41 (s, 3H), 2.27-2.09 (m, 5H), 1.99 (s, 3H), 1.56-1.38 (m, 2H) and 0.86 (t, 3H, J = 7.4 Hz).

EXAMPLE 58

4-(2,4-dimethylthiophen-3-yl)-3-(2-fluoro-4-hydroxyphenyl)-N'-hydroxy-1-methyl-1H-pyrazole-5-carboximidamide (E58)

Scheme 11

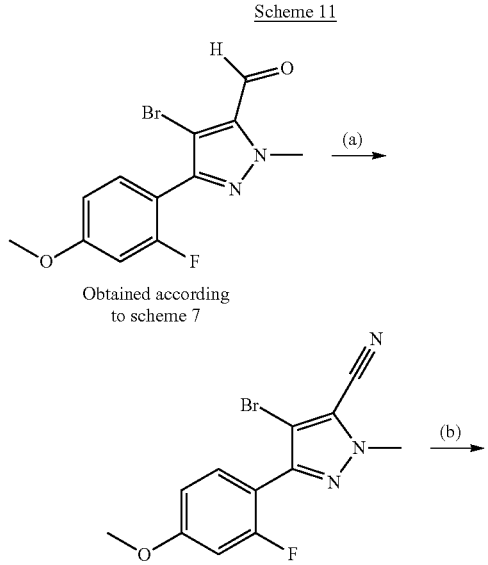

Obtained according to scheme 7

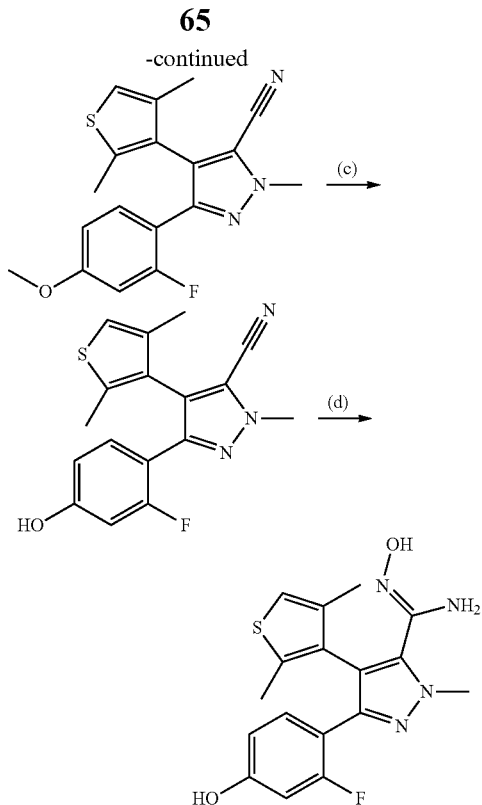

(a) NH₂OH·HCl, pyridine (EtOH); (b) Pd₂(dba)₃, tributyl(2,4-dimethylthiophen-3-yl)stannane, trio-tolylphosphine (DMF); (c) BF₃·SMe₂ (CH₂Cl₂); (d) NH₂OH (DMSO/H₂O)

Step (a): A mixture of 4-bromo-3-(2-fluoro-4-methoxyphenyl)-1-methyl-1H-pyrazole-5-carbaldehyde (64.9 mg, 0.21 mmol), hydroxylamine hydrochloride (144 mg, 2.07 mmol) and pyridine (184 μL, 2.28 mmol) in ethanol (2 mL) was heated at 110° C. for 3 minutes in the microwave. DCM was added and a precipitate was formed, which was the desired product. The remaining solution was extracted with DCM. The DCM layer was filtered through a phase separator and concentrated together with the precipitate to give the raw product. To this was added acetic anhydride (1 mL) and the mixture was heated at 150° C. for 50 minutes in a microwave. DCM was added and the mixture was washed with HCl (2M), NaHCO₃ (sat) and then filtered through a phase separator. The solvent was concentrated to give 4-bromo-3-(2-fluoro-4-methoxyphenyl)-1-methyl-1H-pyrazole-5-carbonitrile (58.0 mg, 89%)

Step (c): 4-bromo-3-(2-fluoro-4-methoxyphenyl)-1-methyl-1H-pyrazole-5-carbonitrile (49 mg, 0.16 mmol), tributyl (2,4-dimethylthiophen-3-yl)stannane (82.24 mg, 0.20 mmol), Pd₂(dba)₃ (14.44 mg, 0.02 mmol) and trio-tolylphosphine (9.6 mg, 0.03 mmol) were mixed with 1.5 mL DMF and the mixture was degassed under nitrogen in a vial. The vial was sealed and the reaction was heated at 85° C. over night. Water was added, the mixture was extracted with CH₂Cl₂ and the organic layer was concentrated. The crude product was purified on silica to give 4-(2,4-dimethylthiophen-3-yl)-3-(2-fluoro-4-methoxyphenyl)-1-methyl-1H-pyrazole-5-carbonitrile (17 mg, 32%).

Step (c): 4-(2,4-dimethylthiophen-3-yl)-3-(2-fluoro-4-methoxyphenyl)-1-methyl-1H-pyrazole-5-carbonitrile (17 mg, 0.05 mmol) was dissolved in dry DCM (2 mL) and BF₃·Me₂S (1 M solution in DCM, 0.3 mL, 0.3 mmol) was added and the mixture was stirred at room temperature over night. The mixture was concentrated and MeOH was added to quench the reaction The crude product was purified on silica gel to give -(2,4-dimethylthiophen-3-yl)-3-(2-fluoro-4-hydroxyphenyl)-1-methyl-1H-pyrazole-5-carbonitrile (7.0 mg, 43%).

Step (d): To a solution of 4-(2,4-dimethylthiophen-3-yl)-3-(2-fluoro-4-hydroxyphenyl)-1-methyl-1H-pyrazole-5-carbonitrile (7 mg, 0.02 mmol) in DMSO (0.6 mL) was added neutral hydroxylamine solution (16 M in water, 0.33 mL, 5.35 mmol) The reaction was heated at 150° C. in the microwave for 15 min. EtOAc and water were added and the phases were separated. The crude product was purified on preparative HPLC to give 4-(2,4-dimethylthiophen-3-yl)-3-(2-fluoro-4-hydroxyphenyl)-N-hydroxy-1-methyl-1H-pyrazole-5-carboximidamide (3.62 mg, 47%). Identification of the title compound by ¹H-NMR showed that the oxime product was a single isomer, but did not confirm whether the (E) or (Z) oxime isomer had been obtained. ES/MS m/z: 361.06 (M+H), 359.14 (M−H); ¹H NMR (acetone-d6, 500 MHz): 7.05 (t, 1H, J=8.6 Hz), 6.77 (q, 1H, J=0.9 Hz), 6.59 (dd, 1H, J=8.6, 2.5 Hz), 6.51 (dd, 1H, J=11.7, 2.5 Hz), 4.01 (s, 3H), 2.07 (s, 3H) and 1.88 (d, 3H, J=0.9 Hz).

EXAMPLES 59-68

The following compounds were prepared according to General Methods VI and IX above. Full experimental details of the individual steps of that general method are described in Examples 12, 13, 14, 16 and 58 above.

For each of Examples 59, 61, 62, 63, 64, 66, 67 and 68 identification of the title compound by ¹H-NMR showed that the oxime product was a single isomer, but did not confirm whether the (E) or (Z) oxime isomer had been obtained.

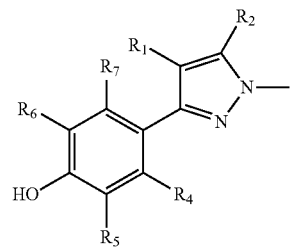

E 59  4-(3,5-dimethylisoxazol-4-yl)-3-(3-fluoro-4-hydroxyphenyl)-1-methyl-1H-pyrazole-5-carbaldehyde oxime
$R_1$ = 3,5-dimethylisoxazol-4-yl        $R_2$ = hydroxyimino methyl
$R_4$ = H        $R_5$ = F        $R_6$ = H        $R_7$ = H
ES/MS m/z: 331.05 (pos. M + H), 329.14 (neg. M − H); ¹H NMR (acetone-d6, 500 MHz): 7.94 (s, 1H), 7.24 (dd, 1H, J = 12.6, 2.2 Hz), 7.08 (m, 1H), 6.94 (t, 1H, J = 9.0 Hz), 4.09 (s, 3H), 2.17 (s, 3H) and 1.89 (s, 3H).

E 60  4-(3,5-dimethylisoxazol-4-yl)-3-(3-fluoro-4-hydroxyphenyl)-1-methyl-1H-pyrazole-5-carboxamide
$R_1$ = 3,5-dimethylisoxazol-4-yl        $R_2$ = carboxamide
$R_4$ = H        $R_5$ = F        $R_6$ = H        $R_7$ = H
ES/MS m/z: 331.05 (pos. M + H), 329.16 (neg. M − H); ¹H NMR (acetone-d6, 500 MHz): 7.18 (dd, 1H, J = 12.4, 1.9 Hz), 7.03 (dd, 1H, J = 8.4, 1.9 Hz), 6.95 (t, 1H, J = 8.4 Hz), 4.12 (s, 3H), 2.14 (s, 3H) and 1.94 (s, 3H).

E 61  4-(3,5-dimethylisoxazol-4-yl)-3-(3-fluoro-4-hydroxyphenyl)-N'-hydroxy-1-methyl-1H-pyrazole-5-carboximidamide
$R_1$ = 3,5-dimethylisoxazol-4-yl        $R_2$ = N-Hydroxy carbamimidoyl
$R_4$ = H        $R_5$ = F        $R_6$ = H        $R_7$ = H
ES/MS m/z: 346.02 (pos. M + H), 344.19 (neg. M − H); ¹H NMR (acetone-d6, 500 MHz): 7.21 (dd, 1H, J = 12.6, 2.0 Hz), 7.06 (dd, 1H, J = 8.8, 2.0 Hz), 6.93 (t, 1H, J = 8.8 Hz), 3.96 (s, 3H), 2.13 (s, 3H) and 1.90 (s, 3H).

-continued

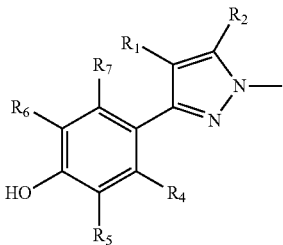

E 62 (Z)-4-(3,5-dimethylisoxazol-4-yl)-3-(4-hydroxy-2-methylphenyl)-1-methyl-1H-pyrazole-5-carbaldehyde oxime
R₁ = 3,5-dimethylisoxazol-4-yl    R² = hydroxyimino methyl
R₄ = methyl    R₅ = H    R₆ = H    R₇ = H
ES/MS m/z: 327.08 (pos. M + H), 325.14 (neg. M − H); ¹H NMR (acetone-d6, 500 MHz): 7.46 (s, 1H), 6.92 (d, 1H, J = 8.3 Hz), 6.71 (d, 1H, J = 2.2 Hz), 6.60 (dd, 1H, J = 8.3, 2.2 Hz), 3.93 (s, 3H), 2.13 (s, 3H), 2.05 (s, 3H) and 1.76 (s, 3H).

E 63 (E)-4-(3,5-dimethylisoxazol-4-yl)-3-(4-hydroxy-2-methylphenyl)-1-methyl-1H-pyrazole-5-carbaldehyde oxime
R₁ = 3,5-dimethylisoxazol-4-yl    R² = hydroxyimino methyl
R₄ = methyl    R₅ = H    R₆ = H    R₇ = H
ES/MS m/z: 327.06 (pos. M + H), 325.1 (neg. M − H); ¹H NMR (acetone-d6, 500 MHz): 7.99 (s, 1H), 6.89 (d, 1H, J = 8.3 Hz), 6.70 (d, 1H, J = 2.5 Hz), 6.60 (dd, 1H, J = 8.3, 2.5 Hz), 4.09 (s, 3H), 2.13 (s, 3H), 2.07 (s, 3H) and 1.81 (s, 3H).

E 64 4-(3,5-dimethylisoxazol-4-yl)-N'-hydroxy-3-(4-hydroxy-2-methylphenyl)-1-methyl-1H-pyrazole-5-carboximidamide
R₁ = 3,5-dimethylisoxazol-4-yl    R² = N-Hydroxy carbamimidoyl
R₄ = methyl    R₅ = H    R₆ = H    R₇ = H
ES/MS m/z: 342.1 (pos. M + H), 340.21 (neg. M − H); ¹H NMR (acetone-d6, 500 MHz): 7.99 (s, 1H), 6.89 (d, 1H, J = 8.3 Hz), 6.70 (d, 1H, J = 2.5 Hz), 6.60 (dd, 1H, J = 8.3, 2.5 Hz), 4.09 (s, 3H), 2.13 (s, 3H), 2.07 (s, 3H) and 1.81 (s, 3H).

E 65 4-(3,5-dimethylisoxazol-4-yl)-N'-hydroxy-3-(4-hydroxy-2-methylphenyl)-1-methyl-1H-pyrazole-5-carboximidamide
R₁ = 3,5-dimethylisoxazol-4-yl    R² = carboxamide
R₄ = methyl    R₅ = H    R₆ = H    R₇ = H
ES/MS m/z: 327.06 (pos. M + H), 325.19 (neg. M − H); ¹H NMR (acetone-d6, 500 MHz): 6.86 (d, 1H, J = 8.4 Hz), 6.71 (d, 1H, J = 2.4 Hz), 6.61 (dd, 1H, J = 8.4, 2.4 Hz), 4.12 (s, 3H), 2.09 (s, 3H), 2.01 (s, 3H) and 1.89 (s, 3H).

E 66 4-(2,5-dimethylthiophen-3-yl)-N'-hydroxy-3-(4-hydroxy-2-methylphenyl)-1-methyl-1H-pyrazole-5-carboximidamide
R₁ = 2,4-dimethylthiophen-3-yl    R² = N-Hydroxy carbamimidoyl
R₄ = methyl    R₅ = H    R₆ = H    R₇ = H
ES/MS m/z: 357.07 (pos. M + H); ¹H NMR (acetone-d6, 500 MHz): 6.78 (d, 1H, J = 8.4 Hz), 6.76 (s, 1H), 6.65 (d, 1H, J = 2.5 Hz), 6.50 (dd, 1H, J = 8.4, 2.5 Hz), 4.01 (s, 3H), 2.15 (s, 3H), 2.06 (s, 3H) and 1.85 (s, 3H).

E 67 4-(3,5-dimethylisoxazol-4-yl)-3-(2-fluoro-4-hydroxyphenyl)-N'-hydroxy-1-methyl-1H-pyrazole-5-carboximidamide
R₁ = 3,5-dimethylisoxazol-4-yl    R² = N-Hydroxy carbamimidoyl
R₄ = F    R₅ = H    R₆ = H    R₇ = H
ES/MS m/z: 362.11 (pos. M + H), 360.19 (neg. M − H); ¹H NMR (acetone-d6, 500 MHz): 7.15 (t, 1H, J = 8.6 Hz), 6.65 (dd, 1H, J = 8.6, 2.5 Hz), 6.50 (dd, 11.9, 2.5 Hz), 4.01 (s, 3H), 2.15 (s, 3H) and 2.08 (s, 3H).

E 68 4-(2,6-dimethylphenyl)-3-(2-fluoro-4-hydroxyphenyl)-N'-hydroxy-1-methyl-1H-pyrazole-5-carboximidamide
R₁ = 2,6-dimethylphenyl    R² = N-Hydroxy carbamimidoyl
R₄ = F    R₅ = H    R₆ = H    R₇ = H
ES/MS m/z: 355.11 (pos. M + H), 353.22 (neg. M − H); ¹H NMR (acetone-d6, 500 MHz): 7.09-6.99 (m, 4H), 6.54 (dd, 1H, J = 8.5, 2.4 Hz), 6.48 (dd, 1H, J = 11.8, 2.4 Hz), 4.03 (s, 3H) and 2.02 (s, 6H).

EXAMPLE 69

4-(2,4-dimethylfuran-3-yl)-3-(4-hydroxyphenyl)-1-methyl-1H-pyrazole-5-carbaldehyde oxime (E69)

Scheme 12

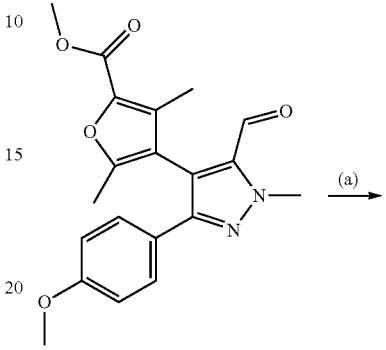

(a)

Obtained according to scheme 7

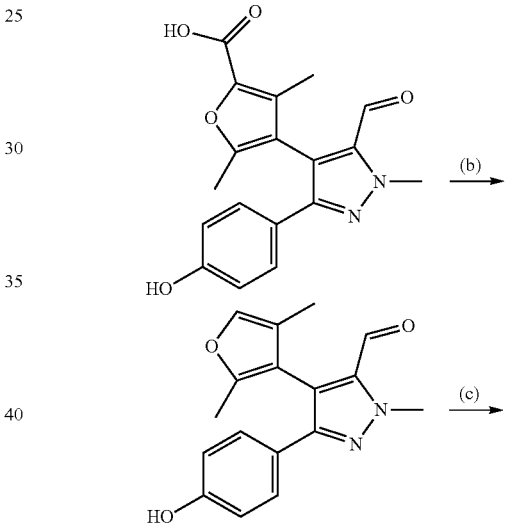

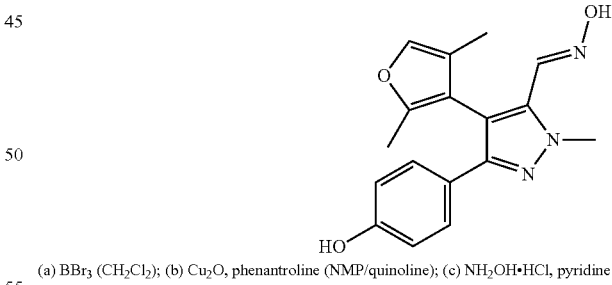

(a) BBr₃ (CH₂Cl₂); (b) Cu₂O, phenantroline (NMP/quinoline); (c) NH₂OH•HCl, pyridine (EtOH)

Step (a): methyl 4-(5-formyl-3-(4-methoxyphenyl)-1-methyl-1H-pyrazol-4-yl)-3,5-dimethylfuran-2-carboxylate (55 mg, 0.15 mmol) was dissolved in CH₂Cl₂ (7.5 mL) and BBr₃ (1 M solution on DCM, 0.75 mL, 0.75 mmol) was added and stirred at room temperature over night. The reaction was quenched using water and extracted with CH₂Cl₂. Concentration and filtration trough a short plug of silica gave 4-(5-formyl-3-(4-hydroxyphenyl)-1-methyl-1H-pyrazol-4-yl)-3,5-dimethylfuran-2-carboxylic acid (45 mg, 75%) which was used as such in the next step.

Step (b): A mixture of 4-(5-formyl-3-(4-hydroxyphenyl)-1-methyl-1H-pyrazol-4-yl)-3,5-dimethylfuran-2-carboxylic acid (45 mg, 0.13 mmol), phenantroline (9.53 mg, 0.05 mmol) and $Cu_2O$ (3.78 mg, 0.026 mmol) in quinoline (0.73 ml) and NMP (2.19 mL) was flushed with $N_2$ and irradiated in the microwave at 190° C. for 15 min. HCl (1M) and $CH_2Cl_2$ were added and the phases were separated. The crude product was purified on preparative HPLC to give 4-(2,4-dimethylfuran-3-yl)-3-(4-hydroxyphenyl)-1-methyl-1H-pyrazole-5-carbaldehyde (20.0 mg, 51%).

Step (f): A mixture of 4-(3,5-dimethylisoxazol-4-yl)-3-(4-methoxyphenyl)-1-methyl-1H-pyrazole-5-carbaldehyde (20 mg, 0.07 mmol), hydroxylamine hydrochloride (93.8 mg, 1.35 mmol) and pyridine (164 μL, 2.02 mmol) in dry EtOH (1.6 mL) was heated at 120° C. for 15 minutes in the microwave. Water and DCM were added and the phases were separated. The crude product was purified on preparative HPLC to give 4-(2,4-dimethylfuran-3-yl)-3-(4-hydroxyphenyl)-1-methyl-1H-pyrazole-5-carbaldehyde oxime (6.2 mg, 30%). Identification of the title compound by $^1$H-NMR showed that the oxime product was a single isomer, but did not confirm whether the (E) or (Z) oxime isomer had been obtained. ES/MS m/z: 312.1 (M+H), 310.26 (M−H); $^1$H NMR (acetone-d6, 500 MHz): 7.77 (s, 1H), 7.40 (m, 2H), 7.32 (q, 1H, J=1.0 Hz), 6.76 (m, 2H), 4.09 (s, 3H), 2.02 (s, 3H) and 1.63 (q, 3H, J=1.0 Hz).

EXAMPLE 70 AND 71

The following compounds were prepared according to General Methods VII above. Full experimental details of the individual steps of that general method are described in Examples 12, 13, 14 and 16 above. For each of Examples 70 and 71, identification of the title compound by $^1$H-NMR showed that the oxime product was a single isomer, but did not confirm whether the (E) or (Z) oxime isomer had been obtained

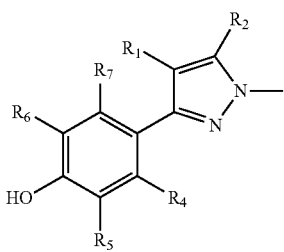

E 70  4-(3,5-dimethylisothiazol-4-yl)-3-(4-hydroxyphenyl)-1-methyl-1H-pyrazole-5-carbaldehyde oxime
$R_1$ = 3,5-dimethylisothiazol-4-yl    $R^2$ = hydroxyimino methyl
$R_4$ = H        $R_5$ = H        $R_6$ = H        $R_7$ = H
ES/MS m/z: 329.1 (pos. M + H), 327.26 (neg. M − H); $^1$H NMR (acetone-d6, 500 MHz): 7.80 (s, 1H), 7.20 (m, 2H), 6.73 (m, 2H), 4.11 (s, 3H), 2.23 (s, 3H) and 2.04 (s, 3H).

E 71  4-(3,5-dimethylisothiazol-4-yl)-N'-hydroxy-3-(4-hydroxyphenyl)-1-methyl-1H-pyrazole-5-carboximidamide
$R_1$ = 3,5-dimethylisothiazol-4-yl    $R^2$ = N-Hydroxy carbamimidoyl
$R_4$ = H        $R_5$ = H        $R_6$ = H        $R_7$ = H
ES/MS m/z: 344.13 (pos. M + H); $^1$H NMR (acetone-d6, 500 MHz): 7.17 (m, 2H), 6.72 (m, 2H), 3.98 (s, 3H), 2.22 (s, 3H) and 2.07 (s, 3H).

Binding Assay 1: Estrogen Receptor Binding Assay

The estrogen receptor ligand binding assays are designed as scintillation proximity assays (SPA), employing the use of tritiated estradiol ($^3$H-E2) and recombinant expressed biotinylated estrogen receptor binding domains. The binding domains of human ERα (ERα-LBD, pET-N-AT #1, aa 301-595) and ERβ (ERβ-LBD, pET-N-AT #1, aa 255-530) proteins are produced in *E. coli* ((BL21, (DE3), pBirA)) at 22 C in 2×LB medium supplemented with 50 uM biotin. After 3 h of IPTG induction (0.55 mM), cells are harvested by centrifugation at 7300×g for 15 min and cell pellets stored frozen in −20C. Extraction of ERα and ERβ are performed using 5 g of cells suspended in 50 mL of extraction buffer (50 mM Tris, pH 8.0, 100 mM KCl, 4 mM EDTA, 4 mM DDT and 0.1 mM PMSF). The cell suspension is run twice through a Microfluidizer M-110L (Microfluidics) and centrifuged at 15,000×g for 60 min. The supernatant is aliquoted and stored in −70C.

Dilute ERαLBD or ERβ-LBD extracts in assay buffer (18 mM $K_2HPO_4$, 2 mM $KH_2PO_4$, 20 mM $Na_sMoO_4$, 1 mM EDTA, 1 mM TCEP) 1:676 and 1:517 for alpha and beta respectively. The diluted receptor concentrations should be 900 fmol/L. Preincubate the extracts with streptavidin coated polyvinyltoluene SPA beads (RPNQ0007, GE Healthcare) at a concentration of 0.43 mg/mL for 1 hr at room temperature.

Test compounds are evaluated over a range of concentrations from 157 μM to 37.5 pM. The test compound stock solutions should be made in 100% DMSO at 5× of the final concentration desired for testing in the assay. The amount of DMSO in the test wells of the 384 well plate will be 20%. Add 18 μl aliquots of test compounds to the assay plates followed by 35 μl of the preincubated receptor/SPA bead mix and finally add 35 μl of 3 nM $^3$H-E2. Cover the plates with a plastic sealer, centrifuge for 1 minute at 1000 rpm and equilibrate over night on a shaker at room temperature. The following morning, centrifuge the plates 5 minutes at 2000 rpm and measure on a plate scintillation counter e.g. a PerkinElmer Microbeta 1450 Trilux.

For compounds able to displace 3[H]-E2 from the receptor an $IC_{50}$-value (the concentration required to inhibit 50% of the binding of 3[H]-E2) is determined by a non-linear four parameter logistic model; b=((bmax−bmin)/(1+(1/$IC_{50}$)S))+bmin I is added concentration of binding inhibitor, $IC_{50}$ is the concentration of inhibitor at half maximal binding and S is a slope factor. The Microbeta-instrument generates the mean cpm (counts per minute) value/minute and corrects for individual variations between the detectors thus generating corrected cpm values.

Transactivation Assay 1: Transactivation Assay in Human Embryonic Kidney 293 Cells Stably Transfected with pERE-ALP and Human Estrogen Receptor Alpha The expression vector pMThERα contains an insert of wild type human estrogen receptor alpha with deleted leader. The pERE-ALP reporter construct contains the gene for the secreted form of placental alkaline phosphatase (ALP) and the vitellogenin estrogen response element (ERE). The human embryonic kidney 293 cells are transfected in two steps. Firstly, a stable clone mix transfected with the pERE-ALP reporter gene construct and pSV2-Neo for selection is developed. Secondly, the stable clone mix is transfected with pMThERα and a pKSV-Hyg resistance vector for selection. All transfections are performed using Lipofectamine (Invitrogen) according to supplier's recommendations. A selected clone with both pERE-ALP and pMThERα, is used for the transactivation assay.

The cells are seeded in 384-well plates at 12 500 cells per well in Ham's F12 Coon's modification (without phenol red) with 10% dextran-coated charcoal treated (DCC) fetal bovine serum (FBS), 2 mM L-glutamine and 50 μg/ml gentamicin. After 24 h incubation (37° C., 5% $CO_2$) the seeding medium is discarded and replaced with 20 μl Ham's F12 Coon's modification (without phenol red) with 1.5% DCC-FCS, 2 mM L-glutamine and supplemented with 100 U/ml penicillin and 100 μg/ml streptomycin. The selected compounds are added to the wells in 12 concentrations ranging from 3.3 pM to 33 μM. The compounds are dissolved in 100% dimethylsulphoxide (DMSO) and the final concentration of DMSO in the assay is 0.1%. After 72 h incubation (37° C., 5% $CO_2$) the medium is assayed for ALP activity by a chemiluminescence assay; a 10 μl aliquot of the cell culture medium is mixed with 100 μl assay buffer (0.1 M diethanolamine, 1 mM $MgCl_2$) and 0.5 mM disodium 3-(4-methoxyspiro 1,2-dioxetane-3,2'-(5'-chloro)-tricyclo[3.3.1.13,7]decan-4-yl)phenyl phosphate (CSPD) (Tropix, Applied Biosystems) and incubated for 20 min at 37° C. and 15 min at room temperature before measurement chemiluminescent light signal (one second per well) in a Wallac Microbeta Trilux 1450-028 (PerkinElmer). The half maximal effective concentrations ($EC_{50}$) are calculated from the curves fitted to the concentration-response data with a four parameter logistic model in XLfit software version 2.0 (IDBS) or later.

Transactivation Assay 2: Transactivation Assay in Human Embryonic Kidney 293 Cells Stably Transfected with pERE2-ALP and Human Estrogen Receptor Beta Generation of stable HEK293 cell lines (CRL-1573; American Type Culture Collection) expressing the reporter vector pERE2-ALP and human estrogen receptor beta (hERβ530) have been described (Mol Pharmacol 1998, 54, 105-112; Endocrinology 2002, 143, 1558-1561).

The cells were seeded in 384-well plates at 12 500 cells per well in Ham's F12 Coon's modification (without phenol red) with 10% dextran-coated charcoal treated (DCC) fetal bovine serum (FBS), 2 mM L-glutamine and 50 μg/ml gentamicin. After 24 h incubation (37° C., 5% CO2) the seeding medium was discarded and replaced with 20 μl Ham's F12 Coon's modification (without phenol red) with 1.5% DCC-FCS, 2 mM L-glutamine and supplemented with 100 U/ml penicillin and 100 μg/ml streptomycin. The selected compounds were added to the wells in 12 concentrations ranging from 3.3 pM to 33 μM. The compounds were dissolved in 100% dimethylsulfoxide (DMSO) and the final concentration of DMSO in the assay was 0.1%. After 72 h incubation (37° C., 5% CO2) the medium was assayed for ALP activity by a chemiluminescence assay; a 10 μl aliquot of the conditioned medium was mixed with 100 μl assay buffer (0.1 M diethanolamine, 1 mM MgCl2) and 0.5 mM disodium 3-(4-methoxyspiro 1,2-dioxetane-3,2'-(5'-chloro)-tricyclo[3.3.1.13,7]decan-4-yl) phenyl phosphate (CSPD) (Tropix, Applied Biosystems) and incubated for 20 min at 37° C. and 15 min at room temperature before measurement of the chemiluminescent signal (one second per well) in a Wallac Microbeta Trilux 1450-028 (PerkinElmer). The ALP activity expressed in LCPS is directly proportional to the level of ALP expressed by the cells. The half maximal effective concentrations of the test compounds (EC50) were calculated from the curves fitted to the concentration-response data with a four parameter logistic model in XLfit software version 2.0 (IDBS) or later.

The Example compounds were tested in binding assay 1 and in transactivation assays 1 and 2.

The compounds of Examples 1-71 exhibit one or more of the following:
(i) a binding affinity to the estrogen receptor α-subtype in the range of $IC_{50}$ 1 to 10,000 nM in binding assay 1;
(ii) a binding affinity to the estrogen receptor β-subtype in the range of $IC_{50}$ 1 to 10,000 nM in binding assay 1;
(iii) a potency in the range of $EC_{50}$ 1 to 10,000 nM at the estrogen receptor α-subtype in transactivation assay 1;
(iv) a potency in the range of $EC_{50}$ 1 to 10,000 nM at the estrogen receptor β-subtype in transactivation assay 2.

Preferred Example compounds of the invention are those which exhibit a binding affinity to the estrogen receptor β-subtype at lower concentrations within the $IC_{50}$ range shown above. For example, the compounds of Examples 12, 18, 19, 27, 44, 45, 48 and 63 exhibit a binding affinity to the estrogen receptor β-subtype in the range of $IC_{50}$ 1 to 100 nM in binding assay 1.

Preferred Example compounds of the invention are those which are selective for the estrogen receptor β-subtype over the estrogen receptor α-subtype in binding assay 1. For example, the compounds of Examples 3, 4, 6, 8, 12, 18, 19, 26, 27, 33, 38, 39, 44, 45, 56, 58, 59, 63, 66 and 68 display selectivity for the estrogen receptor β-subtype of 10 or greater in the binding assay.

Preferred Example compounds of the invention are those which display a potency at the estrogen receptor β-subtype at lower concentrations within the $EC_{50}$ range shown above. For example, the compounds of Examples 3-6, 8, 9, 12, 13, 18, 19, 20, 24-27, 30-35, 37-41, 44, 45, 47, 48, 50, 51, 52, 54-57, 62-64, 66-68, 70 and 71 exhibit a potency in the range of $EC_{50}$ 0.1 to 100 nM at the estrogen receptor β-subtype in transactivation assay 2.

Preferred Example compounds of the invention are those which are selective for the estrogen receptor β-subtype over the estrogen receptor α-subtype in the transactivation assays 1 and 2. For example, the compounds of Examples 3, 5, 8, 13, 19-22, 24, 31, 32, 36, 48, 50, 51, 54, 64, 67, 70 and 71 display selectivity for the estrogen receptor β-subtype of 50 or greater in the transactivation assays.

The invention claimed is:

1. A compound of formula (I) or a pharmaceutically acceptable ester, amide, solvate or salt thereof, or a salt of such an ester or amide, or a solvate of such an ester, amide or salt,

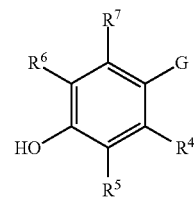

(I)

wherein G represents one of the groups:

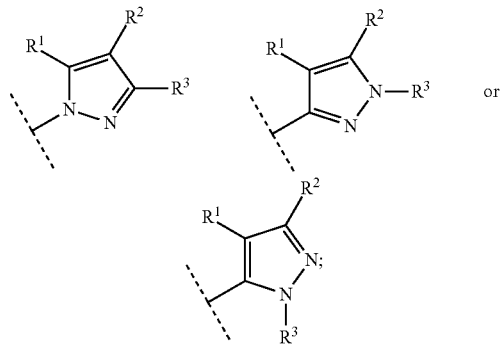

$R^1$ is selected from the group consisting of halogen, cyano, nitro, $OR^A$, $N(R^B)_2$, $—C(O)C_{1-4}$alkyl, $—SO_2C_{1-4}$alkyl, $C_{1-6}$alkyl, $C_{2-6}$alkenyl, $C_{2-6}$alkynyl, halo$C_{1-6}$alkyl, dihalo$C_{1-6}$alkyl, trihalo$C_{1-6}$alkyl, halo$C_{2-6}$alkenyl, dihaloC$_{2-6}$alkenyl, trihaloC$_{2-6}$alkenyl, cyanoC$_{1-6}$alkyl, C$_{1-4}$alkoxyC$_{1-6}$ alkyl, C$_{3-8}$cycloalkyl, C$_{3-8}$cycloalkylC$_{1-6}$alkyl, phenyl, benzyl, and 5-10 membered heterocyclyl, wherein said benzyl or heterocyclyl is either unsubstituted or said phenyl, benzyl or heterocyclyl is substituted with from 1 to 3 substituents, each substituent being independently selected from the group consisting of OR$^A$, N(R$^B$)$_2$, halogen, cyano, nitro, —C(O)C$_{1-4}$alkyl, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl;

R$^2$ is selected from the group consisting of —CH=N—OH, and —C(NH$_2$)=N—OH;

R$^3$ is selected from the group consisting of hydrogen, halogen, C$_{1-6}$alkyl, C$_{2-6}$alkenyl, C$_{2-6}$alkynyl, C$_{3-8}$cycloalkyl, C$_{3-8}$cycloalkylC$_{1-6}$alkyl; haloC$_{1-6}$alkyl, dihaloC$_{1-6}$alkyl, trihaloC$_{1-6}$alkyl, phenyl, benzyl and 5-10 membered heterocyclyl wherein said benzyl or heterocyclyl is either unsubstituted or said phenyl, benzyl or heterocyclyl is substituted with from 1 to 3 substituents, each substituent being independently selected from the group consisting of OR$^A$, halogen, cyano, nitro, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl;

and wherein only one of R$^1$ and R$^3$ may be a substituted or unsubstituted phenyl;

each of R$^4$, R$^5$, R$^6$ and R$^7$ is independently selected from the group consisting of hydrogen, OR$^A$, halogen, cyano, nitro, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl;

each R$^A$ is independently selected from the group consisting of hydrogen, C$_{1-6}$alkyl, C$_{2-6}$alkenyl, C$_{2-6}$alkynyl, C$_{3-8}$cycloalkyl, C$_{3-8}$cycloalkylC$_{1-6}$alkyl, phenyl, benzyl and 5-10 membered heterocyclyl, each optionally substituted by from 1 to 3 halogen atoms; and each R$^B$ is independently selected from the group consisting of hydrogen, C$_{1-6}$alkyl, C$_{2-6}$alkenyl, C$_{2-6}$alkynyl, C$_{3-8}$cycloalkyl, C$_{3-8}$cycloalkylC$_{1-6}$alkyl, phenyl, benzyl and 5-10 membered heterocyclyl, each optionally substituted by from 1 to 3 halogen atoms.

2. A compound as claimed in claim 1 wherein G is a group selected from:

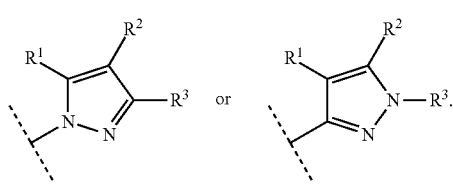

3. A compound as claimed in claim 1, in which R$^1$ represents N(R$^B$)$_2$, phenyl or a 5-10 membered heterocyclyl, wherein said heterocyclyl is either unsubstituted or said phenyl or heterocyclyl is substituted with from 1 to 3 substituents, each substituent being independently selected from the group consisting of halogen, and C$_{1-6}$alkyl; and R$^B$ represents C$_{1-6}$alkyl.

4. A compound as claimed in claim 1, in which R$^1$ is selected from C$_{2-6}$alkenyl, N(R$^B$)$_2$, phenyl or 5-10 membered heterocyclyl, wherein said phenyl or heterocyclyl is either unsubstituted or said phenyl or heterocyclyl is substituted with from 1 to 3 substituents, each substituent being independently selected from the group consisting of halogen, cyano, nitro, C$_{1-6}$alkyl, and trihaloC$_{1-6}$alkyl, and each R$^B$ representing C$_{1-6}$alkyl.

5. A compound as claimed in claim 1, in which R$^3$ represents hydrogen, halogen, C$_{1-6}$alkyl, C$_{2-6}$alkenyl, phenyl, or 5-10 membered heterocyclyl wherein said heterocyclyl is either unsubstituted or said phenyl or heterocyclyl is substituted with from 1 to 3 substituents, each substituent being independently selected from the group consisting of halogen, cyano, C$_{1-6}$alkyl and trihaloC$_{1-6}$alkyl.

6. A compound as claimed in claim 1, in which R$^3$ is selected from the group consisting of hydrogen, halogen, C$_{1-6}$alkyl, C$_{2-6}$alkenyl and C$_{2-6}$alkynyl and C$_{3-8}$cycloalkyl.

7. A compound as claimed in claim 1, in which each of R$^4$, R$^5$, R$^6$ and R$^7$ is independently selected from the group consisting of hydrogen, halogen and methyl.

8. A compound as claimed in claim 1, in which G represents

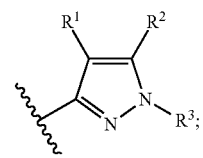

R$^1$ represents a 5-membered heterocycle substituted with 2 C$_{1-3}$alkyl; R$^2$ represents —C(NH$_2$)=N—OH; R$^3$ represents C$_{1-3}$alkyl; R$^4$ represents fluoro; and R$^5$, R$^6$ and R$^7$ represent hydrogen.

9. A compound as claimed in claim 1, in which R$^1$ is selected from C$_{2-6}$alkenyl, N(R$^B$)$_2$, phenyl or 5-10 membered heterocyclyl, wherein said phenyl or heterocyclyl is either unsubstituted or said phenyl or heterocyclyl is substituted with from 1 to 3 substituents, each substituent being independently selected from the group consisting of halogen, cyano, nitro, C$_{1-6}$alkyl and trihaloC$_{1-6}$alkyl; and each R$^B$ represents C$_{1-6}$alkyl;

R$^2$ is selected from the group consisting of —CH=N—OH, and —C(NH$_2$)=N—OH;

R$^3$ is selected from the group consisting of hydrogen, halogen, C$_{1-6}$alkyl, C$_{2-6}$alkenyl, C$_{2-6}$alkynyl, and C$_{3-8}$cycloalkyl; and each of R$^4$, R$^5$, R$^6$ and R$^7$ independently represents hydrogen, halogen, cyano, nitro or C$_{1-6}$alkyl.

10. A compound as claimed in claim 9, in which each of R$^4$, R$^5$, R$^6$ and R$^7$ is independently selected from the group consisting of hydrogen, halogen and methyl.

11. A compound as claimed in claim 9, in which R$^4$ represents hydrogen, halogen or methyl, and R$^5$, R$^6$ and R$^7$ represent hydrogen.

12. A compound as claimed in claim 11, in which R$^4$ represents fluoro.

13. A compound as claimed in claim 9, in which G represents

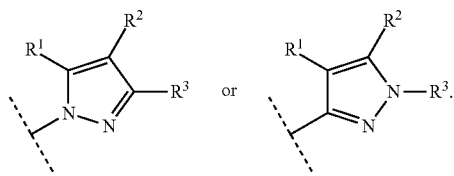

14. A compound as claimed in claim 13, in which G represents

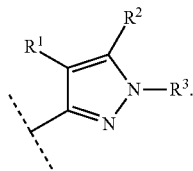

15. A compound as claimed in claim 9, in which $R^2$ is selected from the group consisting of —CH=N—OH, and —C(NH$_2$)=N—OH.

16. A compound as claimed in claim 9, in which $R^3$ is $C_{1-3}$alkyl.

17. A compound as claimed in claim 9, in which $R^1$ is selected from phenyl or 5- or 6-membered heterocyclyl, wherein said phenyl or heterocyclyl is substituted with from 1 to 3 substituents, each substituent being independently selected from the group consisting of halogen and $C_{1-3}$alkyl.

18. A compound as claimed in claim 17, in which $R^1$ represents a 5- or 6-membered heterocyclyl, said heterocyclyl being substituted with two $C_{1-3}$alkyl groups.

19. A compound as claimed in claim 18, in which $R^1$ represents a 5-membered heterocyclyl, said heterocyclyl being substituted with two methyl groups.

20. A compound as claimed in claim 19, in which said 5-membered heterocyclyl is selected from isoxazolyl, isothiazolyl, pyrrolyl, furanyl, pyrazolyl or thiophenyl.

21. A compound as claimed in claim 20, in which said 5-membered heterocyclyl is dimethylisoxazolyl.

22. A compound according to claim 9, in which G represents

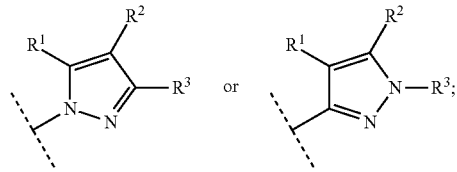

$R^1$ is selected from $C_{2-6}$alkenyl, N(R$^B$)$_2$, phenyl or 5-6 membered heterocyclyl, wherein said phenyl or heterocyclyl group is substituted with from 1 to 3 substituents, each substituent being independently selected from the group consisting of halogen, cyano and $C_{1-3}$alkyl; and each R$^B$ representing $C_{1-3}$alkyl;

$R^2$ is selected from the group consisting of —CH=N—OH, and —C(NH$_2$)=N—OH;

$R^3$ is selected from the group consisting of hydrogen and $C_{1-6}$alkyl; and each of $R^4$, $R^5$, $R^6$ and $R^7$ independently represents hydrogen, halogen or methyl.

23. A compound according to claim 9, in which G represents

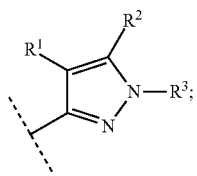

$R^1$ represents a 5-membered heterocyclyl, said heterocyclyl being substituted with two methyl groups;

$R^2$ is selected from the group consisting of —CH=N—OH, and —C(NH$_2$)=N—OH;

$R^3$ is hydrogen or $C_{1-3}$alkyl;

$R^4$ represents halogen; and $R^5$, $R^6$ and $R^7$ each represent hydrogen.

24. A compound as claimed in claim 1, which is any one of the following compounds:

5-(3,5-dimethylisoxazol-4-yl)-N'-hydroxy-1-(4-hydroxyphenyl)-3-methyl-1H-pyrazole-4-carboximidamide;

5-(3,5-dimethylisoxazol-4-yl)-1-(4-hydroxyphenyl)-3-methyl-1H-pyrazole-4-carbaldehyde oxime;

5-(3,5-dimethylisoxazol-4-yl)-1-(4-hydroxyphenyl)-3-propyl-1H-pyrazole-4-carbaldehyde oxime;

5-(3,5-dimethylisoxazol-4-yl)-N'-hydroxy-1-(4-hydroxyphenyl)-3-propyl-1H-pyrazole-4-carboximidamide;

5-(2,5-dimethyl-1H-pyrrol-1-yl)-1-(2-fluoro-4-hydroxyphenyl)-N'-hydroxy-3-methyl-1H-pyrazole-4-carboximidamide;

5-(diethylamino)-3-ethyl-N'-hydroxy-1-(4-hydroxyphenyl)-1H-pyrazole-4-carboximidamide;

5-(1,3-dimethyl-1H-pyrrol-2-yl)-1-(2-fluoro-4-hydroxyphenyl)-N'-hydroxy-3-methyl-1H-pyrazole-4-carboximidamide;

5-(5-bromo-1,3-dimethyl-1H-pyrrol-2-yl)-1-(2-fluoro-4-hydroxyphenyl)-N'-hydroxy-3-methyl-1H-pyrazole-4-carboximidamide;

3-ethyl-N'-hydroxy-1-(4-hydroxyphenyl)-5-(3-methylfuran-2-yl)-1H-pyrazole-4-carboximidamide;

4-(3,5-dimethylisoxazol-4-yl)-3-(4-hydroxyphenyl)-1-methyl-1H-pyrazole-5-carbaldehyde oxime;

4-(3,5-dimethylisoxazol-4-yl)-N'-hydroxy-3-(4-hydroxyphenyl)-1-methyl-1H-pyrazole-5-carboximidamide;

4-(2,6-difluorophenyl)-N'-hydroxy-3-(4-hydroxyphenyl)-1-methyl-1H-pyrazole-5-carboximidamide;

5-(3,5-dimethylisoxazol-4-yl)-1-(4-hydroxyphenyl)-3-isopropyl-1H-pyrazole-4-carbaldehyde oxime;

5-(3,5-dimethylisoxazol-4-yl)-3-ethyl-1-(4-hydroxyphenyl)-1H-pyrazole-4-carbaldehyde oxime;

5-(3,5-dimethylisoxazol-4-yl)-3-ethyl-N'-hydroxy-1-(4-hydroxyphenyl)-1H-pyrazole-4-carboximidamide;

1-(3,5-difluoro-4-hydroxyphenyl)-5-(3,5-dimethylisoxazol-4-yl)-3-ethyl-N'-hydroxy-1H-pyrazole-4-carboximidamide;

5-(3,5-dimethylisoxazol-4-yl)-3-ethyl-1-(3-fluoro-4-hydroxyphenyl)-N'-hydroxy-1H-pyrazole-4-carboximidamide;

1-(2,3-difluoro-4-hydroxyphenyl)-5-(3,5-dimethylisoxazol-4-yl)-3-ethyl-N'-hydroxy-1H-pyrazole-4-carboximidamide;

5-(3,5-dimethylisoxazol-4-yl)-3-ethyl-1-(2-fluoro-4-hydroxyphenyl)-N'-hydroxy-1H-pyrazole-4-carboximidamide;

1-(2,3-difluoro-4-hydroxyphenyl)-5-(3,5-dimethylisoxazol-4-yl)-3-ethyl-1H-pyrazole-4-carbaldehyde oxime (isomer A);

1-(2,3-difluoro-4-hydroxyphenyl)-5-(3,5-dimethylisoxazol-4-yl)-3-ethyl-1H-pyrazole-4-carbaldehyde oxime (isomer B);

5-(3,5-dimethylisoxazol-4-yl)-3-ethyl-1-(2-fluoro-4-hydroxyphenyl)-1H-pyrazole-4-carbaldehyde oxime;

1-(3,5-difluoro-4-hydroxyphenyl)-5-(3,5-dimethylisoxazol-4-yl)-3-ethyl-1H-pyrazole-4-carbaldehyde oxime;

1-(2,5-difluoro-4-hydroxyphenyl)-5-(3,5-dimethylisoxazol-4-yl)-3-ethyl-N'-hydroxy-1H-pyrazole-4-carboximidamide;

1-(2,5-difluoro-4-hydroxyphenyl)-5-(3,5-dimethylisoxazol-4-yl)-3-ethyl-1H-pyrazole-4-carbaldehyde oxime;
5-(3,5-dimethylisoxazol-4-yl)-1-(2-fluoro-4-hydroxyphenyl)-N'-hydroxy-3-methyl-1H-pyrazole-4-carboximidamide;
5-(3,5-dimethylisoxazol-4-yl)-1-(2-fluoro-4-hydroxyphenyl)-N'-hydroxy-3-propyl-1H-pyrazole-4-carboximidamide;
5-(3,5-dimethylisoxazol-4-yl)-1-(2-fluoro-4-hydroxyphenyl)-3-methyl-1H-pyrazole-4-carbaldehyde oxime;
1-(2,3-difluoro-4-hydroxyphenyl)-3-ethyl-5-(1-methyl-1H-pyrrol-2-yl)-1H-pyrazole-4-carbaldehyde oxime;
2-(2-fluoro-4-hydroxyphenyl)-2',4',5-trimethyl-2H,2'H-3,3'-bipyrazole-4-carbaldehyde oxime;
2-(2-fluoro-4-hydroxyphenyl)-N'-hydroxy-2',4',5-trimethyl-2H,2'H-3,3'-bipyrazole-4-carboximidamide;
5-(2,6-dimethylphenyl)-1-(2-fluoro-4-hydroxyphenyl)-N'-hydroxy-3-methyl-1H-pyrazole-4-carboximidamide;
5-(2,5-dimethyl-1H-pyrrol-1-yl)-3-ethyl-N'-hydroxy-1-(4-hydroxyphenyl)-1H-pyrazole-4-carboximidamide;
5-(2,6-dimethylphenyl)-1-(2-fluoro-4-hydroxyphenyl)-3-methyl-1H-pyrazole-4-carbaldehyde oxime;
5-(2,5-dimethyl-1H-pyrrol-1-yl)-1-(3-fluoro-4-hydroxyphenyl)-N'-hydroxy-3-methyl-1H-pyrazole-4-carboximidamide;
1-(2,3-difluoro-4-hydroxyphenyl)-5-(2,5-dimethyl-1H-pyrrol-1-yl)-N'-hydroxy-3-methyl-1H-pyrazole-4-carboximidamide;
1-(3,5-difluoro-4-hydroxyphenyl)-5-(2,5-dimethyl-1H-pyrrol-1-yl)-N'-hydroxy-3-methyl-1H-pyrazole-4-carboximidamide;
4-(2,6-difluorophenyl)-3-(4-hydroxyphenyl)-1-methyl-1H-pyrazole-5-carbaldehyde oxime;
4-(2,6-dichlorophenyl)-3-(4-hydroxyphenyl)-1-methyl-1H-pyrazole-5-carbaldehyde oxime;
4-(2,6-dichlorophenyl)-N'-hydroxy-3-(4-hydroxyphenyl)-1-methyl-1H-pyrazole-5-carboximidamide;
4-(3,5-dimethylisoxazol-4-yl)-3-(2-fluoro-4-hydroxyphenyl)-1-methyl-1H-pyrazole-5-carbaldehyde oxime;
4-(3,5-dimethylisoxazol-4-yl)-3-(2-fluoro-4-hydroxyphenyl)-N'-hydroxy-1-methyl-1H-pyrazole-5-carboximidamide;
5-((Z)-but-2-en-2-yl)-1-(2-fluoro-4-hydroxyphenyl)-N'-hydroxy-3-methyl-1H-pyrazole-4-carboximidamide;
5-(2,4-dimethylthiophen-3-yl)-1-(2-fluoro-4-hydroxyphenyl)-N'-hydroxy-3-methyl-1H-pyrazole-4-carboximidamide;
5-(3,5-dimethylpyridin-4-yl)-1-(2-fluoro-4-hydroxyphenyl)-N'-hydroxy-3-methyl-1H-pyrazole-4-carboximidamide;
5-(3,5-dimethylisoxazol-4-yl)-N'-hydroxy-1-(4-hydroxy-2-methylphenyl)-3-methyl-1H-pyrazole-4-carboximidamide;
5-(3,5-dimethylisoxazol-4-yl)-3-ethyl-N'-hydroxy-1-(4-hydroxy-2-methylphenyl)-1H-pyrazole-4-carboximidamide;
5-(2,5-dimethyl-1H-pyrrol-1-yl)-N'-hydroxy-1-(4-hydroxy-2-methylphenyl)-3-methyl-1H-pyrazole-4-carboximidamide;
N'-hydroxy-1-(4-hydroxy-2-methylphenyl)-3-methyl-5-(2-methyl-5-propyl-1H-pyrrol-1-yl)-1H-pyrazole-4-carboximidamide;
4-(2,4-dimethylthiophen-3-yl)-3-(2-fluoro-4-hydroxyphenyl)-N'-hydroxy-1-methyl-1H-pyrazole-5-carboximidamide;
4-(3,5-dimethylisoxazol-4-yl)-3-(3-fluoro-4-hydroxyphenyl)-1-methyl-1H-pyrazole-5-carbaldehyde oxime;
4-(3,5-dimethylisoxazol-4-yl)-3-(3-fluoro-4-hydroxyphenyl)-N'-hydroxy-1-methyl-1H-pyrazole-5-carboximidamide;
(Z)-4-(3,5-dimethylisoxazol-4-yl)-3-(4-hydroxy-2-methylphenyl)-1-methyl-1H-pyrazole-5-carbaldehyde oxime;
(E)-4-(3,5-dimethylisoxazol-4-yl)-3-(4-hydroxy-2-methylphenyl)-1-methyl-1H-pyrazole-5-carbaldehyde oxime;
4-(3,5-dimethylisoxazol-4-yl)-N'-hydroxy-3-(4-hydroxy-2-methylphenyl)-1-methyl-1H-pyrazole-5-carboximidamide;
4-(2,4-dimethylthiophen-3-yl)-N'-hydroxy-3-(4-hydroxy-2-methylphenyl)-1-methyl-1H-pyrazole-5-carboximidamide;
4-(3,5-dimethylisothiazol-4-yl)-3-(2-fluoro-4-hydroxyphenyl)-N'-hydroxy-1-methyl-1H-pyrazole-5-carboximidamide;
4-(2,6-dimethylphenyl)-3-(2-fluoro-4-hydroxyphenyl)-N'-hydroxy-1-methyl-1H-pyrazole-5-carboximidamide;
4-(2,4-dimethylfuran-3-yl)-3-(4-hydroxyphenyl)-1-methyl-1H-pyrazole-5-carbaldehyde oxime;
4-(3,5-dimethylisothiazol-4-yl)-3-(4-hydroxyphenyl)-1-methyl-1H-pyrazole-5-carbaldehyde oxime;
4-(3,5-dimethylisothiazol-4-yl)-N'-hydroxy-3-(4-hydroxyphenyl)-1-methyl-1H-pyrazole-5-carboximidamide;
or a pharmaceutically acceptable ester, amide, solvate or salt thereof, or a salt of such an ester or amide, or a solvate of such an ester, amide or salt.

25. A pharmaceutical composition which comprises a compound as claimed in claim 1, together with a pharmaceutically acceptable carrier, and optionally together with a therapeutic agent.

* * * * *